(12) United States Patent
Sahin et al.

(10) Patent No.: US 9,475,867 B2
(45) Date of Patent: *Oct. 25, 2016

(54) MONOCLONAL ANTIBODIES FOR TREATMENT OF CANCER

(71) Applicants: GANYMED PHARMACEUTICALS AG, Mainz (DE); Johannes Gutenberg-Universität Mainz, Mainz (DE)

(72) Inventors: Ugur Sahin, Mainz (DE); Michael Koslowski, Mainz (DE); Özlem Türeci, Mainz (DE)

(73) Assignees: GANYMED PHARMACEUTICALS AG, Mainz (DE); Johannes Gutenberg-Universität Mainz, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/604,447

(22) Filed: Jan. 23, 2015

(65) Prior Publication Data

US 2015/0175686 A1    Jun. 25, 2015

Related U.S. Application Data

(60) Continuation of application No. 13/710,828, filed on Dec. 11, 2012, now Pat. No. 8,961,980, which is a division of application No. 12/531,267, filed as application No. PCT/EP2008/002063 on Mar. 14, 2008, now Pat. No. 8,354,104.

(60) Provisional application No. 60/894,860, filed on Mar. 14, 2007.

(30) Foreign Application Priority Data

Mar. 14, 2007 (EP) .................... 07005258

(51) Int. Cl.
| | |
|---|---|
| A61K 39/395 | (2006.01) |
| C07K 16/18 | (2006.01) |
| C07K 16/30 | (2006.01) |
| A61K 47/48 | (2006.01) |

(52) U.S. Cl.
CPC ......... *C07K 16/18* (2013.01); *A61K 47/48569* (2013.01); *C07K 16/30* (2013.01); *C07K 2316/96* (2013.01); *C07K 2317/34* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant et al. | |
| 4,447,233 A | 5/1984 | Mayfield | |
| 4,474,893 A | 10/1984 | Reading | |
| 4,475,196 A | 10/1984 | La Zor | |
| 4,486,194 A | 12/1984 | Ferrara | |
| 4,487,603 A | 12/1984 | Harris | |
| 4,522,811 A | 6/1985 | Eppstein et al. | |
| 4,596,556 A | 6/1986 | Morrow et al. | |
| 4,790,824 A | 12/1988 | Morrow et al. | |
| 4,881,175 A | 11/1989 | Ladner | |
| 4,941,880 A | 7/1990 | Burns | |
| 4,946,778 A | 8/1990 | Ladner et al. | |
| 4,954,617 A | 9/1990 | Fanger et al. | |
| 5,013,653 A | 5/1991 | Huston et al. | |
| 5,064,413 A | 11/1991 | McKinnon et al. | |
| 5,091,513 A | 2/1992 | Huston et al. | |
| 5,132,405 A | 7/1992 | Huston et al. | |
| 5,258,498 A | 11/1993 | Huston et al. | |
| 5,260,203 A | 11/1993 | Ladner et al. | |
| 5,312,335 A | 5/1994 | McKinnon et al. | |
| 5,374,548 A | 12/1994 | Caras | |
| 5,383,851 A | 1/1995 | McKinnon et al. | |
| 5,399,163 A | 3/1995 | Peterson et al. | |
| 5,399,331 A | 3/1995 | Loughrey et al. | |
| 5,416,016 A | 5/1995 | Low et al. | |
| 5,455,030 A | 10/1995 | Ladner et al. | |
| 5,476,786 A | 12/1995 | Huston | |
| 5,482,858 A | 1/1996 | Huston et al. | |
| 5,624,821 A | 4/1997 | Winter et al. | |
| 5,648,260 A | 7/1997 | Winter et al. | |
| 5,744,585 A | 4/1998 | Medenica et al. | |
| 6,121,022 A | 9/2000 | Presta et al. | |
| 6,194,551 B1 | 2/2001 | Idusogie et al. | |
| 6,277,375 B1 | 8/2001 | Ward | |
| 6,812,339 B1 | 11/2004 | Venter et al. | |

(Continued)

FOREIGN PATENT DOCUMENTS

| | | |
|---|---|---|
| CN | 1663603 | 9/2005 |
| EP | 0338841 | 10/1989 |

(Continued)

OTHER PUBLICATIONS

Ranade, J. Clin. Pharmacol., 29:685-694 (1989).
Rice et al., Trends Genet., 16:276-277 (2000).
Riechmann et al., Nature, 332:323-327 (1998).
Rossi et al., Am. J. Clin. Pathol., 124:295-302 (2005).
Scheurle et al., Cancer Res., 60:4037-4043 (2000).
Sherr, Cancer Res., 60:3689-3695 (2000).
Sherr, Cell, 73:1059-1065 (1993).
Shields et al., J. Biol. Chem., 277:26733-26740 (2002).

(Continued)

*Primary Examiner* — Sheela J Huff
(74) *Attorney, Agent, or Firm* — McAndrews, Held & Malloy, Ltd.

(57) ABSTRACT

The present invention provides antibodies useful as therapeutics for treating and/or preventing diseases associated with cells expressing GT468, including tumor-related diseases such as breast cancer, lung cancer, gastric cancer, ovarian cancer, and hepatocellular cancer.

18 Claims, 16 Drawing Sheets

(56) References Cited

U.S. PATENT DOCUMENTS

| | | | |
|---|---|---|---|
| 8,946,388 B2* | 2/2015 | Sahin | C07K 16/30 530/387.1 |
| 8,961,980 B2* | 2/2015 | Sahin | C07K 16/30 424/138.1 |
| 8,975,375 B2* | 3/2015 | Sahin | C07K 14/4748 424/139.1 |
| 9,216,218 B2* | 12/2015 | Sahin | A61K 39/39558 |
| 2002/0065394 A1 | 5/2002 | Jacobs et al. | |
| 2002/0177547 A1 | 11/2002 | Molling et al. | |
| 2002/0192748 A1 | 12/2002 | Rastelli et al. | |
| 2003/0017534 A1 | 1/2003 | Buelow et al. | |
| 2003/0118592 A1 | 6/2003 | Ledbetter et al. | |
| 2003/0133939 A1 | 7/2003 | Ledbetter et al. | |
| 2004/0043387 A1 | 3/2004 | Liu et al. | |
| 2004/0203037 A1 | 10/2004 | Lo et al. | |
| 2005/0255114 A1 | 11/2005 | Labat et al. | |
| 2011/0223182 A1 | 9/2011 | Sahin et al. | |
| 2011/0300144 A1 | 12/2011 | Sahin et al. | |
| 2011/0318264 A1 | 12/2011 | Sahin et al. | |

FOREIGN PATENT DOCUMENTS

| | | |
|---|---|---|
| EP | 1762575 A | 3/2007 |
| EP | 1970384 A1 | 9/2008 |
| EP | 2166021 A1 | 3/2010 |
| JP | 2389675 B2 | 1/2014 |
| MX | 2009009816 A | 11/2009 |
| WO | 87/04462 | 7/1987 |
| WO | 88/00052 | 1/1988 |
| WO | 89/01036 | 2/1989 |
| WO | 94/10332 | 5/1994 |
| WO | 99/45962 | 9/1999 |
| WO | 00/32769 | 6/2000 |
| WO | 02/43478 | 6/2002 |
| WO | 03/016475 A2 | 2/2003 |
| WO | 03/075014 A2 | 9/2003 |
| WO | 03/102159 A2 | 12/2003 |
| WO | 2004/035607 | 4/2004 |
| WO | 2004/065629 A1 | 8/2004 |
| WO | 2007031222 * | 3/2007 |
| WO | 2008/110379 A2 | 9/2008 |
| WO | 2010/031551 A2 | 3/2010 |

OTHER PUBLICATIONS

Slamon et al., Science, 244:707-712 (1989).
Spieker-Polet et al., Proc. Natl. Acad. Sci. USA, 92:9348-9352 (1995).
Strejan et al., J. Neuroimmunol., 7:27-41 (1984).
Sutherland et al., J. Mammary Gland Biol. Neoplasia, 9:95-104 (2004).
Thorpe et al., Immunol. Rev., 62:119-158 (1982).
Umezawa et al., Biochem. Biophys. Res. Commun., 153:1038-1044 (1988).
Verma et al., J. Immunol. Methods, 216:165-181 (1998).
Ward et al., Nature, 341:544-546 (1989).
Yang et al., Proc. Natl. Acad. Sci. USA, 100(12):6934-6939 (2003).
Roguska et al., Current Protocols in Pharmacology 2005 (Abstract).
Scallon et al., J Immunother 2006, 29:351-364.
Weiner et al., Lancet 2009, 373(9668):1033-1040.
Lacroix et al., Relevance of breast cancer cell lines as models for breast tumours: an update, Breast Cancer Research and Treatment 83:249-289 (2004).
"Human protein Q9H2U9, SEQ ID No. 9901", Jan. 29, 2004, retrieved from EBI accession No. GSP: ADE63955, Database accession No. ADE63955.
"Novel human nucleic acid NOV22c", Mar. 25, 2004, retrieved from EBI accession No. GSN:ADH41740, Database accession No. ADH41740, sequence.
Database Geneseq [Online], May 20, 2004, "Human ADAM7 (GP-83) beta form cDNA.", retrieved from EBI accession No. GSN:ADJ92368, Database accession No. ADJ92368, sequence.
*Homo sapiens* a disintegrin and metalloproteinase 7 (ADAM7) mRNA, compldete cds. [online]. Jan. 2, 2001 uploaded. NCBI Entrez Nucleotide, Accession No. AF215824 (GI:12004291) [Retrieved on Jun. 5, 2014]. Retrieved from the Internet: URL:http://www.ncbi.nlm.nih.gov/nuccore/12004291.
Proceedings of the Japanese Cancer Association, (2002), 61st, p. 390 (1840).
Ernst et al., "Decrease and Gain of Gene Expression Are Equally Discriminatory Markers for Prostate Carcinoma", Amer. Journ. Pathology, vol. 160, No. 6, Jun. 2002 (+ SEQ ID No. 5).
Yan et al., "Oosp1 Encodes a Novel Mouse Oocyte-Secreted Protein" genesis 31:105-110 (2001).
Lu et al., "Selection of Potential Markers for Epithelial Ovarian Cancer with Gene Expression Arrays and Recursive Descent Partition Analysis", Vo. 10, pp. 3291-3300, May 15, 2004.
Lin Y C et al: "Cloning and characterization of a complementary DNA encoding a human epididymis-associated disintegrin and metalloprotease 7 protein.", Biology of Reproduction Sep. 2001, vol. 65, No. 3, pp. 944-950.
Bendig M. M., Methods: A Companion to Methods in Enzymology, 1995; 8:83-93.
Colman, Research in Immunology, vol. 145, p. 33-36, 1994.
Rudikoff, Proceedings of the National Academy of Sciences, U.S.A., vol. 79, p. 1979-1983, 1982.
Paul, Fundamental Immunology, Third Edition, p. 292-295, 1993.
Harris, Biotechnology, vol. 11, p. 1293-1297, 1993.
Sominskaya, Medical Microbiology and Immunology, vol. 181, p. 215-226, 1992.
Int'l Search Report and Written Opinion for PCT/EP2011/001198, dated May 12, 2011.
IPRP and Written Opinion of PCT/EP2011/001198 issued Sep. 25, 2012.
Binz et al., Nat. Biotechnol., 23(10):1257-1268 (2005).
Bird et al., Science, 242:423-426 (1988).
Molecular Cloning: A Laboratory Manual, J. Sambrook et al., Editors, 2nd Edition, Cold Spring Harbor Laboratory Press, Cold Spring Harbor, New York (1989).
Smith et al., Ads App. Math., 2:482 (1981).
Pearson et al., Proc. Natl. Acad. Sci. USA, 85:2444 (1988).
Neddleman et al., J. Mol. Biol., 48:443 (1970).
Morton et al., Critical Reviews in Immunology, 16:423-440 (1996).
Weintraub, B. Principles of Radioimmunoassays, Seventh Training Course on Radioligand Assay Techniques, The Endocrine Society, Mar. 1986.
Arnon et al., "Monoclonal Antibodies for Immunotargeting of Drugs in Cancer Therapy", in Monoclonal Antibodies and Cancer Therapy, Resifeld et al. (eds.), pp. 243-256 (Alan R. Liss, Inc. 1985).
Robinson et al. (eds.), pp. 623-653 (Marcel Dekker, Inc. 1987).
"Analysis, Results, and Future Prospective of the Therapeutic Use of Radiolabeled Antibody in Cancer Therapy", in Monoclonal Antibodies for Cancer Detection and Therapy, Baldwin et al. (eds.), pp. 303-316 (Academic Press 1985).
Briscoe et al., Am. J. Physiol., 1233:134 (1995).
Hofmann, K and Stoffel, W., Biol. Chem Hoppe-Seyler 374, 166 (1993).
IPRP and Written Opinion of PCT/EP2009/006704 mailed on Mar. 31, 2011.
Dr. Rainer Wessel, "Neue, hoch tumorspezifische Antikörper und ihre Targets" [online] Nov. 22, 2007, pp. 1-30, XP002527064 Würzburg Retrieved from the Internet: URL :http://www.bayern-innovativ.de.ib.site/documents/media/8b861e13-3717-d967-ed57-03d37f988a16.pdf/Wessel.pdf.
Thorpe, "Antibody Carriers of Cytotoxic Agents in Cancer Therapy: A Review", in Monoclonal Antibodies '84: Biological and Clinical Applications, (1985).
Pinchera et al. (eds.), pp. 475-506 (1985).
Final Office Action, U.S. Appl. No. 13/086,176, dated Sep. 25, 2012.
RCE, U.S. Appl. No. 13/086,176, dated Jan. 9, 2013.
Examiner sequence search result (Chen) in U.S. Appl. No. 12/066,399, dated Oct. 14, 2010.

(56) References Cited

OTHER PUBLICATIONS

Examiner sequence search result (Jacobs) in U.S. Appl. No. 12/066,399,dated Oct. 14, 2010.
Examiner sequence search result (Daviet) in U.S. Appl. No. 12/066,399,dated Oct. 14, 2010.
Pardoll, M., Cancer Vaccines, Nature Medicine, May 1998, pp. 525-531, vol. 4., No. 5, Nature Publishing Group, New York, NY, US.
Sahin, U. et al.,Serological Identification of Human Tumor Antigens, Current Opinion in Immunology, Oct. 1997, pp. 709-716, vol. 9, No. 5, Current Biology Ltd.
Bruggen Van Der, P. et al., A Gene Encoding an Antigen Recognized by Cytolytic T Lymphocytes on a Human Melanoma, Science, Dec. 13, 1991, pp. 1643-1647, vol. 254, American Association for the Advancement of Science, US.
Nakata Yuji et al., Nucleic Acid Modulation of Gene Expression: Approaches for Nucleic Acid Therapeutics Against Cancer, Critical Reviews in Eukaryotic Gene Expression, 2005, pp. 163-182, vol. 15, No. 2.
Otsuki, T. et al. DNA Res., 2005, pp. 117-126, vol. 12, No. 2.
EMBL Database, Database accession No. AK075086, Sep. 7, 2002, webpage printout.
IPRP for PCT/EP2006/008695, mailed Mar. 27, 2008.
Int'l and Written Opinion for PCT/EP2006/008695, mailed Jun. 13, 2007.
Restriction Requirement, U.S. Appl. No. 12/066,399, dated Apr. 28, 2010.
Non-Final Office Action, U.S. Appl. No. 12/066,399, dated Oct. 14, 2010.
Freshney (Culture of Animals Cells, A Manual of Basic Technique, Alan R. Liss, Inc., 1983 New York, p. 4).
Dermer (Bio/Technology, 1994, 12:320).
Gura (Science, 1997, 278:1041-1042).
Jain (Sci. Am., 1994, 271:58-65).
Babcook et al., 1996.
Welschof and Kraus, Recombinant antibodies for cancer therapy ISBN-0-89603-918-8, (table of contents only) 2003.
Fant et al., Mol Reprod Dev. 63:430-6, 2002.
Seals et al., Genes Dev. 17(1) :7-30, 2003.
Adachi et al., Mol Reprod Dev. 64:414-21, 2003.
Beauchemin et al., Exp Cell Res. 252(2) :243-9, 1999.
Salahshor et al, BMC Cancer. 5:66, 2005.
Cheng et al., J Bioi. Chem. 260:15834-9, 1985.
Boehm et al., J Immunoi. 161(12):6715-23, 1998.
Guenzi et al., EMBO J. 20(20) :5568-77, 2001.
Arunachalam et al. Proc. Natl Acad Sci U S A. 97(2):745-50, 2000.
Bera et al., Biochem Biophys Res Commun. 312(4):1209-15, 2003.
Int'l Search Report and Written Opinion for PCT/EP2009/006704, dated Aug. 2, 2010, 24 pages.
Evans et al., Serum-free hybridoma culture: ethical, scientific and safety considerations, TRENDS in Biotechnology, Vo. 24 No. 3, (105-108) Mar. 2006.
Schultze-Mosgau et al., (1975) Fetal placental antigens in the serum of tumor patients; Zentralblatt für Gynäkologie 97 (9):563-567.
Chang et al., (1977) Preliminary characterization of isoimmunogenic placental antigens in the rabbit; Tissue Antigens 10(1):16-26.
Cancer Immunity, 2007, vol. 7, p. 18.
Aschheim Kathy et al: "Focus on antibody engineering and manufacture", Nature Biotechnology, vol. 23, No. 9, Sep. 1, 2005, pp. vii-viii.
International Preliminary Report on Patentability dated Sep. 24, 2009 for International Application No. PCT/EP2008/002063.
Chen Jing et al: "[PLAC1/CP1 gene expression and autologous humoral immunity in gastric cancer patients]" Beijing Da Xue Xue Bao. Yi Xue Ban= Journal of Peking University. Health Sciences Apr. 18, 2006, vol. 38, No. 2, Apr. 18, 2006, pp. 124-127, XP009085470 ISSN: 1671-167X.
Cocchia M et al: "PLAC1, an Xq26 Gene with Placenta-Specific Expression" Genomics, Academic Press, San Diego, US, vol. 68, No. 3, Sep. 15, 2000, pp. 305-312, XP004437833 ISSN: 0888-7543.
Koslowski Michael et al: "A placenta-specific gene ectopically activated in many human cancers is essentially involved in malignant cell processes" Cancer Research, American Association for Cancer Research, Baltimore, MD, vol. 67, No. 19, Oct. 1, 2007, pp. 9528-9534, XP002471063 ISSN: 0008-5472.
Dong Xue-Yuan et al: "PLAC1 is a tumor-specific antigen capable of eliciting spontaneous antibody responses in human cancer patients" International Journal of Cancer, vol. 122, No. 9, May 2008, pp. 2038-2043, XP009102971 ISSN: 0020-7136.
Adams et al., Nat. Biotechnol., 23:1147-1157 (2005).
Berge et al., J. Pharm. Sci., 66:1-19 (1977).
Bloemen et al., FEBS Lett., 357:140-144 (1995).
Bork et al., FEBS Lett, 300:237-240 (1992).
Brekke et al., Nat. Rev. Drug Discov., 2:52-62 (2003).
Brennan et al., Science, 229:81-83 (1985).
Caldon et al., J. Cell Biochem., 97:261-274 (2006).
Cantley, Science, 296:1655-1657 (2002).
Carter, Nat. Rev. Cancer, 1:118-129 (2001).
Crone et al., Nat. Med., 8:459-465 (2002).
Cunningham-Rundles et al., J. Immunol. Methods, 152:177-190 (1992).
D'Amico et al., J. Biol. Chem., 275:32649-32657 (2000).
Diehl et al., Genes Dev., 12:3499-3511 (1998).
Fischer et al., Biol. Chem., 380:825-839 (1999).
Garnier et al., J. Mol. Biol., 120:97-120 (1978).
Glennie et al., J. Immunol., 139:2367-2375 (1987).
Graziano et al., J. Immunol., 155(10):4996-5002 (1995).
Holliger et al., Proc. Natl. Acad. Sci. USA, 90:6444-6448 (1993).
Houshmand et al., Curr. Opin. Cell Biol., 15:640-644 (2003).
Huston et al., Proc. Natl. Acad. Sci. USA, 85:5879-5883 (1988).
Jones et al., Biochemistry, 33:3038-3049 (1994).
Jones et al., Nature, 321:522-525 (1986).
Jovine et al., BMC Biochem, 7:11 (2006).
Karpovsky et al., J. Exp. Med., 160:1686-1701 (1984).
Kohler et al., Nature, 256:495-497 (1975).
Koslowski et al., Cancer Res., 62:6750-6755 (2002).
Koslowski et al., Cancer Res., 64:5988-5993 (2004).
Koslowski et al., Hum. Mol. Genet., 15:2392-2399 (2006).
Kozak, J. Biol. Chem., 266:19867-19870 (1991).
Kranz et al., Proc. Natl. Acad. Sci. USA, 78:5807-5811 (1981).
Landor, Ann. Allergy Asthma Immunol., 74:279-283 (1995).
Liu et al., Proc. Natl. Acad. Sci. USA, 82:8648-8652 (1985).
Luo et al., Cancer Cell, 4:257-262 (2003).
Monteiro et al., J. Immunol., 148:1764-1770 (1992).
Morgan, Annu. Rev. Cell Dev. Biol., 13:261-291 (1997).
Morrison, Science, 229:1202-1207 (1985).
Muise-Helmericks et al., J. Biol. Chem., 273:29864-29872 (1998).
Owais et al., Antimicrob. Agents Chemother., 39:180-184 (1995).
Paulus, Behring Ins. Mitt., (78):118-132 (1985).
Poljak, Structure, 2:1121-1123 (1994).
Pollock et al., J. Immunol. Methods, 231:147-157 (1999).
Queen et al., Proc. Natl. Acad. Sci. USA, 86:10029-10033 (1989).
Radu et al., Mol. Cell Biol., 23:6139-6149 (2003).
Houdebine et al., Journ Biotechnology, vol. 34, 1994, pp. 269-287.
Kappel et al., Current Opinions, Biotechnology vol. 3, 1992, pp. 548-553.
Panka et al., Nat Acad Sciences, 1988, vol. 85.
Wall et al., Theriogenology, vol. 45, 1996, pp. 57-68.

\* cited by examiner

Fig. 1
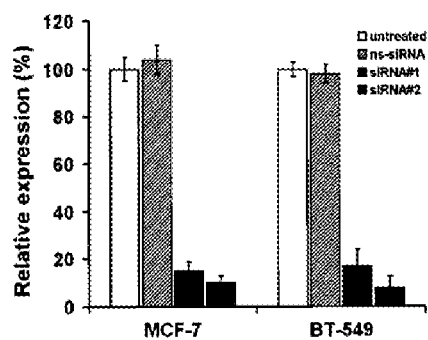
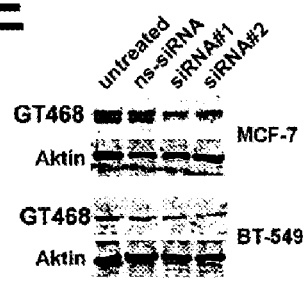
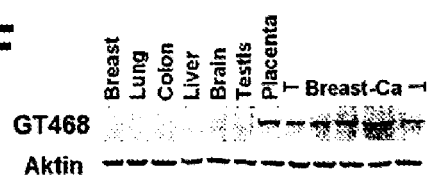
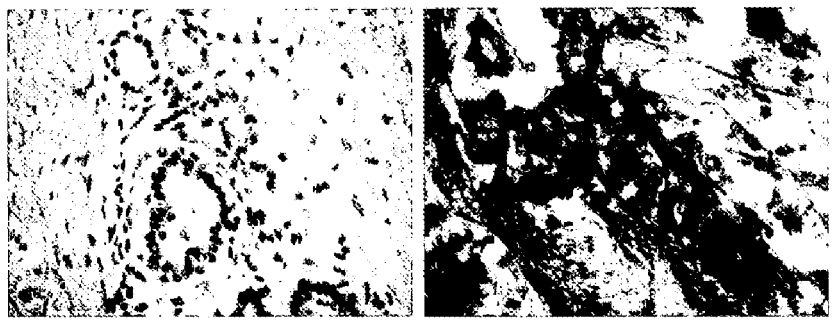

Fig. 2
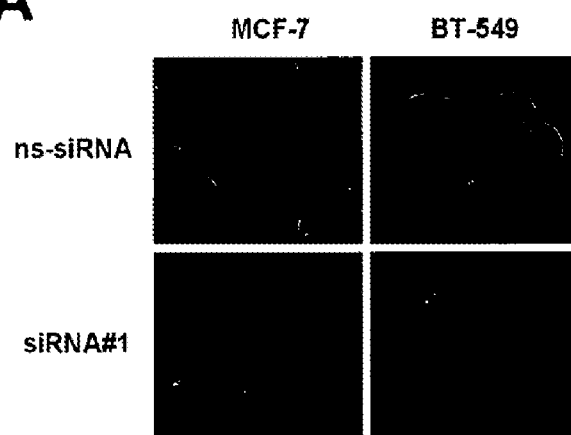
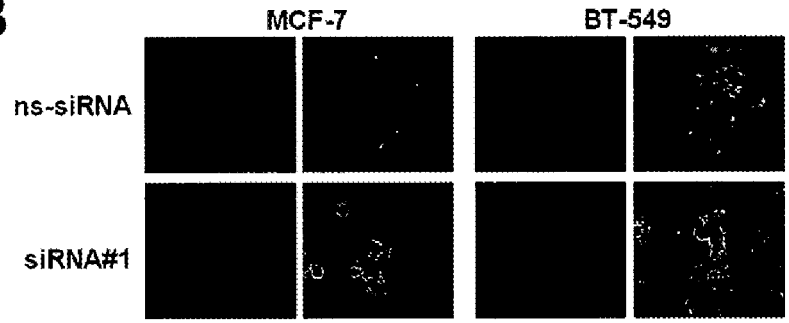

Fig. 6
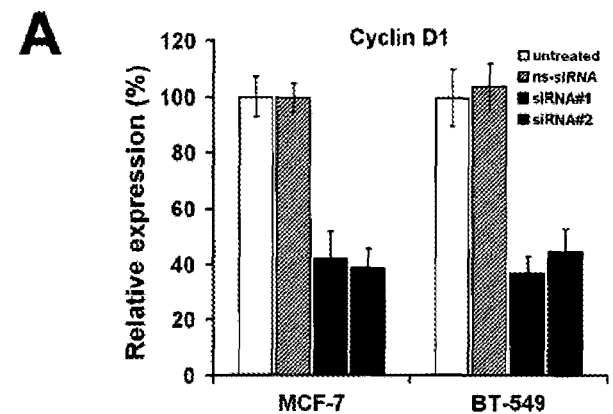
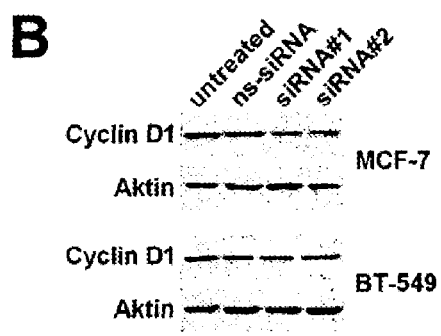
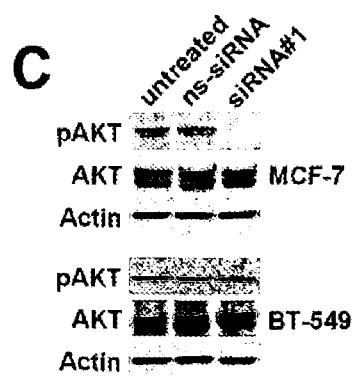 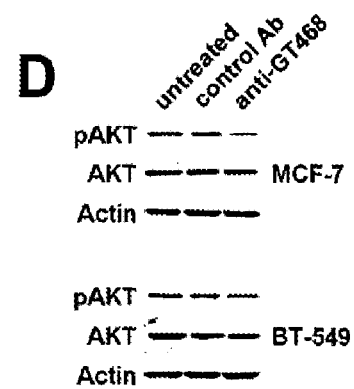

Fig. 13

| Peptide | Sequence | Seq ID No | Peptide | Sequence | Seq ID No |
|---|---|---|---|---|---|
| 1 | MKVFKFIGLMILLTS | 29 | 26 | SSKGTPSKFVIPVSC | 54 |
| 2 | KFIGLMILLTSAFSA | 30 | 27 | TPSKFVIPVSCAAPQ | 55 |
| 3 | LMILLTSAFSAGSGQ | 31 | 28 | FVIPVSCAAPQKSPW | 56 |
| 4 | LTSAFSAGSGQSPMT | 32 | 29 | VSCAAPQKSPWLTKP | 57 |
| 5 | FSAGSGQSPMTVLCS | 33 | 30 | APQKSPWLTKPCSMR | 58 |
| 6 | SGQSPMTVLCSIDWF | 34 | 31 | SPWLTKPCSMRVASK | 59 |
| 7 | PMTVLCSIDWFMVTV | 35 | 32 | TKPCSMRVASKSRAT | 60 |
| 8 | LCSIDWFMVTVHPFM | 36 | 33 | SMRVASKSRATAQKD | 61 |
| 9 | DWFMVTVHPFMLNND | 37 | 34 | ASKSRATAQKDEKCY | 62 |
| 10 | VTVHPFMLNNDVCVH | 38 | 35 | RATAQKDEKCYEVFS | 63 |
| 11 | PFMLNNDVCVHFHEL | 39 | 36 | QKDEKCYEVFSLSQS | 64 |
| 12 | NNDVCVHFHELHLGL | 40 | 37 | KCYEVFSLSQSSQRP | 65 |
| 13 | CVHFHELHLGLGCPP | 41 | 38 | VFSLSQSSQRPNCDC | 66 |
| 14 | HELHLGLGCPPNHVQ | 42 | 39 | SQSSQRPNCDCPPCV | 67 |
| 15 | LGLGCPPNHVQPHAY | 43 | 40 | QRPNCDCPPCVFSEE | 68 |
| 16 | CPPNHVQPHAYQFTY | 44 | 41 | CDCPPCVFSEEEHTQ | 69 |
| 17 | HVQPHAYQFTYRVTE | 45 | 42 | PCVFSEEEHTQVPCH | 70 |
| 18 | HAYQFTYRVTECGIR | 46 | 43 | SEEEHTQVPCHQAGA | 71 |
| 19 | FTYRVTECGIRAKAV | 47 | 44 | HTQVPCHQAGAQEAQ | 72 |
| 20 | VTECGIRAKAVSQDM | 48 | 45 | PCHQAGAQEAQPLQP | 73 |
| 21 | GIRAKAVSQDMVIYS | 49 | 46 | AGAQEAQPLQPSHFL | 74 |
| 22 | KAVSQDMVIYSTEIH | 50 | 47 | EAQPLQPSHFLDISE | 75 |
| 23 | QDMVIYSTEIHYSSK | 51 | 48 | LQPSHFLDISEDWSL | 76 |
| 24 | IYSTEIHYSSKGTPS | 52 | 49 | HFLDISEDWSLHTDD | 77 |
| 25 | EIHYSSKGTPSKFVI | 53 | 50 | ISEDWSLHTDDMIGS | 78 |
|   |   |   | 51 | SEDWSLHTDDMIGSM | 79 |

| Hybridoma | Reactivity (Peptide) |
|---|---|
| 22-1A-1 | 50+51 |
| 22-2A-1 | 18, 26-31, 42 |
| 22-9B-1 | 27, 29-31 |
| 23-33A-1 | 47+48 |
| 23-19A-1 | 48+49 |

| Hybridoma | Reactivity (Sequence) |
|---|---|
| F11#33 F7 D12 | VFSLSQSSQRPNC (Seq. ID No. 10) |
| 4A12 2D4 1A10 | APQKSPWLTKPC (Seq. ID No. 3) |
| 4A9 1D12 2D | APQKSPWLTKPC (Seq. ID No. 3) |

SEQUENCE LISTING

<160> NUMBER OF SEQ ID NOS: 79

<210> SEQ ID NO 1
<211> LENGTH: 1126
<212> TYPE: DNA
<213> ORGANISM: Homo sapiens

<400> SEQUENCE: 1

```
atatatcaga ccatcagaag gatttgtata aagagtgact ctcctatgaa ggtaaaggcc      60
acccctcttc agttccagtg actgagatac attttccaa tcctgggggc aaatacagac      120
acagcaagtt ccttcttccc tttggaaatt tggcagctgc cttcaccagt gagcacaaag     180
ccacatttca aggaaactg acaaattatc cccagctgcc agaagaagaa atcctcactg      240
gacggcttcc tgtttcctgt ggttcattat ctgattggct gcagggatga agttttaa      300
gttcatagga ctgatgatcc tcctcacctc tgcgtttca gccggttcag gacaaagtcc      360
aatgactgtg ctgtgctcca tagactggtt catggtcaca gtgcacccct tcatgctaaa      420
caacgatgtg tgtgtacact ttcatgaact cacttgggc ctgggttgcc ccccaaacca      480
tgttcagcca cacgcctacc agttcaccta ccgtgttact gaatgtggca tcagggccaa     540
agctgtctct caggacatgg ttatctacag cactgagata cactactctt ctaagggcac     600
gccatctaag tttgtgatcc cagtgtcatg tgctgcccc caaaagtccc catggctcac       660
caagccctgc tccatgagag tagccagcaa gagcagggcc acagcccaga aggatgagaa     720
atgctacgag gtgttcagct tgtcacagtc cagtcaaagg cccaactgcg attgtccacc     780
ttgtgtcttc agtgaagaag agcataccca ggtcccttgt caccaagcag gggctcagga     840
ggctcaacct ctgcagccat ctcactttct tgatatttct gaggattggt ctcttcacac     900
agatgatatg attgggtcca tgtgatcctc aggtttgggg tctcctgaag atgctatttc     960
tagaattagt atatagtgta caaatgtctg acaaataagt gctcttgtga ccctcatgtg    1020
agcacttttg agaaagagaa acctatagca acttcatgaa ttaagccttt ttctatattt    1080
ttatattcat gtgtaaacaa aaaataaaat aaaattctga tcgcat                   1126
```

<210> SEQ ID NO 2
<211> LENGTH: 212
<212> TYPE: PRT
<213> ORGANISM: Homo sapiens

<400> SEQUENCE: 2

```
Met Lys Val Phe Lys Phe Ile Gly Leu Met Ile Leu Leu Thr Ser Ala
1               5                   10                  15

Phe Ser Ala Gly Ser Gly Gln Ser Pro Met Thr Val Leu Cys Ser Ile
            20                  25                  30

Asp Trp Phe Met Val Thr Val His Pro Phe Met Leu Asn Asn Asp Val
        35                  40                  45

Cys Val His Phe His Glu Leu His Leu Gly Leu Gly Cys Pro Pro Asn
    50                  55                  60

His Val Gln Pro His Ala Tyr Gln Phe Thr Tyr Arg Val Thr Glu Cys
65                  70                  75                  80

Gly Ile Arg Ala Lys Ala Val Ser Gln Asp Met Val Ile Tyr Ser Thr
                85                  90                  95

Glu Ile His Tyr Ser Ser Lys Gly Thr Pro Ser Lys Phe Val Ile Pro
            100                 105                 110

Val Ser Cys Ala Ala Pro Gln Lys Ser Pro Trp Leu Thr Lys Pro Cys
        115                 120                 125

Ser Met Arg Val Ala Ser Lys Ser Arg Ala Thr Ala Gln Lys Asp Glu
    130                 135                 140

Lys Cys Tyr Glu Val Phe Ser Leu Ser Gln Ser Ser Gln Arg Pro Asn
145                 150                 155                 160

Cys Asp Cys Pro Pro Cys Val Phe Ser Glu Glu Glu His Thr Gln Val
                165                 170                 175
```

```
Pro Cys His Gln Ala Gly Ala Gln Glu Ala Gln Pro Leu Gln Pro Ser
            180                 185                 190

His Phe Leu Asp Ile Ser Glu Asp Trp Ser Leu His Thr Asp Asp Met
        195                 200                 205

Ile Gly Ser Met
    210

<210> SEQ ID NO 3
<211> LENGTH: 12
<212> TYPE: PRT
<213> ORGANISM: Artificial
<220> FEATURE:
<223> OTHER INFORMATION: Description of artificial sequence: Peptide for
      Immunization

<400> SEQUENCE: 3

Ala Pro Gln Lys Ser Pro Trp Leu Thr Lys Pro Cys
1               5                   10

<210> SEQ ID NO 4
<211> LENGTH: 13
<212> TYPE: PRT
<213> ORGANISM: Artificial
<220> FEATURE:
<223> OTHER INFORMATION: Description of artificial sequence: Peptide for
      Immunization

<400> SEQUENCE: 4

Pro Leu Gln Pro Ser His Phe Leu Asp Ile Ser Glu Asp
1               5                   10

<210> SEQ ID NO 5
<211> LENGTH: 11
<212> TYPE: PRT
<213> ORGANISM: Artificial
<220> FEATURE:
<223> OTHER INFORMATION: Description of artificial sequence: Peptide for
      Immunization

<400> SEQUENCE: 5

Ile Tyr Ser Thr Glu Ile His Tyr Ser Ser Lys
1               5                   10

<210> SEQ ID NO 6
<211> LENGTH: 12
<212> TYPE: PRT
<213> ORGANISM: Artificial
<220> FEATURE:
<223> OTHER INFORMATION: Description of artificial sequence: Peptide for
      Immunization

<400> SEQUENCE: 6

Trp Ser Leu His Thr Asp Asp Met Ile Gly Ser Met
1               5                   10

<210> SEQ ID NO 7
<211> LENGTH: 15
<212> TYPE: PRT
<213> ORGANISM: Artificial
<220> FEATURE:
<223> OTHER INFORMATION: Description of artificial sequence: Peptide for
      Immunization

<400> SEQUENCE: 7

Cys Ser Ile Asp Trp Phe Met Val Thr Val His Pro Phe Met Leu
1               5                   10                  15
```

```
<210> SEQ ID NO 8
<211> LENGTH: 12
<212> TYPE: PRT
<213> ORGANISM: Artificial
<220> FEATURE:
<223> OTHER INFORMATION: Description of artificial sequence: Peptide for
      Immunization

<400> SEQUENCE: 8

Cys Val His Phe His Glu Leu His Leu Gly Leu Gly
1               5                   10

<210> SEQ ID NO 9
<211> LENGTH: 15
<212> TYPE: PRT
<213> ORGANISM: Artificial
<220> FEATURE:
<223> OTHER INFORMATION: Description of artificial sequence: Peptide for
      Immunization

<400> SEQUENCE: 9

Ser Ser Lys Gly Thr Pro Ser Lys Phe Val Ile Pro Val Ser Cys
1               5                   10                  15

<210> SEQ ID NO 10
<211> LENGTH: 13
<212> TYPE: PRT
<213> ORGANISM: Artificial
<220> FEATURE:
<223> OTHER INFORMATION: Description of artificial sequence: Peptide for
      Immunization

<400> SEQUENCE: 10

Val Phe Ser Leu Ser Gln Ser Ser Gln Arg Pro Asn Cys
1               5                   10

<210> SEQ ID NO 11
<211> LENGTH: 21
<212> TYPE: DNA
<213> ORGANISM: Artificial
<220> FEATURE:
<223> OTHER INFORMATION: Description of artificial sequence: siRNA

<400> SEQUENCE: 11
ccaugagagu agccagcaat t                                               21

<210> SEQ ID NO 12
<211> LENGTH: 21
<212> TYPE: DNA
<213> ORGANISM: Artificial
<220> FEATURE:
<223> OTHER INFORMATION: Description of artificial sequence: siRNA

<400> SEQUENCE: 12
uugcuggcua cucucaugga g                                               21

<210> SEQ ID NO 13
<211> LENGTH: 21
<212> TYPE: DNA
<213> ORGANISM: Artificial
<220> FEATURE:
<223> OTHER INFORMATION: Description of artificial sequence: siRNA

<400> SEQUENCE: 13
gguucaggac aaaguccaat t                                               21
```

```
<210> SEQ ID NO 14
<211> LENGTH: 21
<212> TYPE: DNA
<213> ORGANISM: Artificial
<220> FEATURE:
<223> OTHER INFORMATION: Description of artificial sequence: siRNA

<400> SEQUENCE: 14
uuggacuuug uccugaaccg g                                              21

<210> SEQ ID NO 15
<211> LENGTH: 21
<212> TYPE: DNA
<213> ORGANISM: Artificial
<220> FEATURE:
<223> OTHER INFORMATION: Description of artificial sequence:
      Oligonucleotide

<400> SEQUENCE: 15
aaatttggca gctgccttca c                                              21

<210> SEQ ID NO 16
<211> LENGTH: 21
<212> TYPE: DNA
<213> ORGANISM: Artificial
<220> FEATURE:
<223> OTHER INFORMATION: Description of artificial sequence:
      Oligonucleotide

<400> SEQUENCE: 16
tgatgccaca ttcagtaaca c                                              21

<210> SEQ ID NO 17
<211> LENGTH: 326
<212> TYPE: PRT
<213> ORGANISM: Artificial
<220> FEATURE:
<223> OTHER INFORMATION: Description of artificial sequence: Translation
      of PCR product

<400> SEQUENCE: 17

Gly Pro Ser Val Phe Pro Leu Ala Pro Ser Ser Lys Ser Thr Ser Gly
 1               5                  10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Gln Thr Tyr Ile Cys Asn
65                  70                  75                  80

Val Asn His Lys Pro Ser Asn Thr Lys Val Asp Lys Val Glu Pro
                85                  90                  95

Lys Ser Cys Asp Lys Thr His Thr Cys Pro Pro Cys Pro Ala Pro Glu
            100                 105                 110

Leu Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
```

165                 170                 175
Ser Thr Tyr Arg Val Ser Val Leu Thr Val Leu His Gln Asp Trp
            180                 185                 190
Leu Asn Gly Lys Glu Tyr Lys Cys Lys Val Ser Asn Lys Ala Leu Pro
        195                 200                 205
Ala Pro Ile Glu Lys Thr Ile Ser Lys Ala Lys Gly Gln Pro Arg Glu
    210                 215                 220
Pro Gln Val Tyr Thr Leu Pro Pro Ser Arg Asp Glu Leu Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Val Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
            325

<210> SEQ ID NO 18
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 18

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 19
<211> LENGTH: 324
<212> TYPE: DNA
<213> ORGANISM: Artificial
<220> FEATURE:
<223> OTHER INFORMATION: Description of artificial sequence: PCR product

<400> SEQUENCE: 19
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180

```
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttag                                           324
```

<210> SEQ ID NO 20
<211> LENGTH: 981
<212> TYPE: DNA
<213> ORGANISM: Artificial
<220> FEATURE:
<223> OTHER INFORMATION: Description of artificial sequence: PCR product

<400> SEQUENCE: 20

```
ggcccatcgg tcttcccct ggcaccctcc tccaagagca cctctggggg cacagcggcc     60
ctgggctgcc tggtcaagga ctacttcccc gaaccggtga cggtgtcgtg gaactcaggc    120
gccctgacca gcggcgtgca caccttcccg gctgtcctac agtcctcagg actctactcc    180
ctcagcagcg tggtgaccgt gccctccagc agcttgggca cccagaccta catctgcaac    240
gtgaatcaca agcccagcaa caccaaggtg gacaagaaag ttgagcccaa atcttgtgac    300
aaaactcaca catgcccacc gtgcccagca cctgaactcc tggggggacc gtcagtcttc    360 ctcttcccc caaaacccaa ggacaccctc atgatctccc ggacccctga ggtcacatgc     420
gtggtggtgg acgtgagcca cgaagaccct gaggtcaagt tcaactggta cgtggacggc    480
gtggaggtgc ataatgccaa gacaaagccg cgggaggagc agtacaacag cacgtaccgt    540
gtggtcagcg tcctcaccgt cctgcaccag gactggctga atggcaagga gtacaagtgc    600
aaggtctcca acaaagccct cccagccccc atcgagaaaa ccatctccaa agccaaaggg    660
cagccccgag aaccacaggt gtacaccctg cccccatccc gggatgagct gaccaagaac    720
caggtcagcc tgacctgcct ggtcaaaggc ttctatccca gcgacatcgc cgtggagtgg    780
gagagcaatg ggcagccgga gaacaactac aagaccacgc ctcccgtgct ggactccgac    840
ggctccttct tcctctatag caagctcacc gtggacaaga gcaggtggca gcaggggaac    900
gtcttctcat gctccgtgat gcatgaggct ctgcacaacc actacacgca gaagagcctc    960
tccctgtctc cgggtaaatg a                                              981
```

<210> SEQ ID NO 21
<211> LENGTH: 324
<212> TYPE: DNA
<213> ORGANISM: Artificial
<220> FEATURE:
<223> OTHER INFORMATION: Description of artificial sequence: codon
      optimized nucleic acid

<400> SEQUENCE: 21

```
cgtacggtgg ccgctcccag cgtgttcatc ttcccccca gcgacgagca gctgaagtcc     60
ggcaccgcca gcgtggtgtg cctgctgaac aacttctacc ccggggaggc caaggtgcag    120
tggaaggtgg acaacgccct gcagagcggc aacagccagg agagcgtcac cgagcaggac    180
agcaaggact ccacctacag cctgagcagc accctgaccc tgagcaaggc cgactacgag    240
aagcacaagg tgtacgcctg cgaggtgacc caccagggcc tgtccagccc cgtgaccaag    300
agcttcaaca ggggcgagtg ctag                                           324
```

<210> SEQ ID NO 22
<211> LENGTH: 107
<212> TYPE: PRT
<213> ORGANISM: Artificial

<220> FEATURE:
<223> OTHER INFORMATION: Description of artificial sequence: codon
      optimized protein

<400> SEQUENCE: 22

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 23
<211> LENGTH: 981
<212> TYPE: DNA
<213> ORGANISM: Artificial
<220> FEATURE:
<223> OTHER INFORMATION: Description of artificial sequence: codon
      optimized nucleic acid

<400> SEQUENCE: 23
ggcccaagcg tgttcccct  ggccccagc  agcaagagca ccagcggcgg cacagccgcc      60
ctgggctgcc tggtgaagga ctacttcccc gagcccgtga ccgtgagctg gaacagcgga     120
gccctgacct ccggcgtgca caccttcccc gccgtgctgc agagcagcgg cctgtacagc     180
ctgagcagcg tggtgaccgt gcccagcagc agcctgggca cccagaccta catctgcaac     240
gtgaaccaca agcccagcaa caccaaggtg gacaagagag tggagcccaa gagctgcgac     300
aagacccaca cctgcccccc ctgcccagcc ccagagctgc tgggcggacc cagcgtgttc     360
ctgttccccc ccaagcccaa ggacaccctg atgatcagca ggacccccga ggtgacctgc     420
gtggtggtgg acgtgagcca cgaggaccca gaggtgaagt tcaactggta cgtggacggc     480
gtggaggtgc acaacgccaa gaccaagccc agagaggagc agtacaacag cacctacagg     540
gtggtgtccg tgctgaccgt gctgcaccag gactggctga acggcaagga atacaagtgc     600
aaggtctcca acaaggccct gccagccccc atcgaaaaga ccatcagcaa ggccaagggc     660
cagccacggg agccccaggt gtacaccctg ccccccagcc gggaggagat gaccaagaac     720
caggtgtccc tgacctgtct ggtgaagggc ttctacccca gcgacatcgc cgtggagtgg     780
gagagcaacg gccagcccga gaacaactac aagaccaccc ccccagtgct ggacagcgac     840
ggcagcttct tcctgtacag caagctgacc gtggacaagt ccaggtggca gcagggcaac     900
gtgttcagct gcagcgtgat gcacgaggcc ctgcacaacc actacaccca gaagtccctg     960
agcctgagcc ccggcaagta g                                               981

<210> SEQ ID NO 24
<211> LENGTH: 326
<212> TYPE: PRT
<213> ORGANISM: Artificial
<220> FEATURE:
<223> OTHER INFORMATION: Description of artificial sequence: codon optimized protein

<400> SEQUENCE: 24

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Gln Thr Tyr Ile Cys Asn
65                  70                  75                  80

Val Asn His Lys Pro Ser Asn Thr Lys Val Asp Lys Arg Val Glu Pro
                85                  90                  95

Lys Ser Cys Asp Lys Thr His Thr Cys Pro Pro Cys Pro Ala Pro Glu
            100                 105                 110

Leu Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 25
<211> LENGTH: 21
<212> TYPE: DNA
<213> ORGANISM: Artificial
<220> FEATURE:
<223> OTHER INFORMATION: Description of artificial sequence:
      Oligonucleotide

<400> SEQUENCE: 25
tgacactggc aaaacaatgc a                                         21

<210> SEQ ID NO 26
<211> LENGTH: 21
<212> TYPE: DNA
<213> ORGANISM: Artificial
<220> FEATURE:
<223> OTHER INFORMATION: Description of artificial sequence:
      Oligonucleotide

<400> SEQUENCE: 26 ggtcctttc accagcaagc t                                           21

<210> SEQ ID NO 27
<211> LENGTH: 21
<212> TYPE: DNA
<213> ORGANISM: Artificial
<220> FEATURE:
<223> OTHER INFORMATION: Description of artificial sequence: siRNA

<400> SEQUENCE: 27
uaacuguaua aucgacuagt t                                          21

<210> SEQ ID NO 28
<211> LENGTH: 21
<212> TYPE: DNA
<213> ORGANISM: Artificial
<220> FEATURE:
<223> OTHER INFORMATION: Description of artificial sequence: siRNA

<400> SEQUENCE: 28
cuagucgauu auacaguuag a                                          21

<210> SEQ ID NO 29
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 29

Met Lys Val Phe Lys Phe Ile Gly Leu Met Ile Leu Leu Thr Ser
1               5                   10                  15

<210> SEQ ID NO 30
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 30

Lys Phe Ile Gly Leu Met Ile Leu Leu Thr Ser Ala Phe Ser Ala
1               5                   10                  15

<210> SEQ ID NO 31
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 31

Leu Met Ile Leu Leu Thr Ser Ala Phe Ser Ala Gly Ser Gly Gln
1               5                   10                  15

```
<210> SEQ ID NO 32
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 32

Leu Thr Ser Ala Phe Ser Ala Gly Ser Gly Gln Ser Pro Met Thr
1               5                   10                  15

<210> SEQ ID NO 33
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 33

Phe Ser Ala Gly Ser Gly Gln Ser Pro Met Thr Val Leu Cys Ser
1               5                   10                  15

<210> SEQ ID NO 34
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 34

Ser Gly Gln Ser Pro Met Thr Val Leu Cys Ser Ile Asp Trp Phe
1               5                   10                  15

<210> SEQ ID NO 35
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 35

Pro Met Thr Val Leu Cys Ser Ile Asp Trp Phe Met Val Thr Val
1               5                   10                  15

<210> SEQ ID NO 36
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 36

Leu Cys Ser Ile Asp Trp Phe Met Val Thr Val His Pro Phe Met
1               5                   10                  15

<210> SEQ ID NO 37
<211> LENGTH: 15
<212> TYPE: PRT
<213> ORGANISM: Artificial
<220> FEATURE:
<223> OTHER INFORMATION: Description of artificial sequence: Peptide for
      Screening
```

<400> SEQUENCE: 37

Asp Trp Phe Met Val Thr Val His Pro Phe Met Leu Asn Asn Asp
1               5                   10                  15

<210> SEQ ID NO 38
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 38

Val Thr Val His Pro Phe Met Leu Asn Asn Asp Val Cys Val His
1               5                   10                  15

<210> SEQ ID NO 39
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 39

Pro Phe Met Leu Asn Asn Asp Val Cys Val His Phe His Glu Leu
1               5                   10                  15

<210> SEQ ID NO 40
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 40

Asn Asn Asp Val Cys Val His Phe His Glu Leu His Leu Gly Leu
1               5                   10                  15

<210> SEQ ID NO 41
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 41

Cys Val His Phe His Glu Leu His Leu Gly Leu Gly Cys Pro Pro
1               5                   10                  15

<210> SEQ ID NO 42
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 42

His Glu Leu His Leu Gly Leu Gly Cys Pro Pro Asn His Val Gln
1               5                   10                  15

<210> SEQ ID NO 43
<211> LENGTH: 15

```
<212> TYPE: PRT
<213> ORGANISM: Artificial
<220> FEATURE:
<223> OTHER INFORMATION: Description of artificial sequence: Peptide for
      Screening

<400> SEQUENCE: 43

Leu Gly Leu Gly Cys Pro Pro Asn His Val Gln Pro His Ala Tyr
1               5                   10                  15

<210> SEQ ID NO 44
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 44

Cys Pro Pro Asn His Val Gln Pro His Ala Tyr Gln Phe Thr Tyr
1               5                   10                  15

<210> SEQ ID NO 45
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 45

His Val Gln Pro His Ala Tyr Gln Phe Thr Tyr Arg Val Thr Glu
1               5                   10                  15

<210> SEQ ID NO 46
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 46

His Ala Tyr Gln Phe Thr Tyr Arg Val Thr Glu Cys Gly Ile Arg
1               5                   10                  15

<210> SEQ ID NO 47
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 47

Phe Thr Tyr Arg Val Thr Glu Cys Gly Ile Arg Ala Lys Ala Val
1               5                   10                  15

<210> SEQ ID NO 48
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 48

Val Thr Glu Cys Gly Ile Arg Ala Lys Ala Val Ser Gln Asp Met
```

<210> SEQ ID NO 49
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 49

Gly Ile Arg Ala Lys Ala Val Ser Gln Asp Met Val Ile Tyr Ser
1               5                   10                  15

<210> SEQ ID NO 50
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 50

Lys Ala Val Ser Gln Asp Met Val Ile Tyr Ser Thr Glu Ile His
1               5                   10                  15

<210> SEQ ID NO 51
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 51

Gln Asp Met Val Ile Tyr Ser Thr Glu Ile His Tyr Ser Ser Lys
1               5                   10                  15

<210> SEQ ID NO 52
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 52

Ile Tyr Ser Thr Glu Ile His Tyr Ser Ser Lys Gly Thr Pro Ser
1               5                   10                  15

<210> SEQ ID NO 53
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 53

Glu Ile His Tyr Ser Ser Lys Gly Thr Pro Ser Lys Phe Val Ile
1               5                   10                  15

<210> SEQ ID NO 54
<211> LENGTH: 15
<212> TYPE: PRT
<213> ORGANISM: Artificial
<220> FEATURE:
<223> OTHER INFORMATION: Description of artificial sequence: Peptide for Screening

<400> SEQUENCE: 54

Ser Ser Lys Gly Thr Pro Ser Lys Phe Val Ile Pro Val Ser Cys
1               5                   10                  15

<210> SEQ ID NO 55
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 55

Thr Pro Ser Lys Phe Val Ile Pro Val Ser Cys Ala Ala Pro Gln
1               5                   10                  15

<210> SEQ ID NO 56
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 56

Phe Val Ile Pro Val Ser Cys Ala Ala Pro Gln Lys Ser Pro Trp
1               5                   10                  15

<210> SEQ ID NO 57
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 57

Val Ser Cys Ala Ala Pro Gln Lys Ser Pro Trp Leu Thr Lys Pro
1               5                   10                  15

<210> SEQ ID NO 58
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 58

Ala Pro Gln Lys Ser Pro Trp Leu Thr Lys Pro Cys Ser Met Arg
1               5                   10                  15

<210> SEQ ID NO 59
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 59

Ser Pro Trp Leu Thr Lys Pro Cys Ser Met Arg Val Ala Ser Lys
1               5                   10                  15

<210> SEQ ID NO 60

```
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 60

Thr Lys Pro Cys Ser Met Arg Val Ala Ser Lys Ser Arg Ala Thr
1               5                   10                  15

<210> SEQ ID NO 61
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 61

Ser Met Arg Val Ala Ser Lys Ser Arg Ala Thr Ala Gln Lys Asp
1               5                   10                  15

<210> SEQ ID NO 62
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 62

Ala Ser Lys Ser Arg Ala Thr Ala Gln Lys Asp Glu Lys Cys Tyr
1               5                   10                  15

<210> SEQ ID NO 63
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 63

Arg Ala Thr Ala Gln Lys Asp Glu Lys Cys Tyr Glu Val Phe Ser
1               5                   10                  15

<210> SEQ ID NO 64
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 64

Gln Lys Asp Glu Lys Cys Tyr Glu Val Phe Ser Leu Ser Gln Ser
1               5                   10                  15

<210> SEQ ID NO 65
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 65
```

-continued

Lys Cys Tyr Glu Val Phe Ser Leu Ser Gln Ser Ser Gln Arg Pro
1               5                   10                  15

<210> SEQ ID NO 66
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 66

Val Phe Ser Leu Ser Gln Ser Ser Gln Arg Pro Asn Cys Asp Cys
1               5                   10                  15

<210> SEQ ID NO 67
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 67

Ser Gln Ser Ser Gln Arg Pro Asn Cys Asp Cys Pro Pro Cys Val
1               5                   10                  15

<210> SEQ ID NO 68
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 68

Gln Arg Pro Asn Cys Asp Cys Pro Pro Cys Val Phe Ser Glu Glu
1               5                   10                  15

<210> SEQ ID NO 69
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 69

Cys Asp Cys Pro Pro Cys Val Phe Ser Glu Glu Glu His Thr Gln
1               5                   10                  15

<210> SEQ ID NO 70
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 70

Pro Cys Val Phe Ser Glu Glu Glu His Thr Gln Val Pro Cys His
1               5                   10                  15

<210> SEQ ID NO 71
<211> LENGTH: 15
<212> TYPE: PRT
<213> ORGANISM: Artificial
<220> FEATURE:

```
<223> OTHER INFORMATION: Description of artificial sequence: Peptide for
      Screening

<400> SEQUENCE: 71

Ser Glu Glu Glu His Thr Gln Val Pro Cys His Gln Ala Gly Ala
1               5                   10                  15

<210> SEQ ID NO 72
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 72

His Thr Gln Val Pro Cys His Gln Ala Gly Ala Gln Glu Ala Gln
1               5                   10                  15

<210> SEQ ID NO 73
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 73

Pro Cys His Gln Ala Gly Ala Gln Glu Ala Gln Pro Leu Gln Pro
1               5                   10                  15

<210> SEQ ID NO 74
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 74

Ala Gly Ala Gln Glu Ala Gln Pro Leu Gln Pro Ser His Phe Leu
1               5                   10                  15

<210> SEQ ID NO 75
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 75

Glu Ala Gln Pro Leu Gln Pro Ser His Phe Leu Asp Ile Ser Glu
1               5                   10                  15

<210> SEQ ID NO 76
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 76

Leu Gln Pro Ser His Phe Leu Asp Ile Ser Glu Asp Trp Ser Leu
1               5                   10                  15
```

```
<210> SEQ ID NO 77
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 77

His Phe Leu Asp Ile Ser Glu Asp Trp Ser Leu His Thr Asp Asp
1               5                   10                  15

<210> SEQ ID NO 78
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 78

Ile Ser Glu Asp Trp Ser Leu His Thr Asp Asp Met Ile Gly Ser
1               5                   10                  15

<210> SEQ ID NO 79
<211> LENGTH: 15
<212> TYPE: PRT
<213> ORGANISM: Artificial
<220> FEATURE:
<223> OTHER INFORMATION: Description of artificial sequence: Peptide for
      Screening

<400> SEQUENCE: 79

Ser Glu Asp Trp Ser Leu His Thr Asp Asp Met Ile Gly Ser Met
1               5                   10                  15
```

MONOCLONAL ANTIBODIES FOR TREATMENT OF CANCER

This application is a continuation application of U.S. patent application Ser. No. 13/710,828, filed Dec. 11, 2012, (now issued as U.S. Pat. No. 8,961,980) which is a divisional application of U.S. patent application Ser. No. 12/531,267, filed Sep. 14, 2009, (now issued as U.S. Pat. No. 8,354,104) which is a National Stage Entry of PCT/EP08/02063, which was filed on Mar. 14, 2008, which claims benefit of U.S. Provisional Application Ser. No. 60/894,860, filed Mar. 14, 2007, and which claims priority to European Patent Application No. 07005258.4, which was filed on Mar. 14, 2007, all of which are incorporated herein by reference in their entireties.

Antibody based cancer therapies have been successfully introduced into the clinic and have emerged as the most promising therapeutics in oncology over the last decade.

Antibody-based therapies for cancer have the potential of higher specificity and lower side effect profile as compared to conventional drugs. The reason is a precise distinction between normal and neoplastic cells by antibodies and the fact that their mode of action relies on less toxic immunological anti-tumor mechanisms, such as complement activation and recruitment of cytotoxic immune cells.

Targets for antibody-based therapies need to have particular qualities, which form the basis for proper discrimination between normal and neoplastic cells. Obviously, a target with either exclusive restriction to tumor cells and entirely undetectable on normal tissues is ideal for the development of efficient and safe antibody therapeutics. In another aspect, a high-level overexpression may be the basis for the therapeutic window and low side effects exemplified by the human epidermal growth factor receptor type 2 (HER-2), which as a result of gene amplification is a good target for the antibody trastuzumab (Herceptin).

Other targets for antibodies which are either already approved or in clinical development for tumor therapy have distinct qualities, which are not based on a numeric overexpression of target molecules on tumor cells. In the case of antibodies to the proteoglycan MUC-1, a peptide repeat epitope in the backbone of the target is underglycosylated in tumor cells and thus altered to its normal counterpart. In the case of antibodies to CD20 (rituximab), CD52 (Campath-1H) and CD22 (epratuzumab), antibody targets have comparable expression levels on tumor cells and normal lymphocytes. Here, the ablation of normal cells by the antibody is tolerable since target-negative stem cells restore the normal lymphocyte repertoire. Other examples of differential accessibility of antibody targets are carcinoembryonal antigen (CEA) and carboanhydrase IX (CA9). Both antigens are expressed on normal epithelia of colon and kidney, respectively. However, radioactively labeled imaging antibodies do distinguish well between tumor and normal tissue, and cytotoxic antibodies are well tolerated. This is most likely due to a restricted expression of CA9 and CEA on the luminal side of normal epithelial tissue where IgG antibodies do not have access. Also antigen epithelial cell adhesion molecule (Ep-CAM) belongs to this category. As a homotypic cell adhesion molecule for epithelial cells it is localized in the intercellular space. Intriguingly, whereas high-affinity anti-Ep-CAM antibodies are very toxic, intermediate-affinity antibodies are well tolerated. This suggests accessibility of the Ep-CAM target on normal cells but also indicates that kinetics of antibody binding may open a therapeutic window.

Eight antibodies have been approved for treatment of neoplastic diseases, most of them, however in lymphoma and leukemia (Adams, G. P. & Weiner, L. M. (2005) *Nat. Biotechnol.* 23, 1147-1157). Only three mAbs, namely Herceptin, Avastin and Erbitux, address solid cancer types, which account for more than 90% of cancer-evoked mortality. The substantial remaining medical need, the significant clinical benefit approved mAbs have already provided and their considerable commercial success altogether motivated a wave of innovative approaches standing poised not only to develop antibody-based therapies for extended groups of patients but also to improve their efficacy (Brekke, O. H. & Sandlie, I. (2003) *Nat. Rev. Drug Discov.* 2, 52-62; Carter, P. (2001) *Nat. Rev. Cancer* 1, 118-129).

One of the challenges to be mastered for the advent of the next generation of upgraded antibody-based cancer therapeutics is the selection of appropriate target molecules, which is the key for a favorable toxicity/efficacy profile.

Current antibodies available for the treatment of solid cancers owing to the expression of their targets on normal tissues do not sufficiently exploit the cumulative power of action modes embedded in antibody molecules. Her2/neu, for instance, the target of Herceptin, is expressed in many normal human tissues including heart muscle (Crone, S. A., Zhao, Y. Y., Fan, L., Gu, Y., Minamisawa, S., Liu, Y., Peterson, K. L., Chen, J., Kahn, R., Condorelli, G. et al. (2002) *Nat. Med.* 8, 459-465). As a consequence, Herceptin was designed with a reduced immunological potency and cannot be given at the maximum effective dose, because of otherwise unacceptable toxicity. This "blunting of a potentially sharp knife" limits the therapeutic efficacy of Herceptin.

In addition to lack of expression in toxicity relevant normal tissues, robust and high expression on the surface of tumor cells and exhibition of a tumor promoting function are desirable characteristics for an ideal antibody target (Houshmand, P. & Zlotnik, A. (2003) *Curr. Opin. Cell Biol.* 15, 640-644).

Using an integrated data mining and experimental validation approach for the discovery of new targets for antibody therapy of cancer we identified GT468. GT468 is a placenta-specific gene with no detectable expression in any other normal human tissue. However, it is frequently aberrantly activated and highly expressed in a variety of tumor types, in particular breast cancer. RNAi-mediated silencing of GT468 in MCF-7 and BT-549 breast cancer cells profoundly impairs motility, migration and invasion and induces a G1/S cell cycle block with nearly complete abrogation of proliferation. Knock down of GT468 is associated with decreased expression of cyclin D1 and reduced phosphorylation of AKT kinase. Moreover, GT468 is localized on the surface of cancer cells and is accessible for antibodies which antagonize biological functions of this molecule.

GT468 has several properties that make it a highly attractive target for therapeutic antibodies. Being a differentiation antigen of a cell lineage which appears in the human body only in such an exceptional state as pregnancy, it is as absent from healthy toxicity-relevant tissues as a self-antigen can possibly be. Its high prevalence in a variety of tumor entities would make a broad number of patients eligible for treatment with GT468 targeting therapies. In the case of breast cancer for example, 82% of patients carry this target. Her2/neu, in contrast, the target of Herceptin, the only mAb available for treatment of this cancer type, is overexpressed in only 20-25% of breast cancer patients (Slamon, D. J., Godolphin, W., Jones, L. A., Holt, J. A., Wong, S. G., Keith, D. E., Levin, W. J., Stuart, S. G., Udove, J., Ullrich, A. et al. (1989) *Science* 244, 707-712). For lung cancer and for gastric cancer, in which GT468 is expressed in 42 and 58% of the cases respectively, there is no approved mAB treatment so far owing to the lack of appropriate targets in these cancer types.

GT468 is drugable by antibodies on living cells and such antibodies may precipitate anti-tumoral effects such as proliferation inhibition. GT468 is involved not only in proliferation but also cell motility, migration and invasion. Most interestingly, all these attributes do not only substantially contribute to the tumor phenotype but are also inherent properties of the human trophoblast, which physiological characteristics are to grow fast and to invade efficiently into uterus tissue. It is expected that mAbs against GT468 can be engineered, which intervene with all these functions at once on top of their potential to mediate immune effector functions such as ADCC and CDC.

SUMMARY OF THE INVENTION

The present invention generally provides antibodies useful as therapeutics for treating and/or preventing diseases associated with cells expressing GT468 and/or being characterized by association of GT468 with their cell surface, including tumor-related diseases such as cancer, in particular breast cancer, lung cancer, gastric cancer, ovarian cancer, hepatocellular cancer, colon cancer, pancreatic cancer, esophageal cancer, head & neck cancer, kidney cancer, prostate cancer and liver cancer.

In one aspect the invention relates to an antibody having the ability of binding to GT468. Preferably, the antibody has the ability of binding to GT468 located on the cell surface and preferably binds to one or more epitopes located within the extracellular domain of GT468, preferably within amino acid residues 23-212 of GT468, and most preferably binds to an epitope located within one of the amino acid sequences of SEQ ID Nos: 3-10 and 35-79. In one preferred embodiment, the antibody is specific for one or more of the amino acid sequences of SEQ ID NOs: 3-10 and 35-79. In various embodiments, the antibody has the ability of binding to a peptide comprising amino acids 29 to 119, preferably amino acids 29 to to 212 and more preferably amino acids 23 to 212 of SEQ ID NO: 2. Preferably, the antibody binds to cancer cells, in particular cells of the cancer types mentioned above and, preferably, does not bind substantially to non-cancerous cells. Preferably, binding of said antibody to cells expressing GT468 and/or being characterized by association of GT468 with their cell surface such as cancer cells mediates killing of said cells and/or inhibits one or more activities of such cells such as motility, migration, invasion and proliferation. Preferably, the antibody mediates killing of said cells and/or inhibits proliferation of said cells.

Killing of cells and/or inhibition of one or more activities of cells, in particular cell proliferation, by the antibody of the invention is preferably induced by binding of the antibody to GT468 expressed by said cells and/or being associated with the cell surface of said cells. Such killing of cells and/or inhibition of one or more activities of cells can be utilized therapeutically as described herein. In particular, killing of cells and/or inhibition of proliferation of cells can be utilized for treating or preventing cancer. Inhibition of motility, migration, invasion and/or proliferation of cells can be utilized for treating or preventing cancer, in particular cancer metastasis and the metastatic spread of cancer cells.

The cells expressing GT468 and/or being characterized by association of GT468 with their cell surface are preferably cancer cells and are, in particular, selected from the group consisting of tumorigenic breast, lung, gastric, ovarian, liver, colon, pancreatic, esophageal, head-neck, renal and prostate cancer cells.

Preferably the antibody of the invention mediates killing of cells by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis.

In one embodiment the antibody of the invention does not induce CDC mediated lysis of cells.

Preferably, ADCC mediated lysis of cells takes place in the presence of effector cells, which in particular embodiments are selected from the group consisting of monocytes, mononuclear cells, NK cells and PMNs, and phagocytosis is by macrophages.

The antibody of the invention may be a monoclonal, chimeric, human, or humanized antibody, or a fragment of an antibody and may be selected from the group consisting of an IgG1, an IgG2, preferably IgG2a and IgG2b, an IgG3, an IgG4, an IgM, an IgA1, an IgA2, a secretory IgA, an IgD, and an IgE antibody.

According to all aspects of the invention, GT468 is preferably human GT468, preferably having the amino acid sequence according to SEQ ID NO: 2, more preferably having the amino acid sequence of the extracellular domain of the amino acid sequence according to SEQ ID NO: 2, in particular having the amino acid sequence spanning from amino acids 23 to 212 of SEQ ID NO: 2.

In particular preferred embodiments, the antibody of the invention binds to native epitopes of GT468 present on the surface of living cells such as those of SEQ ID NOs: 3-10 and 35-79. In further preferred embodiments, the antibody of the invention is specific for cancer cells, preferably breast cancer cells.

In certain embodiments of the invention, GT468 is expressed on and/or associated with the surface of cells.

Antibodies of the invention may be obtained by a method comprising the step of immunizing an animal with a protein or peptide having an amino acid sequence selected from the group consisting of SEQ ID NOs: 2-10 and 35-79, or an immunogenic fragment or derivative thereof, or a nucleic acid or host cell expressing said protein or peptide, or immunogenic fragment or derivative thereof. Preferably, an antibody of the invention is specific for the afore mentioned proteins, peptides or immunogenic fragments or derivatives thereof. In the context of a protein or peptide used in immunization a derivative relates to a variant of such protein or peptide which has the same immunogenic properties as the protein or peptide from which it is derived. In particular, the derivative of a protein or peptide when used in immunization for the production of antibodies, in particular monoclonal antibodies, provides antibodies having the same specificity as antibodies obtained when using the protein or peptide in immunization. For example, such derivative may include the deletion, substitution or addition of one or more amino acids. In particular, it may include the addition of one or more amino acids such as cysteine at either the N-terminus or C-terminus or both.

In a particularly preferred embodiment, the antibody of the invention is produced by a clone having the accession no. DSM ACC2822 (4E9-1H9), DSM ACC2826 (9B6-2A9), DSM ACC2824 (59D6-2F2), DSM ACC2825 (61C11-2B5), DSM ACC2823 (78H11-1H6), DSM ACCXXXX (22-1A-1), DSM ACCXXXX (22-2A-1), DSM ACCXXXX(22-9B-1), DSM ACCXXXX (23-33A-1), DSM ACCXXXX (23-

19A-1), DSM ACCXXXX (F11#33F7D12), DSM ACCXXXX (4A12 2D4 1A10), or DSM ACCXXXX (4E9 1D12 2D4).

In one embodiment the antibody of the invention is coupled to a therapeutic agent such as a toxin, a radioisotope, a drug or a cytotoxic agent.

In a further aspect the invention relates to a hybridoma capable of producing the antibody of the invention. Preferred hybridomas are those having the accession no. DSM ACC2822 (4E9-1H9), DSM ACC2826 (9B6-2A9), DSM ACC2824 (59D6-2F2), DSM ACC2825 (61C11-2B5), DSM ACC2823 (781111-1H6), DSM ACCXXXX (22-1A-1), DSM ACCXXXX (22-2A-1), DSM ACCXXXX (22-9B-1), DSM ACCXXXX (23-33A-1), DSM ACCXXXX (23-19A-1), DSM ACCXXXX (F11#33F7D12), DSM ACCXXXX (4A12 2D4 1A10), or DSM ACCXXXX (4E9 1D12 2D4).

Antibodies of the invention are designated herein by referring to the designation of the antibody and/or by referring to the clone producing the antibody, e.g. 4E9-1H9.

The invention also relates to a pharmaceutical composition comprising an antibody of the invention and/or a conjugate thereof with a therapeutic agent, and a pharmaceutically acceptable carrier.

In a further aspect the invention relates to a method of inhibiting one or more activities selected from motility, migration, invasion and growth, preferably growth and/or killing of a cell expressing GT468 and/or being characterized by association of GT468 with its cell surface, comprising contacting the cell with an effective amount of an antibody of the invention and/or a conjugate thereof with a therapeutic agent. GT468 is preferably expressed on the surface of said cell.

In a further aspect the invention relates to a method of treating or preventing a disease or disorder involving cells expressing GT468 and/or being characterized by association of GT468 with their cell surface comprising administering to a subject an antibody of the invention, a conjugate thereof with a therapeutic agent, or a pharmaceutical composition comprising the antibody of the invention or the conjugate thereof with a therapeutic agent. Preferably the disease or disorder is a tumor-related disease and in particular embodiments is selected from the group consisting of breast cancer, lung cancer, gastric cancer, ovarian cancer, hepatocellular cancer, colon cancer, pancreatic cancer, esophageal cancer, head & neck cancer, kidney cancer, prostate cancer and liver cancer. GT468 is preferably expressed on the surface of said cells.

Preferably, the antibodies of the invention have the ability to discriminate GT468-variants expressed by different cell types including cancer cells and non-malignant cells.

The term "binding" according to the invention preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant $K_D$) for the target to which the agent binds specifically is more than 10-fold, preferably more than 20-fold, more preferably more than 50-fold, even more preferably more than 100-fold, 200-fold, 500-fold or 1000-fold lower than the dissociation constant ($K_D$) for the target to which the agent does not bind specifically.

The antibodies of the invention preferably mediate killing of cells expressing GT468 and/or being characterized by association of GT468 with their cell surface by binding to GT468. Preferably GT468 is expressed on the surface of said cells. In one embodiment, antibodies of the invention induce complement dependent cytotoxicity (CDC), e.g. at least about 20-40% CDC mediated lysis, preferably about 40-50% CDC mediated lysis, and more preferably more than 50% CDC mediated lysis of cells expressing GT468 and/or being characterized by association of GT468 with their cell surface. Alternatively or in addition to inducing CDC, antibodies of the invention may induce antibody dependent cellular cytotoxicity (ADCC) of cells expressing GT468 and/or being characterized by association of GT468 with their cell surface in the presence of effector cells (e.g., monocytes, mononuclear cells, NK cells and PMNs). Antibodies of the invention may have the ability to induce apoptosis of cells expressing GT468 and/or being characterized by association of GT468 with their cell surface, induce homotypic adhesion of cells expressing GT468 and/or being characterized by association of GT468 with their cell surface and/or induce phagocytosis of cells expressing GT468 and/or being characterized by association of GT468 with their cell surface in the presence of macrophages. The antibodies of the invention may have one or more of the above described functional properties. Preferably, antibodies of the invention induce CDC mediated lysis and ADCC mediated lysis of cells expressing GT468 and/or being characterized by association of GT468 with their cell surface and more preferably induce ADCC mediated lysis of cells expressing GT468 and/or being characterized by association of GT468 with their cell surface while they do not induce CDC mediated lysis of said cells. Exemplary target cells for antibodies of the present invention include, but are not limited to, cancer cells expressing GT468 and/or being characterized by association of GT468 with their cell surface such as tumorigenic breast, lung, gastric, ovarian and hepatocellular cancer cells. In a particular preferred embodiment, killing of cells mediated by antibodies of the invention is GT468 specific, i.e. antibodies of the invention mediate killing, preferably CDC and/or ADCC mediated lysis, of cells expressing GT468 and/or being characterized by association of GT468 with their cell surface but do not mediate killing of cells not expressing GT468 and/or not being characterized by association of GT468 with their cell surface. The antibodies described above may be used to mediate killing of tumor cells in the treatment or prevention of cancer such as breast cancer, lung cancer, gastric cancer, ovarian cancer, hepatocellular cancer, colon cancer, pancreatic cancer, esophageal cancer, head & neck cancer, kidney cancer, prostate cancer and liver cancer.

Antibodies of the invention may be derived from different species, including but not limited to mouse, rat, rabbit, guinea pig and human. Antibodies of the invention also include chimeric molecules in which an antibody constant region derived from one species, preferably human, is combined with the antigen binding site derived from another species. Moreover antibodies of the invention include humanized molecules in which the antigen binding sites of an antibody derived from a non-human species are combined with constant and framework regions of human origin.

Antibodies of the invention include polyclonal and monoclonal antibodies and include IgG2a (e.g. IgG2a, κ, λ), IgG2b (e.g. IgG2b, κ, λ), IgG3 (e.g. IgG3, κ, λ) and IgM antibodies. However, other antibody isotypes are also encompassed by the invention, including IgG1, IgA1, IgA2, secretory IgA, IgD, and IgE antibodies. The antibodies can be whole antibodies or antigen-binding fragments thereof including, for example, Fab, F(ab')$_2$, Fv, single chain Fv fragments or bispecific antibodies. Furthermore, the antigen-binding fragments include binding-domain immunoglobulin fusion proteins comprising (i) a binding domain polypeptide (such as a heavy chain variable region or a light chain variable region) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. Such binding-domain immunoglobulin fusion proteins are further disclosed in US2003/0118592 and US 2003/0133939.

Antibodies of the present invention preferably dissociate from GT468 with a dissociation equilibrium constant (KD) of approximately 1-100 nM or less. Preferably, antibodies of the invention do not cross-react with related cell-surface antigens and thus do not inhibit their function.

In preferred embodiments, antibodies of the present invention can be characterized by one or more of the following properties:
a) specificity for GT468;
b) a binding affinity to GT468 of about 100 nM or less, preferably, about 5-10 nM or less and, more preferably, about 1-3 nM or less,
c) the ability to mediate a high level of CDC on either CD55/59 negative or CD55/59 positive cells;
d) the ability to inhibit the growth of cells which express GT468 and/or are characterized by association of GT468 with their cell surface;
e) the ability to induce apoptosis of cells which express GT468 and/or are characterized by association of GT468 with their cell surface;
f) the ability to induce homotypic adhesion of cells which express GT468 and/or are characterized by association of GT468 with their cell surface;
g) the ability to induce ADCC of cells which express GT468 and/or are characterized by association of GT468 with their cell surface in the presence of effector cells;
h) the ability to prolong survival of a subject having tumor cells which express GT468 and/or are characterized by association of GT468 with their cell surface;
i) the ability to deplete cells which express GT468 and/or are characterized by association of GT468 with their cell surface;
j) the ability to deplete cells which express low levels of GT468 and/or are characterized by association of GT468 with their cell surface and/or
k) the ability to aggregate GT468 on the surface of living cells The anti-GT468 antibodies of the present invention can be derivatized, linked to or co-expressed to other binding specificities. In a particular embodiment, the invention provides a bispecific or multispecific molecule comprising at least one first binding specificity for GT468 (e.g., an anti-GT468 antibody or mimetic thereof), and a second binding specificity for a effector cell, such as a binding specificity for an Fc receptor (e.g., a Fc-gamma receptor, such as Fc-gamma RI, or any other Fc receptor) or a T cell receptor, e.g., CD3.

Accordingly, the present invention includes bispecific and multispecific molecules that bind to both GT468 and to an Fc receptor or a T cell receptor, e.g. CD3. Examples of Fc receptors are IgG receptor, Fc-gamma receptor (FcγR), such as FcγRI (CD64), FcγRII (CD32), and FcγRIII (CD16). Other Fc receptors, such as IgA receptors (e.g., FcαRI), also can be targeted. The Fc receptor is preferably located on the surface of an effector cell, e.g., a monocyte, macrophage or an activated mononuclear cell. In a preferred embodiment, the bispecific and multispecific molecules bind to an Fc receptor at a site which is distinct from the immunoglobulin Fc (e.g., IgG or IgA) binding site of the receptor. Therefore, the binding of the bispecific and multispecific molecules is not blocked by physiological levels of immunoglobulins.

In yet another aspect, anti-GT468 antibodies of the invention are derivatized, linked to or co-expressed with another functional molecule, e.g., another peptide or protein (e.g., a Fab' fragment). For example, an antibody of the invention can be functionally linked (e.g., by chemical coupling, genetic fusion, noncovalent association or otherwise) to one or more other molecular entities, such as another antibody (e.g. to produce a bispecific or a multispecific antibody), a cytotoxin, cellular ligand or antigen (e.g. to produce an immunoconjugate, such as an immunotoxin). An antibody of the present invention can be linked to other therapeutic moieties, e.g., a radioisotope, a small molecule anti-cancer drug, a recombinant cytokine or chemokine. Accordingly, the present invention encompasses a large variety of antibody conjugates, bispecific and multispecific molecules, and fusion proteins, all of which bind to GT468 expressing cells and/or to cells being characterized by association of GT468 with their cell surface and which can be used to target other molecules to such cells.

In a further aspect, the invention also envisions GT468-binding proteins derived from non-immunoglobulin domains, in particular single-chain proteins. Such binding proteins and methods for their production are described, for example, in Binz et al. (2005) Nature Biotechnology 23 (10): 1257-1268, herein incorporated by reference. It is to be understood that the teaching given herein with respect to immunoglobulin or immunoglobulin derived binding molecules correspondingly also applies to binding molecules derived from non-immunoglobulin domains. In particular, using such binding molecules derived from non-immunoglobulin domains it is possible to block GT468 of cells expressing said target and/or being characterized by association of said target with their cell surface and thus, to bring about therapeutic effects as disclosed herein for antibodies of the invention, in particular the inhibition of one or more activities of tumor cells as disclosed herein such as proliferation. Although not mandatory, it is possible to confer effector functions of antibodies to such non-immunoglobulin binding molecules by e.g. fusion to the Fc region of antibodies.

In still another aspect, the invention provides compositions, e.g., pharmaceutical and diagnostic compositions/kits, comprising a pharmaceutically acceptable carrier formulated along with one or a combination of antibodies of the invention. In a particular embodiment, the composition includes a combination of antibodies which bind to distinct epitopes or which possess distinct functional characteristics, such as inducing CDC and/or ADCC and inducing apoptosis. In this embodiment of the invention, antibodies may be used in combination, e.g., as a pharmaceutical composition comprising two or more anti-GT468 monoclonal antibodies. For example, anti-GT468 antibodies having different but complementary activities can be combined in a single therapy to achieve a desired therapeutic effect. In a preferred embodiment, the composition includes an anti-GT468 antibody that mediates CDC combined with another anti-GT468 antibody that induces apoptosis. In another embodiment, the composition includes an anti-GT468 antibody that mediates highly effective killing of target cells in the presence of effector cells, combined with another anti-GT468 antibody that inhibits the growth of cells expressing GT468 and/or being characterized by association of GT468 with their cell surface.

The present invention also includes the simultaneous or sequential administration of two or more anti-GT468 antibodies of the invention, wherein preferably at least one of said antibodies is a chimeric anti-GT468 antibody and at least one further antibody is a human anti-GT468 antibody, the antibodies binding to the same or different epitopes of GT468. Preferably, a chimeric GT468 antibody of the invention is administered first followed by the administration of a human anti-GT468 antibody of the invention, wherein the human anti-GT468 antibody is preferably administered for an extended period of time, i.e. as maintenance therapy.

Antibodies, immunoconjugates, bispecific and multispecific molecules and compositions of the present invention can be used in a variety of methods for inhibiting growth of cells expressing GT468 and/or being characterized by association of GT468 with their cell surface and/or selectively killing cells expressing GT468 and/or being characterized by association of GT468 with their cell surface by contacting the cells with an effective amount of the antibody, immunconjugate, bispecific/multispecific molecule or composition, such that the growth of the cell is inhibited and/or the cell is killed. In one embodiment, the method includes killing of the cell expressing GT468 and/or being characterized by association of GT468 with their cell surface, optionally in the presence of effector cells, for example, by CDC, apoptosis, ADCC, phagocytosis, or by a combination of two or more of these mechanisms. Cells expressing GT468 and/or being characterized by association of GT468 with their cell surface which can be inhibited or killed using the antibodies of the invention include cancer cells such as breast, lung, gastric, ovarian, liver, colon, pancreatic, esophageal, head & neck, kidney, prostate and liver cells.

Accordingly, antibodies of the present invention can be used to treat and/or prevent a variety of diseases involving cells expressing GT468 and/or being characterized by association of GT468 with their cell surface by administering the antibodies to patients suffering from such diseases. Exemplary diseases that can be treated (e.g., ameliorated) or prevented include, but are not limited to, tumorigenic diseases. Examples of tumorigenic diseases, which can be treated and/or prevented, include breast cancer, lung cancer, gastric cancer, ovarian cancer, hepatocellular cancer, colon cancer, pancreatic cancer, esophageal cancer, head & neck cancer, kidney cancer, prostate cancer and liver cancer.

In a particular embodiment of the invention, the subject being administered the antibody is additionally treated with a chemotherapeutic agent, radiation, or an agent that modulates, e.g., enhances or inhibits, the expression or activity of an Fc receptor, e.g. an Fc-gamma receptor, such as a cytokine. Typical cytokines for administration during treatment include granulocyte colony-stimulating factor (G-CSF), granulocyte-macrophage colony-stimulating factor (GM-CSF), interferon-$\gamma$ (IFN-$\gamma$), and tumor necrosis factor (TNF). Typical therapeutic agents include, among others, anti-neoplastic agents such as doxorubicin, cisplatin, taxotere, 5-fluoruracil, methotrexat, gemzitabin and cyclophosphamide.

In yet another aspect, the invention relates to an immunization strategy to immunize non-human animals such as mice with human GT468 or a peptide fragment thereof to obtain antibodies. Preferred peptides for immunization are those selected from the group consisting of SEQ ID NO: 2-10 and 35-79, or derivatives thereof. Accordingly, in preferred embodiments, the antibodies of the invention are those obtained by immunization using peptides selected from the group consisting of SEQ ID NO: 2-10 and 35-79, or derivatives thereof. Analogously, antibodies to GT468 can be generated in a transgenic non-human animal, such as a transgenic mouse. The transgenic non-human animal may be a transgenic mouse having a genome comprising a heavy chain transgene and a light chain transgene encoding all or a portion of an antibody.

Wildtype as well as transgenic non-human animals can be immunized with a purified or enriched preparation of GT468 antigen and/or nucleic acids and/or cells expressing GT468 or a peptide fragment thereof. Preferably, the non-human animal is capable of producing multiple isotypes of human monoclonal antibodies to GT468 (e.g., IgG, IgA and/or IgM) by undergoing V-D-J recombination and isotype switching. Isotype switching may occur by e.g., classical or non-classical isotype switching.

Accordingly, in yet another aspect, the invention provides isolated B cells from a non-human animal as described above. The isolated B cells can then be immortalized by fusion to an immortalized cell to provide a source (e.g., a hybridoma) of antibodies of the invention. Such hybridomas (i.e., which produce antibodies of the invention) are also included within the scope of the invention.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as E. coli, and fungi, such as yeast. Alternatively, they can be produced recombinantly in a transgenic non-human animal or plant.

Preferred hybridoma cells for producing antibodies of the invention are those deposited at the DSMZ (Inhoffenstr. 7B, 38124 Braunschweig, Germany) having the following designations and accession numbers:

a. 4E9-1H9, accesssion no. DSM ACC2822, deposited on Mar. 13, 2007
b. 9B6-2A9, accesssion no. DSM ACC2826, deposited on Mar. 13, 2007
c. 59D6-2F2, accesssion no. DSM ACC2824, deposited on Mar. 13, 2007
d. 61C11-2B5, accesssion no. DSM ACC2825, deposited on Mar. 13, 2007
e. 78H11-1H6, accesssion no. DSM ACC2823, deposited on Mar. 13, 2007
f. 22-1A-1, accesssion no. DSM ACCXXXX, deposited on Mar. 11, 2008
g. 22-2A-1, accesssion no. DSM ACCXXXX, deposited on Mar. 11, 2008
h. 22-9B-1, accesssion no. DSM ACCXXXX, deposited on Mar. 11, 2008
i. 23-33A-1, accesssion no. DSM ACCXXXX, deposited on Mar. 11, 2008
j. 23-19A-1, accesssion no. DSM ACCXXXX, deposited on Mar. 11, 2008
k. F11#33F7D12, accesssion no. DSM ACCXXXX, deposited on Mar. 11, 2008
l. 4A12 2D4 1A10, accesssion no. DSM ACCXXXX, deposited on Mar. 11, 2008
m. 4E9 1D12 2D4, accesssion no. DSM ACCXXXX, deposited on Mar. 11, 2008

Preferred antibodies of the invention are those produced by and obtainable from the above-described hybridomas and the chimerized and humanized forms thereof. Further preferred antibodies of the invention are those having the specificity of the antibodies produced by and obtainable from the above-described hybridomas and, in particular, those comprising the antigen binding portion or antigen binding site, in particular the variable region, of the antibodies produced by and obtainable from the above-described hybridomas.

In preferred embodiments, antibodies, in particular chimerised forms of antibodies according to the invention include antibodies comprising a heavy chain constant region (CH) comprising an amino acid sequence derived from a human heavy chain constant region such as the amino acid sequence represented by SEQ ID NO: 17 or 24 or a fragment thereof. In further preferred embodiments, antibodies, in particular chimerised forms of antibodies according to the invention include antibodies comprising a light chain constant region (CL) comprising an amino acid sequence derived from a human light chain constant region such as the amino acid sequence represented by SEQ ID NO: 18 or 22 or a fragment thereof. In a particular preferred embodiment, antibodies, in particular chimerised forms of antibodies according to the invention include antibodies which comprise a CH comprising an amino acid sequence derived from a human CH such as the amino acid sequence represented by SEQ ID NO: 17 or 24 or a fragment thereof and which comprise a CL comprising an amino acid sequence derived from a human CL such as the amino acid sequence represented by SEQ ID NO: 18 or 22 or a fragment thereof.

A CH comprising the amino acid sequence represented by SEQ ID NO: 17 may be encoded by a nucleic acid comprising the nucleic acid sequence represented by SEQ ID NO: 20. A CH comprising the amino acid sequence represented by SEQ ID NO: 24 may be encoded by a nucleic acid comprising the nucleic acid sequence represented by SEQ ID NO: 23. A CL comprising the amino acid sequence represented by SEQ ID NO: 18 may be encoded by a nucleic acid comprising the nucleic acid sequence represented by SEQ ID NO: 19. A CL comprising the amino acid sequence represented by SEQ ID NO: 22 may be encoded by a nucleic acid comprising the nucleic acid sequence represented by SEQ ID NO: 21.

"Fragment" or "fragment of an amino acid sequence" as used above relates to a part of an antibody sequence, i.e. a sequence which represents the antibody sequence shortened at the N- and/or C-terminus, which when it replaces said antibody sequence in an antibody retains binding of said antibody to GT468 and preferably functions of said antibody as described herein, e.g. CDC mediated lysis or ADCC mediated lysis. Preferably, a fragment of an amino acid sequence comprises at least 80%, preferably at least 90%, 95%, 96%, 97%, 98%, or 99% of the amino acid residues from said amino acid sequence. Fragments of amino acid sequences described herein may be encoded by respective fragments of nucleic acid sequences encoding said amino acid sequences.

The present invention also relates to nucleic acids comprising genes or nucleic acid sequences encoding antibodies or parts thereof, e.g. an antibody chain, as described herein. The nucleic acids may be comprised in a vector, e.g., a plasmid, cosmid, virus, bacteriophage or another vector used e.g. conventionally in genetic engineering. The vector may comprise further genes such as marker genes which allow for the selection of the vector in a suitable host cell and under suitable conditions. Furthermore, the vector may comprise expression control elements allowing proper expression of the coding regions in suitable hosts. Such control elements are known to the artisan and may include a promoter, a splice cassette, and a translation initiation codon.

Preferably, the nucleic acid of the invention is operatively attached to the above expression control sequences allowing expression in eukaryotic or prokaryotic cells. Control elements ensuring expression in eukaryotic or prokaryotic cells are well known to those skilled in the art.

Methods for construction of nucleic acid molecules according to the present invention, for construction of vectors comprising the above nucleic acid molecules, for introduction of the vectors into appropriately chosen host cells, for causing or achieving the expression are well-known in the art.

A further aspect of the present invention relates to a host cell comprising a nucleic acid or vector as disclosed herein.

Other features and advantages of the instant invention will be apparent from the following detailed description and claims.

BRIEF DESCRIPTION OF THE DRAWINGS

FIG. 2. GT468 is a cell surface associated protein. (A) Staining of methanol-fixed and (B) non-fixed MCF-7 and BT-549 breast cancer cells with anti-GT468/C-term antibody after transfection with GT468-specific siRNA (siRNA#1) or non-silencing siRNA (ns-siRNA).

FIG. 6. Cyclin D1 and AKT kinase are involved in GT468 function. (A) Quantitative real-time RT-PCR analysis and (B) western blot analysis of cyclin D1 after cells were treated for 72 h with GT468 specific siRNA duplexes. Western blot analysis of AKT Ser473 phosphorylation after (C) 72 h of GT468 knock down and after (D) 1 h of treatment with anti-GT468/C-term antibody.

Figure 7:
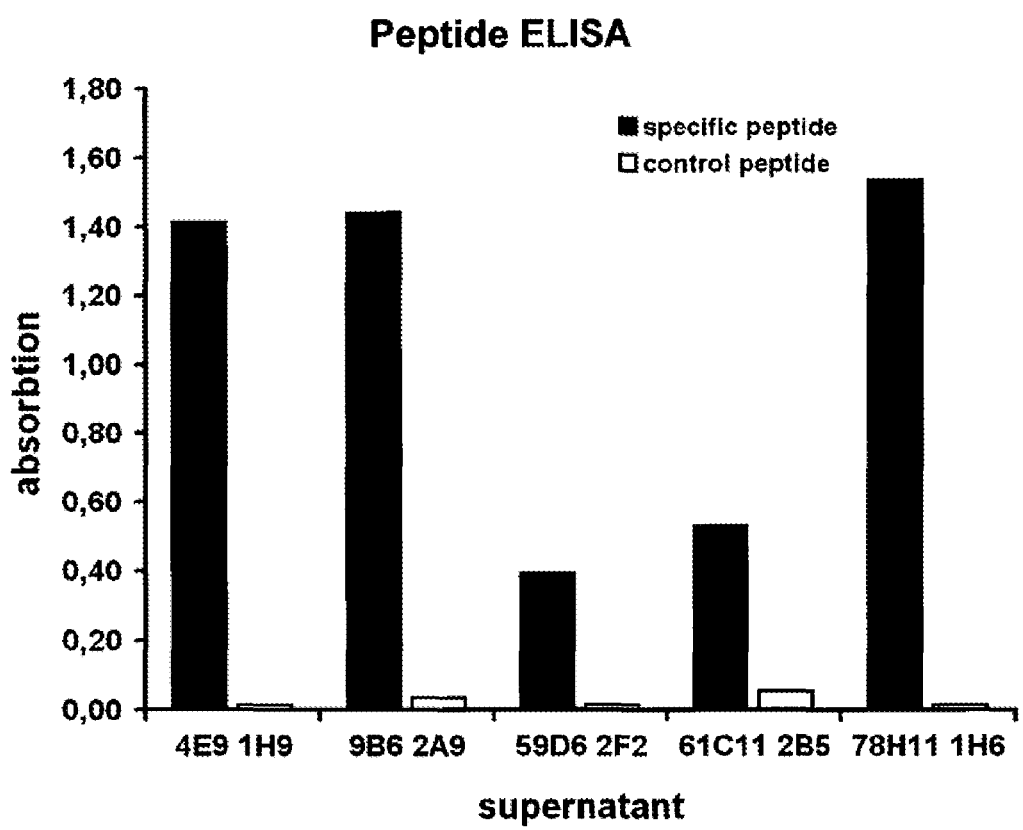

FIG. 7. Peptide ELISA for determining the specificity of antibodies raised against GT468 in hybridoma supernatants. Hybridoma supernatants only are reactive with peptides used for immunization.

Figure 8:
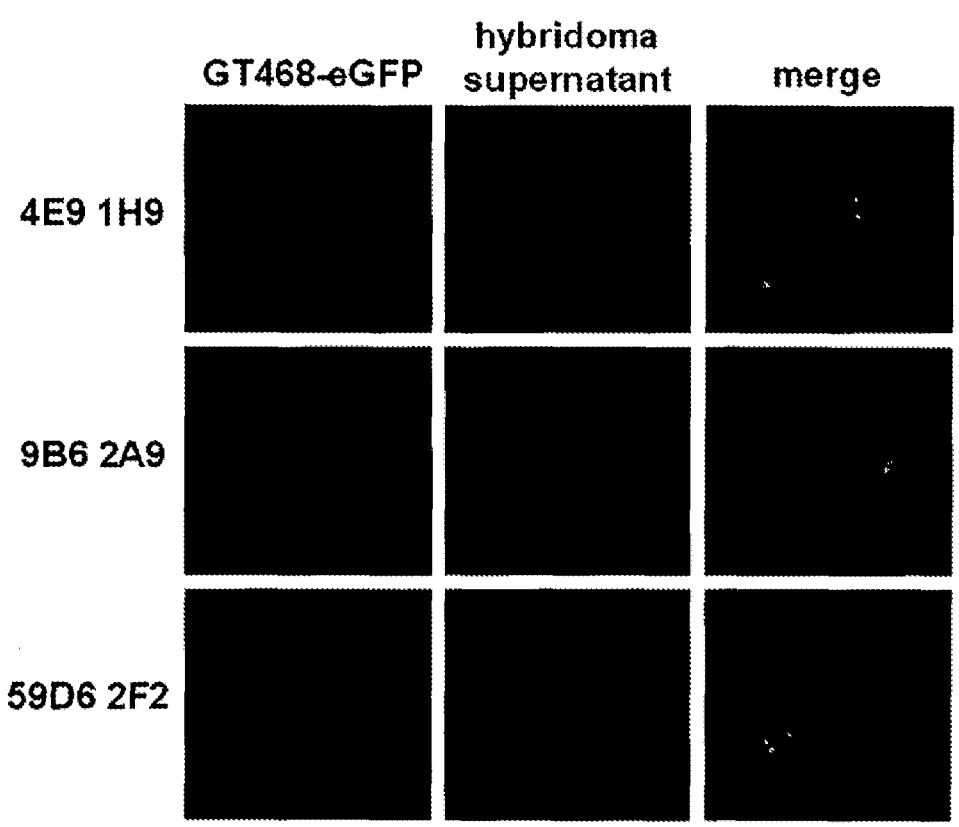

FIG. 8. Staining of CHO cells transfected with a GT468-eGFP construct by hybridoma supernatants containing antibodies raised against GT468. The hybridoma supernatants specifically stain cells expressing GT468-eGFP.

Figure 9:
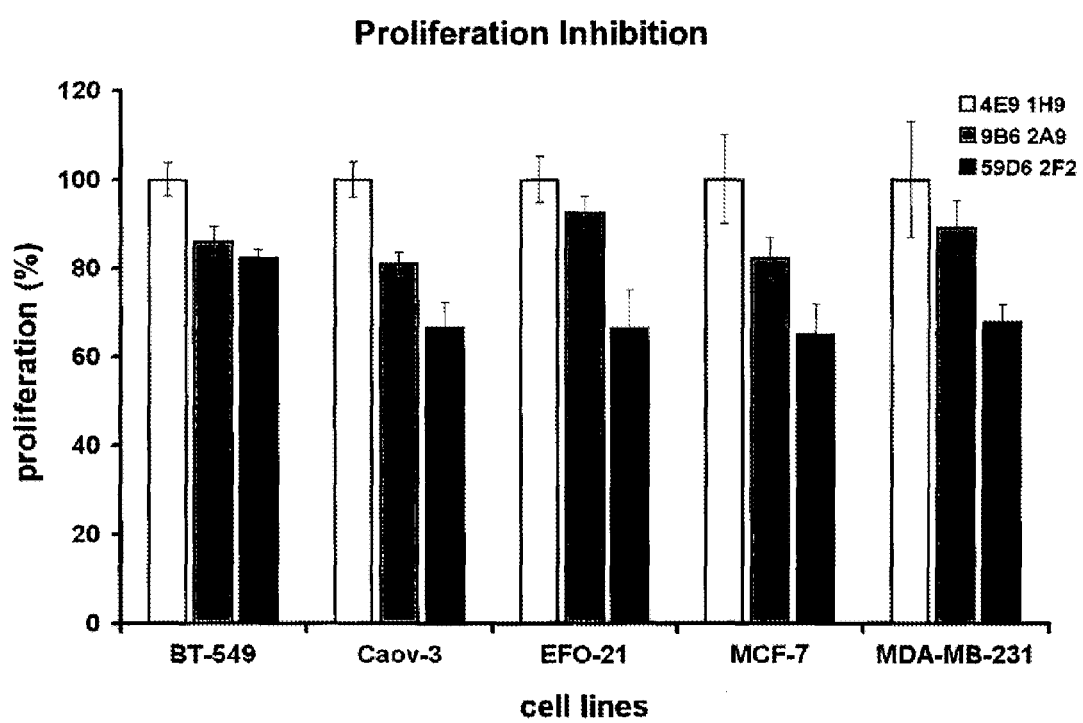

FIG. 9. GT468 is drugable by function-antagonizing monoclonal antibodies. Proliferation analysis of different cancer cell lines after incubation with hybridoma supernatants for 72 h.

Figure 10:
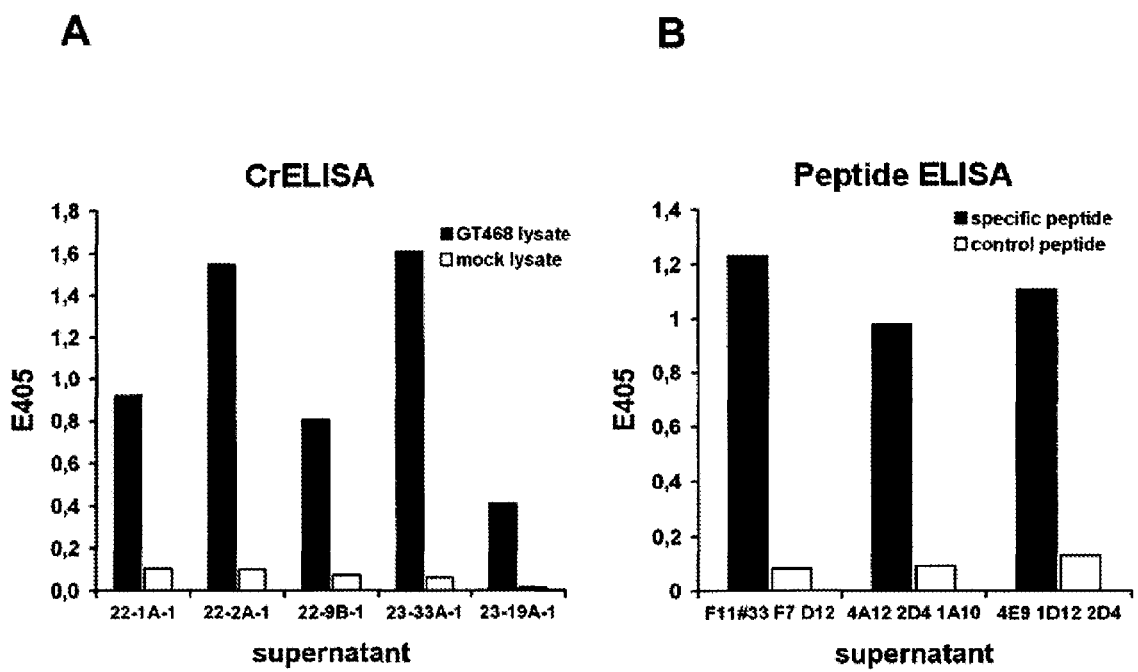

FIG. 10. Crude-lysate (CrELISA) (A) or peptide-specific ELISA (B) for determining the specificity of antibodies raised against GT468 in hybridoma supernatants. Hybridoma supernatants only are reactive with the GT468 lysate (A) or the respective peptide used for immunization (B).

Figure 11:
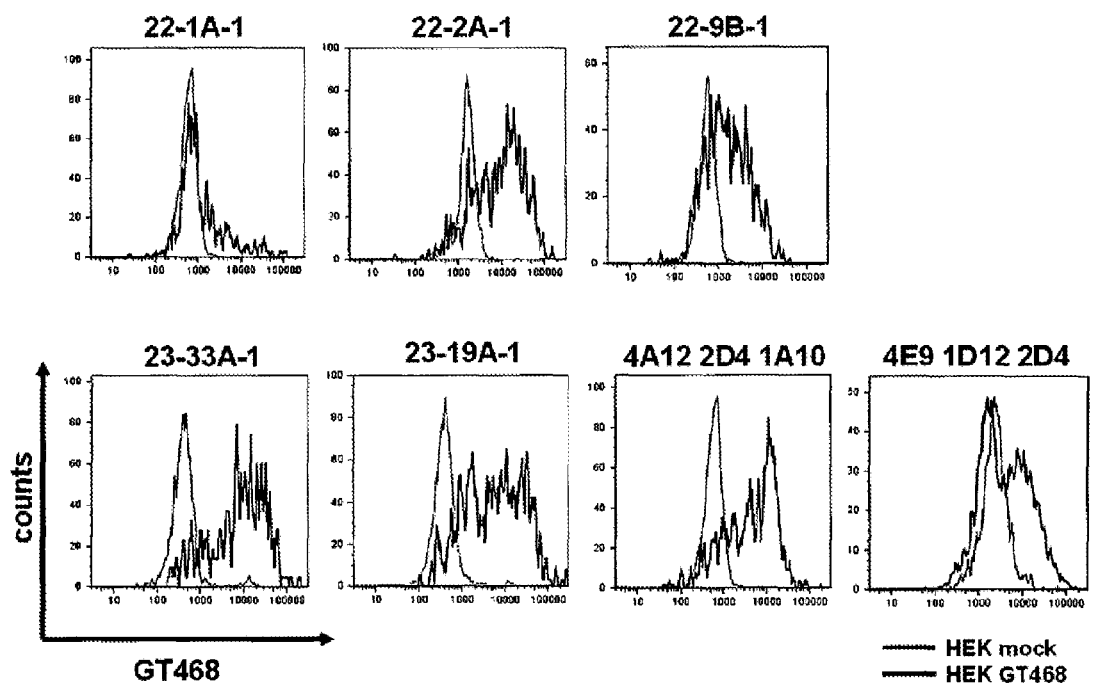

FIG. 11. Flowcytometric analysis for determining the specificity of antibodies raised against GT468 in hybridoma supernatants. All hybridoma supernatants showed specific staining of GT468 transfected cells, whereas no staining was observed on mock transfected cells.

Figure 12:
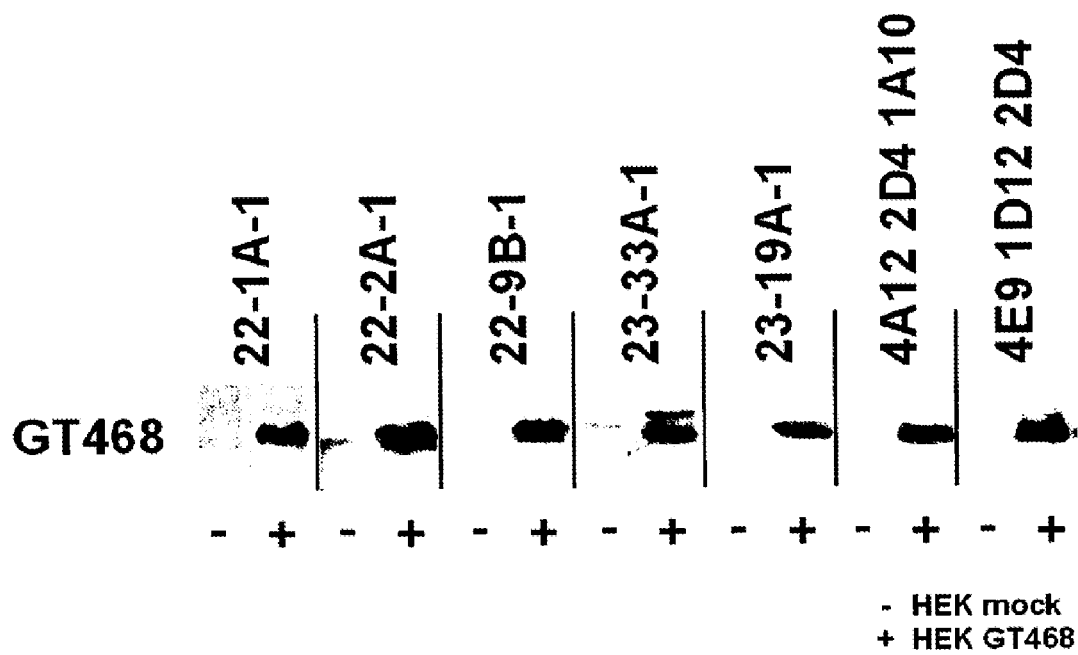

FIG. 12. Western blot for determining the specificity of antibodies raised against GT468 in hybridoma supernatants. All hybridoma supernatants showed specific reactivity with lysates of HEK293 cells transfected with GT468 pcDNA3.1 expression plasmid, whereas lysates of mock transfeted cells showed no signal. The faint signal of hybridoma supernatant 23-33A-1 in the mock lysate is due to spillover of the HEK GT468 lysate.

FIG. 13. Peptide ELISA to identify antibody-binding epitopes in the GT468 protein. Hybridoma supernatants 22-1A-1, 23-33A-1, and 23-19A-1 each showed binding to two overlapping peptides implying reactivity to a linear epitope of GT468. The binding patterns of 22-2A-1 and 22-9B-1 imply reactivity to a conformational epitope (discontinous epitope) of the GT468 protein.

Figure 14:
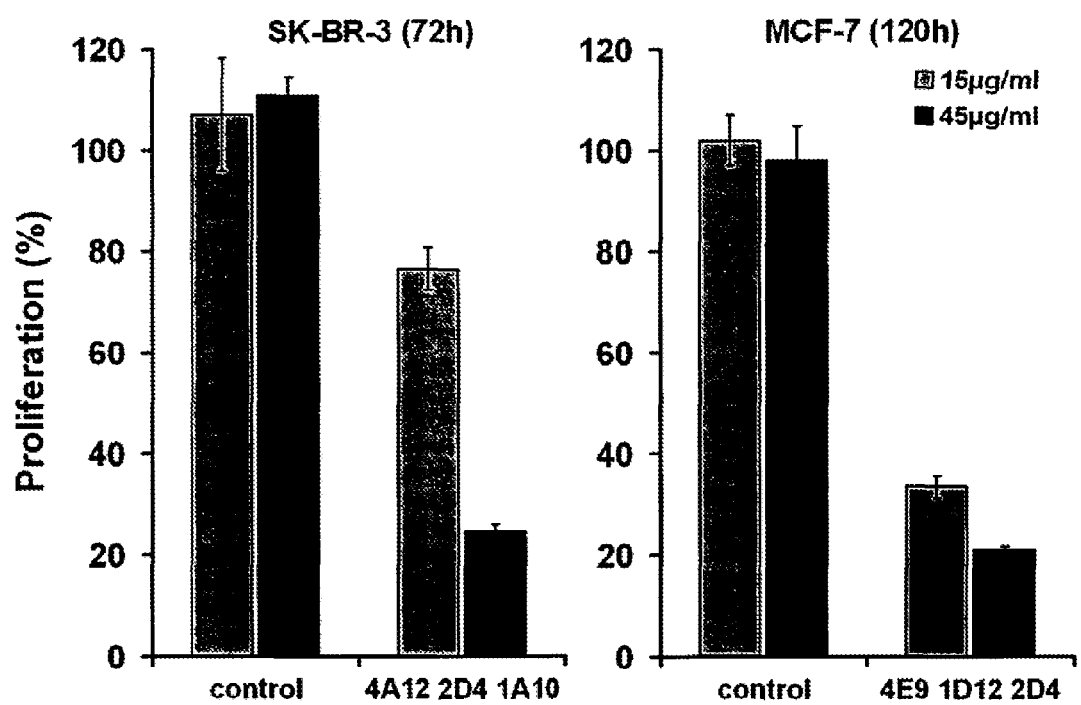

FIG. 14. GT468 is drugable by function-antagonizing monoclonal antibodies. Proliferation analysis of different cancer cell lines after incubation with purified hybridoma supernatants for 72 h or 120 h.

DETAILED DESCRIPTION OF THE INVENTION

The antibodies described herein may be isolated monoclonal antibodies which specifically bind to an epitope present on GT468, preferably an epitope located with the extracellular domain of GT468, more preferably SEQ ID NOs: 3-10 and 35-79. Isolated monoclonal antibodies encompassed by the present invention include IgA, IgG1-4, IgE, IgM, and IgD antibodies. In one embodiment the antibody is an IgG1 antibody, more particularly an IgG1, kappa or IgG1, lambda isotype. In another embodiment the antibody is an IgG3 antibody, more particularly an IgG3, kappa or IgG3, lambda isotype. In yet another embodiment the antibody is an IgG4 antibody, more particularly an IgG4, kappa or IgG4, lambda isotype. In still another embodiment the antibody is an IgA1 or IgA2 antibody. In still another embodiment the antibody is an IgM antibody.

In one embodiment the invention relates to antibodies which (i) bind to cells expressing GT468 and/or being characterized by association of GT468 with their cell surface, and (ii) do not bind to cells not expressing GT468 and/or not being characterized by association of GT468 with their cell surface. The antibodies of the invention preferably (i) mediate killing and/or inhibit proliferation of cells expressing GT468 and/or being characterized by association of GT468 with their cell surface, and (ii) do not mediate killing and/or do not inhibit proliferation of cells not expressing GT468 and/or not being characterized by association of GT468 with their cell surface.

In another embodiment, the invention relates to antibodies which (i) bind to tumor cells expressing GT468 and/or being characterized by association of GT468 with their cell surface, and (ii) do not bind to GT468 of non-cancer placental cells.

The invention also includes antibodies which (i) mediate killing of tumor cells expressing GT468 and/or being characterized by association of GT468 with their cell surface, and (ii) do not mediate killing of GT468 expressing cells of normal placenta.

Antibodies of the invention include fully human antibodies. Such antibodies may be produced in a non-human transgenic animal, e.g., a transgenic mouse, capable of producing multiple isotypes of human monoclonal antibodies to GT468 by undergoing V-D-J recombination and isotype switching. Such transgenic animal can also be a transgenic rabbit for producing polyclonal antibodies such as disclosed in US 2003/0017534.

Binding of an antibody of the invention to the GT468 antigen may mediate the killing of cells expressing GT468 and/or being characterized by association of GT468 with their cell surface (e.g. a tumor cell), e.g. by activation of the complement system, and/or may inhibit proliferation of cells expressing GT468 and/or being characterized by association of GT468 with their cell surface (e.g. a tumor cell). Alternatively or in addition to mediating killing of cells expressing GT468 and/or being characterized by association of GT468 with their cell surface and/or inhibiting proliferation of cells expressing GT468 and/or being characterized by association of GT468 with their cell surface, binding of an antibody of the invention to the GT468 antigen may inhibit motility, migration and/or invasion of cells expressing GT468 and/or being characterized by association of GT468 with their cell surface (e.g. a tumor cell), and thus, may inhibit metastatic spread of tumor cells. The killing of cells expressing GT468 and/or being characterized by association of GT468 with their cell surface may occur by one or more of the following mechanisms: complement dependent cytotoxity (CDC) of cells expressing GT468 and/or being characterized by association of GT468 with their cell surface; apoptosis of cells expressing GT468 and/or being characterized by association of GT468 with their cell surface; effector cell phagocytosis of cells expressing GT468 and/or being characterized by association of GT468 with their cell surface; or effector cell antibody dependent cellular cytotoxicity (ADCC) of cells expressing GT468 and/or being characterized by association of GT468 with their cell surface.

In order that the present invention may be more readily understood, certain terms are first defined. Additional definitions are set forth throughout the detailed description.

DEFINITION OF TERMS

The term "GT468" preferably relates to human GT468, and in particular to (i) a nucleic acid comprising a nucleic acid sequence encoding the amino sequence of SEQ ID NO: 2 such as a nucleic acid comprising the nucleic acid sequence of SEQ ID NO: 1 or (ii) a protein comprising the amino acid sequence of SEQ ID NO: 2, and includes any variants, conformations, isoforms and species homologs thereof which are naturally expressed by cells or are expressed by cells transfected with the GT468 gene. In one embodiment, the term "GT468" relates to the portion of GT468 corresponding to the extracellular domain and preferably relates to the amino acid sequence of GT468 not including the N-terminal hydrophobic domain. The term "GT468" includes a protein comprising amino acids 29 to 119, preferably amino acids 29 to 212 and more preferably amino acids 23 to 212 of SEQ ID NO: 2.

"Variants of GT468" also includes a form of GT468 consisting essentially of the extracellular domain or ectodomain of GT468. According to the invention, the terms "extracellular domain" or "ectodomain" with respect to GT468 relate to the portion of GT468 which is found in association with the surface of cells expressing GT468. Preferably, said "extracellular domain" or "ectodomain" is present in the extracellular compartment. The GT468 "extracellular domain" or "ectodomain" preferably refers to the portion of full-length GT468 which lacks the N-terminal hydrophobic domain. According to the invention, the term "hydrophobic domain" with respect to GT468 relates to the portion of GT468 not being part of the extracellular domain and preferably including a hydrophobic sequence located close to the N-terminus of GT468. The "hydrophobic domain" of GT468 may include a sequence preceding the hydrophobic sequence and being located at the N-terminal end of GT468. With respect to SEQ ID NO: 2, the N-terminal hydrophobic domain preferably comprises amino acids 1 to 22. It will be understood that any hydrophobic domains or sequences identified for the GT468 polypeptides of the present invention are identified pursuant to criteria routinely employed in the art for identifying hydrophobic domains or sequences. The exact boundaries of a hydrophobic domain may vary but most likely by no more than about 5 amino acids at either end of the domain as initially identified herein. Optionally, therefore, an extracellular domain of a GT468 polypeptpide may contain from about 5 or fewer amino acids on either side of the hydrophobic domain/extracellular domain boundary as identified herein.

"Cell surface" is used in accordance with its normal meaning in the art, and thus includes the outside of the cell which is accessible to binding by proteins and other molecules.

The expression "GT468 expressed on the surface of cells" means that GT468 expressed by cells is found in association with the surface of said cells.

GT468 is associated with the surface of cells if it is located at the surface of said cells and is accessible to binding by GT468-specific antibodies added to the cells. In preferred embodiments, a cell being characterized by association of GT468 with its cell surface is a cell expressing GT468. It is to be understood that in the case where GT468 is expressed by cells, the GT468 associated with the surface of said cells may only be a portion of the expressed GT468, in particular the extracellular domain thereof as defined above.

The term "GT468 variant" shall encompass (i) GT468 splice variants, (ii) GT468-posttranslationally modified variants, particularly including variants with different glycosylation such as N-glycosylation status, (iii) GT468 conformation variants, (iv) GT468 cancer related and GT468 non-cancer related variants.

The term "raft" refers to the sphingolipid- and cholesterol-rich membrane microdomains located in the outer leaflet area of the plasma membrane of a cell. The ability of certain proteins to associate within such domains and their ability of forming "aggregates" or "focal aggregates" can effect the protein's function. For example, the translocation of GT468 molecules into such structures, after being bound by antibodies of the present invention, creates a high density of GT468 antigen-antibody complexes in the plasma membranes. Such a high density of GT468 antigen-antibody complexes can enable efficient activation of the complement system during CDC.

According to the invention, the term "disease" refers to any pathological state, including cancer, in particular those forms of cancer described herein.

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "treatment of a disease" includes curing, shortening the duration, ameliorating, preventing, slowing down or inhibiting progression or worsening, or preventing or delaying the onset of a disease or the symptoms thereof.

According to the invention, a sample may be any sample useful according to the present invention, in particular a biological sample such a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the invention, the term "biological sample" also includes fractions of biological samples.

The term "antibody" refers to a glycoprotein comprising at least two heavy (H) chains and two light (L) chains inter-connected by disulfide bonds, or an antigen binding portion thereof. The term "antibody" also includes all recombinant forms of antibodies, in particular of the antibodies described herein, e.g., antibodies expressed in prokaryotes, unglycosylated antibodies, and any antigen-binding antibody fragments and derivatives as described below. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The term "antigen-binding portion" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "epitope" means a protein determinant capable of binding to an antibody, wherein the term "binding" herein preferably relates to a specific binding. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "discontinuous epitope" as used herein, means a conformational epitope on a protein antigen which is formed from at least two separate regions in the primary sequence of the protein.

The term "bispecific molecule" is intended to include any agent, e.g., a protein, peptide, or protein or peptide complex, which has two different binding specificities. For example, the molecule may bind to, or interact with (a) a cell surface antigen, and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to GT468, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

The invention also includes derivatives of the antibodies described herein. The term "antibody derivatives" refers to any modified form of an antibody, e.g., a conjugate of the antibody and another agent or antibody. As used herein, an antibody is "derived from" a particular germline sequence if the antibody is obtained from a system by immunizing an animal or by screening an immunoglobulin gene library, and wherein the selected antibody is at least 90%, more preferably at least 95%, even more preferably at least 96%, 97%, 98%, or 99% identical in amino acid sequence to the amino acid sequence encoded by the germline immunoglobulin gene. Typically, an antibody derived from a particular germline sequence will display no more than 10 amino acid differences, more preferably, no more than 5, or even more preferably, no more than 4, 3, 2, or 1 amino acid difference from the amino acid sequence encoded by the germline immunoglobulin gene.

As used herein, the term "heteroantibodies" refers to two or more antibodies, derivatives thereof, or antigen binding regions linked together, at least two of which have different specificities. These different specificities include a binding specificity for an Fc receptor on an effector cell, and a binding specificity for an antigen or epitope on a target cell, e.g., a tumor cell.

The antibodies described herein may be human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies described herein are preferably isolated. An "isolated antibody" as used herein, is intended to refer to an antibody which is substantially free of other antibodies having different antigenic specificities (e.g., an isolated antibody that specifically binds to GT468 is substantially free of antibodies that specifically bind antigens other than GT468). An isolated antibody that specifically binds to an epitope, isoform or variant of human GT468 may, however, have cross-reactivity to other related antigens, e.g., from other species (e.g., GT468 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition.

According to the invention, the term "binding" preferably relates to "specific binding". As used herein, "specific binding" refers to antibody binding to a predetermined antigen. Typically, the antibody binds with an affinity corresponding to a KD of about $1 \times 10^{-7}$ M or less, and binds to the predetermined antigen with an affinity corresponding to a KD that is at least two orders of magnitude lower than its affinity for binding to a non-specific antigen (e.g., BSA, casein) other than the predetermined antigen or a closely-related antigen.

The term "KD" (M), as used herein, is intended to refer to the dissociation equilibrium constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that a nucleic acid is also functionally linked to the expression control sequence naturally and the term "heterologous" means that a nucleic acid is not functionally linked to the expression control sequence naturally.

A nucleic acid, such as a nucleic acid expressing RNA and/or protein or peptide, and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

According to the invention, the term "expression" is used in its most general meaning and comprises the production of RNA or of RNA and protein/peptide. It also comprises partial expression of nucleic acids. Furthermore, expression may be carried out transiently or stably.

In a preferred embodiment, a nucleic acid molecule is according to the invention present in a vector, where appropriate with a promoter, which controls expression of the nucleic acid. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

As the vector for expression of an antibody, either of a vector type in which the antibody heavy chain and light chain are present in different vectors or a vector type in which the heavy chain and light chain are present in the same vector can be used.

The teaching given herein with respect to specific nucleic acid and amino acid sequences, e.g. those shown in the sequence listing, is to be construed so as to also relate to modifications of said specific sequences resulting in sequences which are functionally equivalent to said specific sequences, e.g. amino acid sequences exhibiting properties identical or similar to those of the specific amino acid sequences and nucleic acid sequences encoding amino acid sequences exhibiting properties identical or similar to those of the amino acid sequences encoded by the specific nucleic acid sequences. One important property is to retain binding of an antibody to its target or to sustain effector functions of an antibody. Preferably, a sequence modified with respect to a specific sequence, when it replaces the specific sequence in an antibody retains binding of said antibody to GT468 and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability to bind GT468. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

It is to be understood that the specific nucleic acids described herein also include nucleic acids modified for the sake of optimizing the codon usage in a particular host cell or organism. Differences in codon usage among organisms can lead to a variety of problems concerning heterologous gene expression. Codon optimization by changing one or more nucleotides of the original sequence can result in an optimization of the expression of a nucleic acid, in particular in optimization of translation efficacy, in a homologous or heterologous host in which said nucleic acid is to be expressed. For example if nucleic acids derived from human and encoding constant regions and/or framework regions of antibodies are to be used according to the present invention, e.g. for preparing chimeric or humanised antibodies, it may be preferred to modify said nucleic acids for the sake of optimization of codon usage, in particular if said nucleic acids, optionally fused to heterologous nucleic acids such as nucleic acids derived from other organisms as described herein, are to be expressed in cells from an organism different from human such as mouse or hamster. For example, the nucleic acid sequences encoding human light and heavy chain constant regions such as those according to SEQ ID NOs: 19 and 20, respectively, can be modified to include one or more, preferably, at least 1, 2, 3, 4, 5, 10, 15, 20 and preferably up to 10, 15, 20, 25, 30, 50, 70 or 100 or more nucleotide replacements resulting in an optimized codon usage but not resulting in a change of the amino acid sequence. Such nucleotide replacements preferably relate to replacements of nucleotides in SEQ ID Nos: 19 and 20, respectively, selected from the replacements shown in the following alignment of SEQ ID Nos: 19 and 20, respectively, with their modified counterparts and not resulting in a change in the encoded amino acid sequence or relate to corresponding replacements at corresponding positions in other nucleic acid sequences encoding human light and heavy chain constant regions, respectively. Preferably, all of the replacements shown in the following alignments of SEQ ID Nos: 19 and 20, respectively, with their modified counterparts not resulting in a change in the encoded amino acid sequence are effected in nucleic acid sequences encoding human light and heavy chain constant regions, respectively.

```
Alignment of SEQ ID NO: 19 and SEQ ID NO: 21:
CGTACGGTGGCTGCACCATCTGTCTTCATCTTCCCGCCATCTGATGAGCAGTTGAAATCT    60
|||||||||||  || || ||||||||||| ||| |||| |||| |||| |||| ||
CGTACGGTGGCCGCTCCCAGCGTGTTCATCTTCCCCCCCAGCGACGAGCAGCTGAAGTCC    60
GGAACTGCCTCTGTTGTGTGCCTGCTGAATAACTTCTATCCCAGAGAGGCCAAAGTACAG   120
|| || |||    || |||||||||||||| |||||||| ||| ||||||||| || |||
GGCACCGCCAGCGTGGTGTGCCTGCTGAACAACTTCTACCCCCGGGAGGCCAAGGTGCAG   120
TGGAAGGTGGATAACGCCCTCCAATCGGGTAACTCCCAGGAGAGTGTCACAGAGCAGGAC   180
|||||||||| |||||||||| ||   || || || ||||||||||||  ||||||||||
TGGAAGGTGGACAACGCCCTGCAGAGCGGCAACAGCCAGGAGAGCGTCACCGAGCAGGAC   180
AGCAAGGACAGCACCTACAGCCTCAGCAGCACCCTGACGCTGAGCAAAGCAGACTACGAG   240
||||||||||  |||||||||||| |||||||||||| || |||||| || |||||||||
AGCAAGGACTCCACCTACAGCCTGAGCAGCACCCTGACCCTGAGCAAGGCCGACTACGAG   240
AAACACAAAGTCTACGCCTGCGAAGTCACCCATCAGGGCCTGAGCTCGCCCGTCACAAAG   300
|| ||||| || |||||||||| ||| ||||||||||||||| |         ||| |||
AAGCACAAGGTGTACGCCTGCGAGGTGACCCACCAGGGCCTGTCCAGCCCCGTGACCAAG   300
AGCTTCAACAGGGGAGAGTGTTAG                                     324
||||||||||||||| |||||| |||
AGCTTCAACAGGGGCGAGTGCTAG                                     324

Alignment of SEQ ID NO: 20 and SEQ ID NO: 23:
GGCCCATCGGTCTTCCCCCTGGCACCCTCCTCCAAGAGCACCTCTGGGGGCACAGCGGCC    60
||||||   || |||||||||||  |||  | |||||||||    || |||||||| |||
GGCCCAAGCGTGTTCCCCCTGGCCCCCAGCAGCAAGAGCACCAGCGGCGGCACAGCCGCC    60
CTGGGCTGCCTGGTCAAGGACTACTTCCCCGAACCGGTGACGGTGTCGTGGAACTCAGGC   120
|||||||||||||| ||||||||||||||||| ||||| ||| ||  |||||||  ||
CTGGGCTGCCTGGTGAAGGACTACTTCCCCGAGCCCGTGACCGTGAGCTGGAACAGCGGA   120
GCCCTGACCAGCGGCGTGCACACCTTCCCGGCTGTCCTACAGTCCTCAGGACTCTACTCC   180
||||||||   ||||||||||||||||||| || || ||   |    ||  || |||  |
GCCCTGACCTCCGGCGTGCACACCTTCCCCGCCGTGCTGCAGAGCAGCGGCCTGTACAGC   180
CTCAGCAGCGTGGTGACCGTGCCCTCCAGCAGCTTGGGCACCCAGACCTACATCTGCAAC   240
||  |||||||||||||||||||||||||||||| |||||||||||||||||||||||||
CTGAGCAGCGTGGTGACCGTGCCCAGCAGCAGCCTGGGCACCCAGACCTACATCTGCAAC   240
GTGAATCACAAGCCCAGCAACACCAAGGTGGACAAGAAAGTTGAGCCCAAATCTTGTGAC   300
||||| |||||||||||||||||||||||||||| ||| |||||||||   ||   |||
GTGAACCACAAGCCCAGCAACACCAAGGTGGACAAGAGAGTGGAGCCCAAGAGCTGCGAC   300
AAAACTCACACATGCCCACCGTGCCCAGCACCTGAACTCCTGGGGGGACCGTCAGTCTTC   360
|| || ||||| |||| |||| |||||||||||||| |||||||  |||| ||||||||
AAGACCCACACCTGCCCCCCCTGCCCAGCCCCAGAGCTGCTGGGCGGACCCAGACTCTTC   360
CTCTTCCCCCCAAAACCCAAGGACACCCTCATGATCTCCCGGACCCCTGAGGTCACATGC   420
|| ||||||||| |||||||||||||||||| |||| | |||||||| ||||| || |||
CTGTTCCCCCCCAAGCCCAAGGACACCCTGATGATCAGCAGGACCCCCGAGGTGACCTGC   420
GTGGTGGTGGACGTGAGCCACGAAGACCCTGAGGTCAAGTTCAACTGGTACGTGGACGGC   480
||||||||||||||||||||||| |||  ||||||||||||||||||||||||||||||
GTGGTGGTGGACGTGAGCCACGAGGACCCAGAGGTGAAGTTCAACTGGTACGTGGACGGC   480
GTGGAGGTGCATAATGCCAAGACAAAGCCGCGGGAGGAGCAGTACAACAGCACGTACCGT   540
|||||||||||  |||| |||||| |||||| |||||||||||||||||||||| |||
GTGGAGGTGCACAACGCCAAGACCAAGCCCAGAGAGGAGCAGTACAACAGCACCTACAGG   540
GTGGTCAGCGTCCTCACCGTCCTGCACCAGGACTGGCTGAATGGCAAGGAGTACAAGTGC   600
|||||    ||| || |||||| ||||||||||||||||| |||||||| ||||||||||
GTGGTGTCCGTGCTGACCGTGCTGCACCAGGACTGGCTGAACGGCAAGGAATACAAGTGC   600
AAGGTCTCCAACAAAGCCCTCCCAGCCCCCATCGAGAAAACCATCTCCAAAGCCAAGGG    660
||||||||||||| ||||| ||||||||||||||| || |||||||||||| ||||||
AAGGTCTCCAACAAGGCCCTGCCAGCCCCCATCGAAAAGACCATCAGCAAGGCCAAGGGC   660
CAGCCCCGAGAACCAGACCTGTACACCCTGCCCCCATCCCGGGATGAGCTGACCAAGAAC   720
|||||  || ||  ||||| ||||||||||||||  |||||| ||||| |||||||||||
CAGCCACGGGAGCCCCAGGTGTACACCCTGCCCCCCAGCCGGGAGGAGATGACCAAGAAC   720
CAGGTCAGCCTGACCTGCCTGGTCAAAGGCTTCTATCCCAGCGACATCGCCGTGGAGTGG   780
|||||    |||||||| |||||  || ||||||| |||||||||||||||||||||||
CAGGTGTCCCTGACCTGTCTGGTGAAGGGCTTCTACCCCAGCGACATCGCCGTGGAGTGG   780
```

```
                                      -continued
GAGAGCAATGGGCAGCCGGAGAACAACTACAAGACCACGCCTCCCGTGCTGGACTCCGAC          840
|||||||| || ||||| ||||||||||||||||||| || || |||||||||   ||||
GAGAGCAACGGCCAGCCCGAGAACAACTACAAGACCACCCCCCCAGTGCTGGACAGCGAC          840
GGCTCCTTCTTCCTCTATAGCAAGCTCACCGTGGACAAGAGCAGGTGGCAGCAGGGGAAC          900
||| |||||||||| || ||||||||| ||||||||||||    |||||||||||||||| |||
GGCAGCTTCTTCCTGTACAGCAAGCTGACCGTGGACAAGTCCAGGTGGCAGCAGGGCAAC          900
GTCTTCTCATGCTCCGTGATGCATGAGGCTCTGCACAACCACTACACGCAGAAGAGCCTC          960
|| |||   |||    |||||||||| |||||  ||||||||||||||||| ||||| |||
GTGTTCAGCTGCAGCGTGATGCACGAGGCCCTGCACAACCACTACACCCAGAAGTCCCTG          960
TCCCTGTCTCCGGGTAAATGA                                                 981
|||| || || || |
AGCCTGAGCCCCGGCAAGTAG                                                 981
```

Furthermore, it may be desired according to the present invention to modify the amino acid sequences described herein, in particular those of human heavy chain constant regions to adapt the sequence to a desired allotype, e.g. an allotype found in the Caucasian population. Such modifications are preferably selected from the group consisting of the following amino acid replacements within SEQ ID NO: 17 or at corresponding positions within other human heavy chain constant regions: K93R, D235E, and L237M. Preferably, all of these modifications are included in amino acid sequences of human heavy chain constant regions.

According the invention, the term "corresponding positions" relates to nucleotides or amino acid residues which in a sequence alignment of two nucleic acid or protein sequences are aligned to each other.

Preferably the degree of identity between a specific nucleic acid sequence described herein and a nucleic acid sequence which is modified with respect to or which is a variant of said specific nucleic acid sequence will be at least 70%, preferably at least 75%, more preferably at least 80%, even more preferably at least 90% or most preferably at least 95%, 96%, 97%, 98% or 99%. Regarding GT468 nucleic acid variants, the degree of identity is preferably given for a region of at least about 300, at least about 400, at least about 450, at least about 500, at least about 550, at least about 600 or at least about 630 nucleotides. In preferred embodiments, the degree of identity is given for the entire length of the reference nucleic acid sequence, such as the nucleic acid sequences given in the sequence listing. Preferably, the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1× SDS at temperatures of up to 68° C.

Preferably the degree of similarity, preferably identity between a specific amino acid sequence described herein and an amino acid sequence which is modified with respect to or which is a variant of said specific amino acid sequence such as between amino acid sequences showing substantial homology will be at least 70%, preferably at least 80%, even more preferably at least 90% or most preferably at least 95%, 96%, 97%, 98% or 99%. Regarding GT468 polypeptide variants, the degree of similarity or identity is given preferably for a region of at least about 100, at least about 120, at least about 140, at least about 160, at least about 180, at least about 200, at least about 210 or 212 amino acids. In preferred embodiments, the degree of similarity or identity is given for the entire length of the reference amino acid sequence such as the amino acid sequences given in the sequence listing.

All of the above described modified sequences or sequence variants are within the scope of the present invention.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The "percentage identity" is obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

"Conservative substitutions," may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c)

positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

The present invention comprises antibodies in which alterations have been made in the Fc region in order to change the functional or pharmacokinetic properties of the antibodies. Such alterations may result in a decrease or increase of C1q binding and CDC or of FcγR binding and ADCC. Substitutions can, for example, be made in one or more of the amino acid residues of the heavy chain constant region, thereby causing an alteration in an effector function while retaining the ability to bind to the antigen as compared with the modified antibody, cf. U.S. Pat. No. 5,624,821 and U.S. Pat. No. 5,648,260.

The in vivo half-life of antibodies can be improved by modifying the salvage receptor epitope of the Ig constant domain or an Ig-like constant domain such that the molecule does not comprise an intact CH2 domain or an intact Ig Fc region, cf. U.S. Pat. No. 6,121,022 and U.S. Pat. No. 6,194,551. The in vivo half-life can furthermore be increased by making mutations in the Fc region, e.g., by substituting threonine for leucine at position 252, by substituting threonine for serine at position 254, or by substituting threonine for phenylalanine at position 256, cf. U.S. Pat. No. 6,277,375.

Furthermore, the glycosylation pattern of antibodies can be modified in order to change the effector function of the antibodies. For example, the antibodies can be expressed in a transfectoma which does not add the fucose unit normally attached to Asn at position 297 of the Fc region in order to enhance the affinity of the Fc region for Fc-Receptors which, in turn, will result in an increased ADCC of the antibodies in the presence of NK cells, cf. Shield et al. (2002) JBC, 277: 26733. Furthermore, modification of galactosylation can be made in order to modify CDC.

Alternatively, in another embodiment, mutations can be introduced randomly along all or part of a anti-GT468 antibody coding sequence, such as by saturation mutagenesis, and the resulting modified anti-GT468 antibodies can be screened for binding activity.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, NS/0 cells, and lymphocytic cells.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

The terms "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-GT468 antibodies when immunized with GT468 antigen and/or cells expressing GT468. The human heavy chain transgene can be integrated into the chromosomal DNA of the mouse, as is the case for transgenic mice, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to GT468 (e.g., IgG, IgA and/or IgE) by undergoing V-D-J recombination and isotype switching.

"Reduce" or "inhibit" as used herein means the ability to cause an overall decrease, preferably of 5% or greater, 10% or greater, 20% or greater, more preferably of 50% or greater, and most preferably of 75% or greater, in the level, e.g. in the level of proliferation of cells.

Mechanisms of mAb Action

Although the following provides considerations regarding the mechanism underlying the therapeutic efficacy of antibodies of the invention it is not to be considered as limiting to the invention in any way.

The antibodies described herein preferably interact with components of the immune system, preferably through ADCC or CDC. Antibodies of the invention can also be used to target payloads (e.g., radioisotopes, drugs or toxins) to directly kill tumor cells or can be used synergistically with traditional chemotherapeutic agents, attacking tumors through complementary mechanisms of action that may include anti-tumor immune responses that may have been compromised owing to a chemotherapeutic's cytotoxic side effects on T lymphocytes. However, antibodies of the invention may also exert an effect simply by binding to GT468 on the cell surface, thus, e.g. blocking proliferation of the cells.

Antibody-Dependent Cell-Mediated Cytotoxicity

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Production of Antibodies

Antibodies of the invention can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies directed against GT468 can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined strategy e.g. see Babcock et al., 1996; A novel strategy for generating monoclonal antibodies from single, isolated lymphocytes producing antibodies of defined strategy. For details of recombinant antibody engineering see also Welschof and Kraus, Recombinant antibodes for cancer therapy ISBN-0-89603-918-8 and Benny K. C. Lo Antibody Engineering ISBN 1-58829-092-1.

Immunizations

To generate antibodies to GT468, mice can be immunized with carrier-conjugated peptides derived from the GT468 sequence, an enriched preparation of recombinantly expressed GT468 antigen or fragments thereof and/or cells expressing GT468, as described. Alternatively, mice can be immunized with DNA encoding full length human GT468 (e.g. SEQ ID NO: 1) or fragments thereof, in particular those encoding SEQ ID Nos:3-10 and 35-79. In the event that immunizations using a purified or enriched preparation of the GT468 antigen do not result in antibodies, mice can also be immunized with cells expressing GT468, e.g., a cell line, to promote immune responses.

The immune response can be monitored over the course of the immunization protocol with plasma and serum samples being obtained by tail vein or retroorbital bleeds. Mice with sufficient titers of anti-GT468 immunoglobulin can be used for fusions. Mice can be boosted intraperitoneally or intravenously with GT468 expressing cells 3 days before sacrifice and removal of the spleen to increase the rate of specific antibody secreting hybridomas.

Generation of Hybridomas Producing Monoclonal Antibodies

To generate hybridomas producing monoclonal antibodies to GT468, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using GT468 expressing cells, antibodies with specificity for GT468 can be identified. The antibody secreting hybridomas can be replated, screened again, and if still positive for anti-GT468 monoclonal antibodies can be subcloned by limiting dilution. The stable subclones can then be cultured in vitro to generate antibody in tissue culture medium for characterization.

Generation of Transfectomas Producing Monoclonal Antibodies

Antibodies of the invention also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Use of Partial Antibody Sequences to Express Intact Antibodies (i.e. Humanization and Chimerisation).

a) Chimerization

Murine monoclonal antibodies can be used as therapeutic antibodies in humans when labeled with toxins or radioactive isotopes. Nonlabeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

b) Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequences spanning the CDR regions are typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed chimerized or humanized heavy and light chain variable regions are then combined with cloned promoter, leader, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains. Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric IgG1, Kappa or IgG4, Kappa antibodies. Similar plasmids can be constructed for expression of other heavy chain isotypes, or for expression of antibodies comprising lambda light chains.

Thus, in another aspect of the invention, the structural features of the anti-GT468 antibodies of the invention, are used to create structurally related humanized anti-GT468 antibodies that retain at least one functional property of the antibodies of the invention, such as binding to GT468. More specifically, one or more CDR regions of mouse monoclonal antibodies can be combined recombinantly with known human framework regions and CDRs to create additional, recombinantly-engineered, humanized anti-GT468 antibodies of the invention.

Binding to Antigen Expressing Cells

The ability of the antibody to bind GT468 can be determined using standard binding assays, such as those set forth in the examples (e.g., ELISA, Western Blot, Immunofluorescence and flow cytometric analysis)

Characterization of Binding of Antibodies

To purify anti-GT468 antibodies, selected hybridomas can be grown in two-liter spinner-flasks for monoclonal antibody purification. Alternatively, anti-GT468 antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-GT468 monoclonal antibodies bind to unique epitopes, site-directed or multi-site directed mutagenesis can be used.

Isotype Determination

To determine the isotype of purified antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

Flow Cytometric Analysis

In order to demonstrate presence of anti-GT468 antibodies in sera of immunized mice or binding of monoclonal antibodies to living cells expressing GT468, flow cytometry can be used. Cell lines expressing naturally or after transfection GT468 and negative controls lacking GT468 expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to GT468-bound monoclonal antibody under the same conditions as the primary antibody staining. The samples can be analyzed by flow cytometry with a FACS instrument using light and side scatter properties to gate on single, living cells. In order to distinguish GT468-specific monoclonal antibodies from non-specific binders in a single measurement, the method of co-transfection can be employed. Cells transiently transfected with plasmids encoding GT468 and a fluorescent marker can be stained as described above. Transfected cells can be detected in a different fluorescence channel than antibody-stained cells. As the majority of transfected cells express both transgenes, GT468-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

Immunofluorescence Microscopy

In order to demonstrate presence of anti-GT468 antibodies in sera of immunized mice or binding of monoclonal antibodies to living cells expressing GT468, immunofluorescence microscopy analysis can be used. For example, cell lines expressing either spontaneously or after transfection GT468 and negative controls lacking GT468 expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against GT468 for 30 min. at 25° C. After washing, cells can be reacted with an Alexa555-labelled anti-mouse IgG secondary antibody (Molecular Probes) under the same conditions. Cells can then be examined by fluorescence microscopy.

Total GT468 levels in cells can be observed when cells are methanol fixed or paraformaldehyde fixed and permeabilized with Triton X-100. In living cells and non-permeabilized, paraformaldehyde fixed cells surface localization of GT468 can be examined. Additionally targeting of GT468 to tight junctions can be analyzed by co-staining with tight junction markers such as ZO-1. Furthermore, effects of antibody binding and GT468 localization within the cell membrane can be examined.

Western Blot

Anti-GT468 IgG can be further tested for reactivity with GT468 antigen by Western Blotting. Briefly, cell extracts from cells expressing GT468 and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Immunohistochemistry

Anti-GT468 mouse IgGs can be further tested for reactivity with GT468 antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection GT468. For immunostaining, antibodies reactive to GT468 can be incubated followed by horseradish-peroxidase conjugated goat anti-mouse or goat anti-rabbit antibodies (DAKO) according to the vendors instructions.

Phagocytic and Cell Killing Activities of Antibodies In Vitro

In addition to binding specifically to GT468, anti-GT468 antibodies can be tested for their ability to mediate phagocytosis and killing of cells expressing GT468 and/or being characterized by association of GT468 with their cell surface. The testing of monoclonal antibody activity in vitro will provide an initial screening prior to testing in vivo models.

Antibody Dependent Cell-Mediated Cytotoxicity (ADCC):

Briefly, polymorphonuclear cells (PMNs), NK cells, monocytes, mononuclear cells or other effector cells, from healthy donors can be purified by Ficoll Hypaque density centrifugation, followed by lysis of contaminating erythrocytes. Washed effector cells can be suspended in RPMI supplemented with 10% heat-inactivated fetal calf serum or, alternatively with 5% heat-inactivated human serum and mixed with $^{51}$Cr labeled target cells expressing GT468 and/or being characterized by association of GT468 with their cell surface, at various ratios of effector cells to target cells. Alternatively, the target cells may be labeled with a fluorescence enhancing ligand (BATDA). A highly fluorescent chelate of Europium with the enhancing ligand which is released from dead cells can be measured by a fluorometer. Another alternative technique may utilize the transfection of target cells with luciferase. Added lucifer yellow may then be oxidated by viable cells only. Purified anti-GT468 IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}$Cr release or the presence of the EuTDA chelate in the culture supernatant. Alternatively, luminescence resulting from the oxidation of lucifer yellow can be a measure of viable cells.

Anti-GT468 monoclonal antibodies can also be tested in various combinations to determine whether cytolysis is enhanced with multiple monoclonal antibodies.

Complement Dependent Cytotoxicity (CDC):

Monoclonal anti-GT468 antibodies can be tested for their ability to mediate CDC using a variety of known techniques. For example, serum for complement can be obtained from blood in a manner known to the skilled person. To determine the CDC activity of mAbs, different methods can be used. $^{51}$Cr release can for example be measured or elevated membrane permeability can be assessed using a propidium iodide (PI) exclusion assay. Briefly, target cells can be washed and $5\times10^5$/ml can be incubated with various concentrations of mAb for 10-30 min. at room temperature or at 37° C. Serum or plasma can then be added to a final concentration of 20% (v/v) and the cells incubated at 37° C. for 20-30 min. All cells from each sample can be added to the PI solution in a FACS tube. The mixture can then be analyzed immediately by flow cytometry analysis using FACSArray.

In an alternative assay, induction of CDC can be determined on adherent cells. In one embodiment of this assay, cells are seeded 24 h before the assay with a density of $3\times10^4$/well in tissue-culture flat-bottom microtiter plates. The next day growth medium is removed and the cells are incubated in triplicates with antibodies. Control cells are incubated with growth medium or growth medium containing 0.2% saponin for the determination of background lysis and maximal lysis, respectively. After incubation for 20 min. at room temperature supernatant is removed and 20% (v/v) human plasma or serum in DMEM (prewarmed to 37° C.) is added to the cells and incubated for another 20 min. at 37° C. All cells from each sample are added to propidium iodide solution (10 µg/ml). Then, supernatants are replaced by PBS containing 2.5 µg/ml ethidium bromide and fluorescence emission upon excitation at 520 nm is measured at 600 nm using a Tecan Safire. The percentage specific lysis is calculated as follows: % specific lysis=(fluorescence sample-fluorescence background)/(fluorescence maximal lysis-fluorescence background)×100.

Inhibition of Cell Proliferation by Monoclonal Antibodies:

To test for the ability to initiate apoptosis, monoclonal anti-GT468 antibodies can, for example, be incubated with GT468 positive tumor cells or GT468 transfected tumor cells at 37° C. for about 20 hours. The cells can be harvested, washed in Annexin-V binding buffer (BD biosciences), and incubated with Annexin V conjugated with FITC or APC (BD biosciences) for 15 min. in the dark. All cells from each sample can be added to PI solution (10 µg/ml in PBS) in a FACS tube and assessed immediately by flow cytometry (as above).

Alternatively, a general inhibition of cell-proliferation by monoclonal antibodies can be detected with commercially available kits. The DELFIA Cell Proliferation Kit (Perkin-Elmer, Cat. No. AD0200) is a non-isotopic immunoassay based on the measurement of 5-bromo-2'-deoxyuridine (BrdU) incorporation during DNA synthesis of proliferating cells in microplates. Incorporated BrdU is detected using europium labelled monoclonal antibody. To allow antibody detection, cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Preclinical Studies

Monoclonal antibodies which bind to GT468 also can be tested in an in vivo model (e.g. in immune deficient mice carrying xenografted tumors inoculated with cell lines expressing GT468, possibly after transfection) to determine their efficacy in controlling growth of GT468-expressing tumor cells.

In vivo studies after xenografting GT468 expressing tumor cells into immunocompromised mice or other animals can be performed using antibodies of the invention. Antibodies can be adminstered to tumor free mice followed by injection of tumor cells to measure the effects of the antibodies to prevent formation of tumors or tumor-related symptoms. Antibodies can be adminstered to tumor-bearing mice to determine the therapeutic efficacy of respective antibodies to reduce tumor growth, metastasis or tumor related symptoms. Antibody application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibodies of the invention animals can be inoculated with antibodies or control reagents and thoroughly investigated for symptoms possibly related to GT468-antibody therapy. Possible side effects of in vivo application of GT468 antibodies particularly include toxicity at GT468 expressing tissues including placenta. Antibodies recognizing GT468 in human and in other species, e.g. mice, are particularly useful to predict potential side effects mediated by application of monoclonal GT468-antibodies in humans.

Epitope Mapping

Mapping of epitopes recognized by antibodies of invention can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

I. Bispecific/Multispecific Molecules which Bind to GT468

In yet another embodiment of the invention, antibodies to GT468 can be derivatized or linked to another functional molecule, e.g., another peptide or protein (e.g., an Fab' fragment) to generate a bispecific or multispecific molecule which binds to multiple binding sites or target epitopes. For example, an antibody of the invention can be functionally linked (e.g. by chemical coupling, genetic fusion, noncovalent association or otherwise) to one or more other binding molecules, such as another antibody, peptide or binding mimetic.

Accordingly, the present invention includes bispecific and multispecific molecules comprising at least one first binding specificity for GT468 and a second binding specificity for a second target epitope. In a particular embodiment of the invention, the second target epitope is an Fc receptor, e.g. human Fc-gammaRI (CD64) or a human Fc-alpha receptor (CD89), or a T cell receptor, e.g. CD3. Therefore, the invention includes bispecific and multispecific molecules capable of binding both to Fc-gammaR, Fc-alphaR or Fc-epsilonR expressing effector cells (e.g. monocytes, macrophagesor polymorphonuclear cells (PMNs)), and to target cells expressing GT468 and/or being characterized by association of GT468 with their cell surface. These bispecific and multispecific molecules may target cells expressing GT468 and/or being characterized by association of GT468 with their cell surface to effector cells and may trigger Fc receptor-mediated effector cell activities, such as phagocytosis of cells expressing GT468 and/or being characterized by association of GT468 with their cell surface, antibody dependent cellular cytotoxicity (ADCC), cytokine release, or generation of superoxide anion.

Bispecific and multispecific molecules of the invention can further include a third binding specificity, in addition to an anti-Fc binding specificity and an anti-GT468 binding specificity. In one embodiment, the third binding specificity is an anti-enhancement factor (EF) portion, e.g. a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al., U.S. Pat. No. 4,946,778. The antibody may also be a binding-domain immunoglobulin fusion protein as disclosed in US2003/0118592 and US 2003/0133939.

In one embodiment bispecific and multispecific molecules of the invention comprise a binding specificity for an Fc-gammaR or an Fc-alphaR present on the surface of an effector cell, and a second binding specificity for a target cell antigen, e.g., GT468.

In one embodiment, the binding specificity for an Fc receptor is provided by a monoclonal antibody, the binding of which is not blocked by human immunoglobulin G (IgG). As used herein, the term "IgG receptor" refers to any of the eight gamma-chain genes located on chromosome 1. These genes encode a total of twelve transmembrane or soluble receptor isoforms which are grouped into three Fc-gamma receptor classes: Fc-gammaRI (CD64), Fe-gammaRII (CD32), and Fc-gammaRIII (CD16). In one preferred embodiment, the Fc-gamma receptor is a human high affinity Fc-gammaRI.

The production and characterization of these preferred monoclonal antibodies are described by Fanger et al. in WO 88/00052 and in U.S. Pat. No. 4,954,617. These antibodies bind to an epitope of Fc-gammaRI, Fc-gammaRII or Fc-gammaRIII at a site which is distinct from the Fcγ binding site of the receptor and, thus, their binding is not blocked substantially by physiological levels of IgG. Specific anti-Fc-gammaRI antibodies useful in this invention are mAb 22, mAb 32, mAb 44, mAb 62 and mAb 197. In other embodiments, the anti-Fcγ receptor antibody is a humanized form of monoclonal antibody 22 (H22). The production and characterization of the H22 antibody is described in Graziano, R. F. et al. (1995) J. Immunol. 155 (10): 4996-5002 and WO 94/10332. The H22 antibody producing cell line was deposited at the American Type Culture Collection on Nov. 4, 1992 under the designation HA022CL1 and has the accession No. CRL 11177.

In still other preferred embodiments, the binding specificity for an Fc receptor is provided by an antibody that binds to a human IgA receptor, e.g., an Fc-alpha receptor (Fc-alphaRI (CD89)), the binding of which is preferably not blocked by human immunoglobulin A (IgA). The term "IgA receptor" is intended to include the gene product of one alpha-gene (Fc-alphaRI) located on chromosome 19. This gene is known to encode several alternatively spliced transmembrane isoforms of 55 to 110 kDa. Fc-alphaRI (CD89) is constitutively expressed on monocytes/macrophages, eosinophilic and neutrophilic granulocytes, but not on non-effector cell populations. Fc-alphaRI has medium affinity for both IgA1 and IgA2, which is increased upon exposure to cytokines such as G-CSF or GM-CSF (Morton, H. C. et al. (1996) Critical Reviews in Immunology 16: 423-440). Four Fc-alphaRI-specific monoclonal antibodies, identified as A3, A59, A62 and A77, which bind Fc-alphaRI outside the IgA ligand binding domain, have been described (Monteiro, R. C. et al. (1992) J. Immunol. 148: 1764).

Fc-alphaRI and Fc-gammaRI are preferred trigger receptors for use in the invention because they (1) are expressed primarily on immune effector cells, e.g., monocytes, PMNs, macrophages and dendritic cells; (2) are expressed at high levels (e.g., 5,000-100,000 per cell); (3) are mediators of cytotoxic activities (e.g., ADCC, phagocytosis); (4) mediate enhanced antigen presentation of antigens, including self-antigens, targeted to them.

In another embodiment the bispecific molecule is comprised of two monoclonal antibodies according to the invention which have complementary functional activities, such as one antibody predominately working by inducing CDC and the other antibody predominately working by inducing apoptosis.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include cells of myeloid or lymphoid origin, e.g, lymphocytes (e.g., B cells and T cells including cytolytic T cells (CTLs), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cellular cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of Fc-gammaRI has been found to be up-regulated by interferon gamma (IFN-γ). This enhanced expression increases the cytotoxic activity of Fc-gammaRI-bearing cells against targets. An effector cell can phagocytose or lyse a target antigen or a target cell.

"Target cell" shall mean any undesirable cell in a subject (e.g., a human or animal) that can be targeted by an antibody of the invention. In preferred embodiments, the target cell is a cell expressing or overexpressing GT468 and/or being characterized by association of GT468 with its cell surface. Cells expressing GT468 and/or being characterized by association of GT468 with their cell surface typically include tumor cells.

Bispecific and multispecific molecules of the present invention can be made using chemical techniques (see e.g., D. M. Kranz et al. (1981) Proc. Natl. Acad. Sci. USA 78:5807), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-FcR and anti-GT468 binding specificities, using methods known in the art. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl-4-(N-maleimidomethyl)cyclohexane-1-carboxylate (sulfo-SMCC) (see e.g., Karpovsky et al. (1984) J. Exp. Med. 160: 1686; Liu, M A et al. (1985) Proc. Natl. Acad. Sci. USA 82: 8648). Other methods include those described by Paulus (Behring Ins. Mitt. (1985) No. 78, 118-132); Brennan et al. (Science (1985) 229: 81-83), and Glennie et al. (J. Immunol. (1987) 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb× Fab, Fab×F(ab')$_2$ or ligand×Fab fusion protein. A bispecific and multispecific molecule of the invention, e.g., a bispecific molecule, can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ-counter or a scintillation counter or by autoradiography.

II. Immunoconjugates

In another aspect, the present invention features an anti-GT468 antibody conjugated to a therapeutic moiety or agent, such as a cytotoxin, a drug (e.g., an immunosuppressant) or a radioisotope. Such conjugates are referred to herein as "immunoconjugates". Immunoconjugates which include one or more cytotoxins are referred to as "immunotoxins". A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the invention include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies of the present invention also can be conjugated to a radioisotope, e.g., iodine-131, yttrium-90 or indium-111, to generate cytotoxic radiopharmaceuticals for treating a GT468-related disorder, such as a cancer. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

In a further embodiment, the antibodies according to the invention are attached to a linker-chelator, e.g., tiuxetan, which allows for the antibody to be conjugated to a radioisotope.

III. Pharmaceutical Compositions

In another aspect, the present invention provides a composition, e.g., a pharmaceutical composition, containing one or a combination of antibodies of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. In one embodiment, the compositions include a combination of multiple (e.g., two or more) isolated antibodies of the invention which act by different mechanisms, e.g., one antibody which predominately acts by inducing CDC in combination with another antibody which predominately acts by inducing apoptosis.

Pharmaceutical compositions of the invention also can be administered in combination therapy, i.e., combined with other agents. For example, the combination therapy can include a composition of the present invention with at least one anti-inflammatory agent or at least one immunosuppressive agent. In one embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib (Vioxx) and celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin).

In another embodiment, such therapeutic agents include agents leading to the depletion or functional inactivation of regulatory T cells like low dose cyclophosphamid, anti-CTLA4 antibodies, anti-IL2 or anti-IL2-receptor antibodies.

In yet another embodiment, such therapeutic agents include one or more chemotherapeutics, such as Taxol derivatives, taxotere, gemcitabin, 5-Fluoruracil, doxorubicin (Adriamycin), cisplatin (Platinol), cyclophosphamide (Cytoxan, Procytox, Neosar). In another embodiment, antibodies of the present invention may be administered in combination with chemotherapeutic agents, which preferably show therapeutic efficacy in patients suffering from breast, lung, gastric and/or ovarian cancer, or other cancer types e.g. as described herein.

In yet another embodiment, the antibodies of the invention may be administered in conjunction with radiotherapy and/or autologous peripheral stem cell or bone marrow transplantation.

In still another embodiment, the antibodies of the invention may be administered in combination with one or more antibodies selected from anti-CD25 antibodies, anti-EPCAM antibodies, anti-EGFR, anti-Her2/neu, and anti-CD40 antibodies.

In yet a further embodiment, the antibodies of the invention may be administered in combination with an anti-C3b(i) antibody in order to enhance complement activation.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19).

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like.

Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J. Neuroimmunol. 7: 27).

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Generally, out of one hundred percent, this amount will range from about 0.01 percent to about ninety-nine percent of active ingredient, preferably from about 0.1 percent to about 70 percent, most preferably from about 1 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In one embodiment the monoclonal antibodies of the invention are administered in crystalline form by subcutaneous injection, cf. Yang et al. (2003) PNAS, 100 (12): 6934-6939. When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

In one embodiment, the antibodies of the invention may be administered by infusion, preferably slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months. The dosage can be determined or adjusted by measuring the amount of circulating monoclonal anti-GT468 antibodies upon administration in a biological sample by using anti-idiotypic antibodies which target the anti-GT468 antibodies.

In yet another embodiment, the antibodies are administered by maintenance therapy, such as, e.g., once a week for a period of 6 months or more.

In still another embodiment, the antibodies according to the invention may be administered by a regimen including one infusion of an antibody against GT468 followed by an infusion of an antibody against GT468 conjugated to a radioisotope. The regimen may be repeated, e.g., 7 to 9 days later.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art. In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. No. 4,522,811; U.S. Pat. No. 5,374,548; and U.S. Pat. No. 5,399,331. The liposomes may comprise one or more moieties which are selectively transported into specific cells or organs, and thus enhance targeted drug delivery (see, e.g., V. V. Ranade (1989) J. Clin. Pharmacol. 29: 685). Exemplary targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); and surfactant protein A receptor (Briscoe et al. (1995) Am. J. Physiol. 1233: 134).

In one embodiment of the invention, the therapeutic compounds of the invention are formulated in liposomes. In a more preferred embodiment, the liposomes include a targeting moiety. In a most preferred embodiment, the therapeutic compounds in the liposomes are delivered by bolus injection to a site proximal to the desired area, e.g., the site of a tumor. The composition must be fluid to the extent that easy syringability exists. It must be stable under the conditions of manufacture and storage and must be preserved against the contaminating action of microorganisms such as bacteria and fungi.

In a further embodiment, antibodies of the invention can be formulated to prevent or reduce their transport across the placenta. This can be done by methods known in the art, e.g., by PEGylation of the antibodies or by use of F(ab)2' fragments. Further references can be made to "Cunningham- Rundles C, Zhuo Z, Griffith B, Keenan J. (1992) Biological activities of polyethylene-glycol immunoglobulin conjugates. Resistance to enzymatic degradation. J. Immunol. Methods, 152: 177-190; and to "Landor M. (1995) Maternal-fetal transfer of immunoglobulins, Ann. Allergy Asthma Immunol. 74: 279-283.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. Alternatively, this property of a composition can be evaluated by examining the ability of the compound to inhibit cell growth or apoptosis by in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

IV. Uses and Methods of the Invention

The antibodies (including immunoconjugates, bispecifics/multispecifics, compositions and other derivatives described herein) of the present invention have numerous therapeutic utilities involving the treatment of disorders involving cells expressing GT468 and/or being characterized by association of GT468 with their cell surface. For example, the antibodies can be administered to cells in culture, e.g., in vitro or ex vivo, or to human subjects, e.g., in vivo, to treat or prevent a variety of disorders such as those described herein. As used herein, the term "subject" is intended to include human and non-human animals which respond to the antibodies against GT468. Preferred subjects include human patients having disorders that can be corrected or ameliorated by killing diseased cells, in particular cells characterized by an altered expression pattern of GT468 and/or an altered pattern of association of GT468 with their cell surface compared to normal cells.

A therapeutic effect in the treatments discussed herein is preferably achieved through the functional properties of the antibodies of the invention to mediate killing of cells e.g. by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis.

For example, in one embodiment, antibodies of the present invention can be used to treat a subject with a tumorigenic disorder, e.g., a disorder characterized by the presence of tumor cells expressing GT468 and/or being characterized by association of GT468 with their cell surface including, for example, breast cancer. Examples of tumorigenic diseases which can be treated and/or prevented encompass all GT468 expressing cancers and tumor entities including breast cancer, lung cancer, gastric cancer, ovarian cancer, hepatocellular cancer, colon cancer, pancreatic cancer, esophageal cancer, head & neck cancer, kidney cancer, prostate cancer, and liver cancer. These cancers may be in early, intermediate or advanced stages, e.g. metastasis.

The pharmaceutical compositions and methods of treatment described according to the invention may also be used for immunization or vaccination to prevent a disease described herein.

In another embodiment, antibodies of the invention can be used to detect levels of GT468 or particular forms of GT468, or levels of cells which contain GT468 on their membrane surface, which levels can then be linked to certain diseases or disease symptoms such as described above. Alternatively, the antibodies can be used to deplete or interact with the function of cells expressing GT468 and/or being characterized by association of GT468 with their cell surface, thereby implicating these cells as important mediators of the disease. This can be achieved by contacting a sample and a control sample with the anti-GT468 antibody under conditions that allow for the formation of a complex between the antibody and GT468. Any complexes formed between the antibody and GT468 are detected and compared in the sample and a control sample, i.e. a reference sample.

Antibodies of the invention can be initially tested for their binding activity associated with therapeutic or diagnostic uses in vitro. For example, the antibodies can be tested using flow cytometric assays as described herein.

Moreover, activity of the antibodies in triggering at least one effector-mediated effector cell activity, including inhibiting the growth of and/or killing of cells expressing GT468 and/or being characterized by association of GT468 with their cell surface, can be assayed. For example, the ability of the antibodies to trigger CDC and/or apoptosis can be assayed. Protocols for assaying for CDC, homotypic adhesion, molecular clustering or apoptosis are described herein.

The antibodies of the invention can be used to elicit in vivo or in vitro one or more of the following biological activities: to inhibit the growth of and/or differentiation of a cell expressing GT468 and/or being characterized by association of GT468 with its cell surface; to kill a cell expressing GT468 and/or being characterized by association of GT468 with its cell surface; to mediate phagocytosis or ADCC of a cell expressing GT468 and/or being characterized by association of GT468 with its cell surface in the presence of effector cells; to mediate CDC of a cell expressing GT468 and/or being characterized by association of GT468 with its cell surface in the presence of complement; to mediate apoptosis of a cell expressing GT468 and/or being characterized by association of GT468 with its cell surface; to induce homotypic adhesion; and/or to induce translocation into lipid rafts upon binding GT468.

In a particular embodiment, the antibodies are used in vivo or in vitro to treat, prevent or diagnose a variety of GT468-related diseases. Examples of GT468-related diseases include, among others, cancers such as breast cancer, lung cancer, gastric cancer, ovarian cancer, hepatocellular cancer, colon cancer, pancreatic cancer, esophageal cancer, head & neck cancer, kidney cancer, prostate cancer, and liver cancer.

Suitable routes of administering the antibody compositions of the invention in vivo and in vitro are well known in the art and can be selected by those of ordinary skill.

As described above, anti-GT468 antibodies of the invention can be co-administered with one or other more therapeutic agents, e.g., a cytotoxic agent, a radiotoxic agent, antiangiogenic agent or and immunosuppressive agent to reduce the induction of immune responses against the antibodies of invention. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as listed above. Co-administration of the anti-GT468 antibodies of the present invention with chemotherapeutic agents provides two anti-cancer agents which operate via different mechanisms yielding a cytotoxic effect to tumor cells. Such co-administration can solve problems due to development of resistance to drugs or a change in the antigenicity of the tumor cells which would render them unreactive with the antibody.

In another particular embodiment of the invention, the subject being administered the antibody is additionally treated with an antiagionic agent including antibodies targeting VEGF or VEGFR and one or more chemical compounds inhibiting angiogenesis. Pretreatment with or parallel application of these drugs may improve the penetration of antibodies in bulk tumors.

In another particular embodiment of the invention, the subject being administered the antibody is additionally treated with a compound inhibiting growth factor receptor signaling including monoclonal antibodies binding to the EGFR receptor as well as chemical compounds inhibiting signaling initiated by the EGFR, Her1 or Her2/neu receptor.

Target-specific effector cells, e.g., effector cells linked to compositions (e.g. antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$ to $10^9$ but will vary depending on the therapeutic purpose. In general, the amount will be sufficient to obtain localization at the target cell, e.g., a tumor cell expressing GT468 and/or being characterized by association of GT468 with its cell surface, and to effect cell killing by, e.g., phagocytosis. Routes of administration can also vary.

Therapy with target-specific effector cells can be performed in conjunction with other techniques for removal of targeted cells. For example, anti-tumor therapy using the compositions of the invention and/or effector cells armed with these compositions can be used in conjunction with chemotherapy. Additionally, combination immunotherapy may be used to direct two distinct cytotoxic effector populations toward tumor cell rejection. For example, anti-GT468 antibodies linked to anti-Fc-RI or anti-CD3 may be used in conjunction with IgG- or IgA-receptor specific binding agents.

Bispecific and multispecific molecules of the invention can also be used to modulate Fc-gammaR or Fc-alphaR levels on effector cells, such as by capping and eliminating receptors on the cell surface. Mixtures of anti-Fc receptors can also be used for this purpose.

The compositions (e.g., antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions of the invention can also be lysed by complement. In yet another embodiment, the compositions of the invention do not activate complement.

The compositions of the invention can also be administered together with complement. Accordingly, within the scope of the invention are compositions comprising antibodies, multispecific or bispecific molecules and serum or complement. These compositions are advantageous in that the complement is located in close proximity to the antibodies, multispecific or bispecific molecules.

Alternatively, the antibodies, multispecific or bispecific molecules of the invention and the complement or serum can be administered separately. Binding of the compositions of the present invention to target cells may cause translocation of the GT468 antigen-antibody complex into lipid rafts of the cell membrane. Such translocation creates a high density of antigen-antibody complexes which may efficiently activate and/or enhance CDC.

Also within the scope of the present invention are kits comprising the antibody compositions of the invention (e.g., antibodies and immunoconjugates) and instructions for use. The kit can further contain one or more additional reagents, such as an immunosuppressive reagent, a cytotoxic agent or a radiotoxic agent, or one or more additional antibodies of the invention (e.g., an antibody having a complementary activity).

Accordingly, patients treated with antibody compositions of the invention can be additionally administered (prior to, simultaneously with, or following administration of a antibody of the invention) with another therapeutic agent, such as a cytotoxic or radiotoxic agent, which enhances or augments the therapeutic effect of the antibodies of the invention.

In other embodiments, the subject can be additionally treated with an agent that modulates, e.g., enhances or inhibits, the expression or activity of Fc-gamma or Fc-alpha receptors by, for example, treating the subject with a cytokine. Preferred cytokines include granulocyte colony-stimulating factor (G-CSF), granulocyte-macrophage colony-stimulating factor (GM-CSF), interferon-γ (IFN-γ), and tumor necrosis factor (TNF). Other important agents for increasing the therapeutic efficacy of the antibodies and pharmaceutical compositions described herein are β-glucans which are homopolysaccharides of branched glucose residues and are produced by a variety of plants and microorganisms, for example, bacteria, algae, fungi, yeast and grains. Fragments of β-glucans produced by organisms may be also be used. Preferably, the β-glucan is a polymer of β(1,3) glucose wherein at least some of the backbone glucose units, e.g. 3-6% of the backbone glucose units, possess branches such as β(1,6) branches.

In a particular embodiment, the invention provides methods for detecting the presence of GT468 antigen in a sample, or measuring the amount of GT468 antigen, comprising contacting the sample, and a control sample, with a antibody which specifically binds to GT468, under conditions that allow for formation of a complex between the antibody or portion thereof and GT468. The formation of a complex is then detected, wherein a difference complex formation between the sample compared to the control sample is indicative for the presence of GT468 antigen in the sample.

In still another embodiment, the invention provides a method for detecting the presence or quantifying the amount of cells expressing GT468 and/or being characterized by association of GT468 with their cell surface in vivo or in vitro. The method comprises (i) administering to a subject a composition of the invention conjugated to a detectable marker; and (ii) exposing the subject to a means for detecting said detectable marker to identify areas containing cells expressing GT468 and/or being characterized by association of GT468 with their cell surface.

Methods as described above are useful, in particular, for diagnosing GT468-related diseases and/or the localization of GT468-related diseases such as cancer diseases. Preferably an amount of GT468 in a sample which is higher than the amount of GT468 in a control sample is indicative for the presence of a GT468-related disease in a subject, in particular a human, from which the sample is derived.

In yet another embodiment immunoconjugates of the invention can be used to target compounds (e.g., therapeutic agents, labels, cytotoxins, radiotoxins immunosuppressants, etc.) to cells which have GT468 associated with their surface by linking such compounds to the antibody. Thus, the invention also provides methods for localizing ex vivo or in vitro cells expressing GT468 and/or being characterized by association of GT468 with their cell surface, such as circulating tumor cells.

The present invention is further illustrated by the following examples which are not be construed as limiting the scope of the invention.

EXAMPLES

Example 1

Materials and Methods

The techniques and methods mentioned herein are carried out in a manner known per se and as described, for example, in Sambrook et al., Molecular Cloning: A Laboratory Manual, 2nd Edition (1989) Cold Spring Harbor Laboratory Press, Cold Spring Harbor, N.Y, or as described below. All methods including the use of kits and reagents are carried out according to the manufacturers' information.

Tissues and Cell Lines

Recombinant DNA work was done with the official permission and according to the rules of the state government of Rheinland-Pfalz. Tissues were obtained as human surplus materials during routine diagnostic or therapeutic procedures and were stored at −80° C. until use. Breast cancer cell lines MCF-7 and BT549 were cultured in DMEM/10% FCS.

RNA-Isolation, RT-PCR and Real-Time RT-PCR

RNA extraction, first-strand cDNA synthesis, RT-PCR and real-time RT-PCR were performed as previously described (Koslowski, M., Sahin, U., Huber, C. & Tureci, O. (2006) *Hum. Mol. Genet.* 15, 2392-2399). For end-point analysis GT468-specific oligonucleotides (sense 5'-AAA TTT GGC AGC TGC CTT CAC-3'; antisense 5'-TGA TGC CAC ATT CAG TAA CAC-3', 60° C. annealing) were used in a 35 cycle RT-PCR. Real-time quantitative expression analysis was performed in triplicates in a 40 cycle RT-PCR. After normalization to HPRT (sense 5'-TGA CAC TGG CAA AAC AAT GCA-3'; antisense 5'-GGT CCT TTT CAC CAG CAA GCT-3', 62° C. annealing) GT468 transcripts in tumor samples were quantified relative to normal tissues using ΔΔCT calculation. Specificity of PCR reactions was confirmed by cloning and sequencing of amplification products from arbitrarily selected samples.

Bioinformatics

For in silico cloning of trophoblast-specific molecules a data mining strategy described in detail elsewhere was modified and adapted (Koslowski, M., Bell, C., Seitz, G., Lehr, H. A., Roemer, K., Muntefering, H., Huber, C., Sahin, U. & Tureci, O. (2004) *Cancer Res.* 64, 5988-5993; Koslowski, M., Tureci, O., Bell, C., Krause, P., Lehr, H. A., Brunner, J., Seitz, G., Nestle, F. O., Huber, C. & Sahin, U. (2002) *Cancer Res.* 62, 6750-6755; Koslowski, M., Sahin, U., Huber, C. & Tureci, O. (2006) *Hum. Mol. Genet.* 15, 2392-2399). Briefly, hierarchical keyword search of GenBank was combined with digital cDNA-library subtraction.

For keyword search nucleotide sequence files at GenBank were accessed for genes annotated to be specifically expressed in placenta or trophoblast tissue using the ENTREZ Search and Retrieval System (available at the NCBI website). The sequence homology-searching program BLASTN (available at the NCBI website) was run sequentially for each nucleotide sequence against all of the human nucleotide sequences to prevent redundancies. As a second filter electronic Northern (eNorthern) was performed for all clones obtained by keyword search by BLAST search of each DNA sequences of interest against EST database at the NCBI website. It was taken into consideration that several cDNA libraries in the public domain are not properly annotated (Scheurle, D., DeYoung, M. P., Binninger, D. M., Page, H., Jahanzeb, M. & Narayanan, R. (2000) *Cancer Res.* 60, 4037-4043).

For digital subtraction the cDNA xProfiler tool of the Cancer Genome Anatomy Project at the NCBI website. It was used, which compares gene expression between two pools (A and B) of cDNA libraries where each pool can be either a single library or several libraries. The search options for Pool A and Pool B were set to "*Homo sapiens*" for Organism and "all EST libraries" for Library Group to search all cDNA libraries in dbEST. All cDNA libraries prepared from placenta and trophoblast tissue matching the search option settings were assigned to Pool A excluding mixed tissue libraries. For Pool B all cDNA libraries prepared from normal tissues except placenta, trophoblast, testis, ovary and whole body fetus were selected.

For analysis of the GT468 promotor region EMBOSS CpGPlot (Rice, P., Longden, I. & Bleasby, A. (2000) *Trends Genet.* 16, 276-277) software was used. Moreover, analysis of the GT468 protein sequence was conducted with MEMSAT3 (Jones, D. T., Taylor, W. R. & Thornton, J. M. (1994) *Biochemistry* 33, 3038-3049), TMpred (Hofmann, K. & Stoffel, W. (1993) *Biol. Chem. Hoppe-Seyler* 374, 166), and GOR IV (Garnier, J., Osguthorpe, D. J. & Robson, B. (1978) *J. Mol. Biol.* 120, 97-120).

Antisera, Immunofluorescence and Immunochemistry

The polyclonal antiserum raised against aa 117-127 of GT468 was generated by a custom antibody service (Squarix, Marl, Germany). Immunohistochemistry was performed on tissue cryosections using the VECTOR Nova-RED Substrate Kit (Vector, Burlingame, Calif.) according to the manufacturer's instructions. For Western blot analysis 30 µg of total protein extracted from cells lyzed with Triton-X was used. Extracts were diluted in reducing sample buffer (Roth, Karlsruhe, Germany), subjected to SDS-PAGE and subsequently electrotransferred onto PVDF membrane (Pall, East Hills, N.Y.). Immunostaining was performed with antibodies reactive to pAKT (Cell Signaling, Danvers, Mass.), AKT (Cell Signaling, Danvers, Mass.), cyclin D1 (Santa Cruz Biotechnology, Santa Cruz, Calif.) and beta-Actin (Abcam, Cambridge, UK) followed by detection of primary antibody with horseradish-peroxidase conjugated goat anti-mouse and goat anti-rabbit secondary antibodies (Dako, Glostrup, Denmark).

siRNA Duplexes

The GT468 siRNA duplex (Qiagen, Hilden, Germany) (sense 5'-r(CCA UGA GAG UAG CCA GCA)dTdT-3', antisense 5'-r(UUG CUG GCU ACU CUC AUG G)dAdG-3') targeted nucleotides 670-690 of the GT468 mRNA sequence (NM_021796.3). As control a scrambled siRNA duplex (sense 5'-r(UAA CUG UAU AAU CGA CUA G)dTdT-5', antisense 5'-r(CUA GUC GAU UAU ACA GUU A)dGdA-3') was used. For GT468 silencing studies cells were transfected with 10 nM siRNA duplex using HiPerFect transfection reagent (Qiagen) according to the manufacturer's instructions. All results were reproduced with a second set of GT468 siRNA duplexes (sense 5'-r(GGU UCA GGA CAA AGU CCA A)dTdT-3', antisense 5'-r(UUG GAC UUU GUC CUG AAC C)dGdG-3') targeting nucleotides 342-362.

Cell Proliferation Analysis Following Transfection of siRNA 24 h after transfection with siRNA duplexes $1 \times 10^4$ cells were cultured for 48 h in medium supplemented with 10% FCS. Proliferation was analyzed by measuring the incorporation of BrdU into newly synthesized DNA strands using the DELFIA cell proliferation Kit (Perkin Elmer, Boston, Mass.) according to the manufacturer's instructions on a Wallac Victor$^2$ multi-label counter (Perkin Elmer, Boston, Mass.).

Cell Cycle Analysis

Cells were cultured in medium supplemented with 10% FCS in varying concentrations. 72 h after transfection with siRNA duplexes cells were harvested, EtOH-fixed, and stained with propidiumiodide prior to flowcytometric DNA content analysis. Cells in the different phases of the cell cycle were quantified using CellQuest™ Pro (BD, Franklin Lakes, N.J.) and FlowJo™ (Tree Star, Ashland, Oreg.) flowcytometric analysis software. Apoptotic cells were quantified by AnnexinV staining 48 h and 72 h after siRNA transfection.

Cell Migration and In Vitro Invasion Assay

Cell migration assays were conducted in transwell chambers with 8.0 µm pore membranes (BD Biosciences, San Jose, Calif.) with cells cultured in serum-free medium for 12 h prior to experiments. For siRNA experiments cells were transferred to serum-free conditions 24 h after transfection with siRNA duplexes as described above. $4 \times 10^4$ cells in 400 µl serum-free culture medium were added to the upper chamber. The bottom chambers contained 800 µl culture medium supplemented with 5% FCS as chemoattractant. 24 h later cells that had migrated to the bottom side of the membrane were fixed in ice-cold methanol; membranes were excised, placed on microscope slides and mounted with Hoechst (Dako, Glostrup, Denmark) for fluorescence microscopy. Cells in five random visual fields (100× magnification) were counted for each membrane. All experiments were done in triplicates. Effects on chemokinesis of cells were analyzed using the same experimental setup with chemoattractant added to both the upper and lower chamber. For in vitro invasion assays the upper chambers were prepared with 100 µl of Matrigel (BD Biosciences, San Jose, N.J.) diluted to 1 mg/ml in serum free medium. Chambers were incubated at 37° C. for 5 h for gelling.

Cell Proliferation Analysis Following Incubation with Antibodies

Endogenously GT468-expressing cancer cell lines BT-549, Caov-3, EFO-21, MCF-7, and MDA-MB-231 were incubated with hybridoma supernatant diluted 1:2 in DMEM cell culture medium for 72 h. Proliferation was analyzed by measuring the incorporation of BrdU into newly synthesized DNA strands using the DELFIA cell proliferation Kit (Perkin Elmer) according to the manufacturer's instructions on a Wallac Victor2 multi-label counter (Perkin Elmer).

Alternatively, endogenously GT468-expressing cancer cell lines SK-BR-3 and MCF-7, respectively, were incubated with HPLC-purified hybridoma supernatants diluted in DMEM cell culture medium for 72 h or 120 h at concentrations as indicated. Proliferation was analyzed as described above.

Immunofluorescence Microscopy

In order to demonstrate presence of anti-GT468 antibodies in sera of immunized mice or binding of monoclonal antibodies to living cells expressing GT468, immunofluorescence microscopy analysis was used. CHO cells transfected with GT468-eGFP were grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells then were fixed with methanol or paraformaldehyde/0.1% Saponin. Cells were incubated with antibodies against GT468 for 60 min. at 25° C. After washing, cells were incubated with an Alexa555-labelled anti-mouse IgG secondary antibody (Molecular Probes) under the same conditions.

GT468 Peptide-Specific ELISA

Microwell plates (Nunc) were coated for one hour at 37° C. with the relevant GT468 peptide (5 µg/ml). Blocking was performed with PBS 3% BSA overnight at 4° C. After washing three times with PBS, the plates were loaded with hybridoma supernatants (diluted 1:5 or 1:10 in PBS 3% BSA, 50 µl per well) and incubated for 1 h at room temperature (orbital shaking at 90 rpm). Secondary antibody (HRPO-conjugated goat anti-mouse IgG, Jackson Immunoresearch) in PBS 3% BSA was added after washing three times with PBS, and incubated for 1 h at room temperature with orbital shaking at 90 rpm. After a final washing step (three times with PBS), substrate solution consisting of 1.5 mM ABTS in 100 mM sodium acetate (pH 5.2) was added. Immediately before use, the substrate solution was supplemented with 0.3 µl per ml of 30% $H_2O_2$. Absorption at 405 nm was measured on a Tecan Safire Plate reader (Tecan) after 30-60 min.

Immunizations

In the production of the clones deposited under the accession no. DSM ACC2822 (4E9-1H9), DSM ACC2826 (9B6-2A9), DSM ACC2824 (59D6-2F2), DSM ACC2825 (61C11-2B5), DSM ACC2823 (78H11-1H6), Balb/c or C57/BL6 were immunized with KLH-coupled peptides. 50 µg of peptides with 50 µl Montanide ISA 50V as adjuvant were injected intraperitoneally (i.p.) on days 1, 15, 45, and 86. The presence of antibodies directed against GT468 in sera of mice was monitored by peptide-specific ELISA on days 24, 57, and 92. Mice with detectable immune responses were boosted three days prior to splenectomy for generation of monoclonal antibodies.

In all other cases, Balb/c or C57/BL6 mice were immunized with GT468 pcDNA3.1 plasmid with PEI Mannose as adjuvant intramuscularly (i.m.) on day 1 and 15. Thereafter, 50 µg of peptides with 50 µl Montanide ISA 50V as adjuvant (intraperitoneally) or 150 µg protein with incomplete Freund's adjuvant (IFA) (subcutaneously) were injected on days 30 and 45. The presence of antibodies directed against GT468 in sera of mice was monitored by peptide-specific ELISA or CrELISA. Mice with detectable immune responses were boosted three days prior to splenectomy for generation of monoclonal antibodies.

Generation of Hybridomas Producing Human Monoclonal Antibodies to GT468

Mouse splenocytes were isolated and fused with PEG to a mouse myeloma cell line based on standard protocols. The resulting hybridomas were then screened for production of immunoglobulines with GT468 specificity using peptide-specific ELISA, GT468 CrELISA and CHO cells transfected with GT468-eGFP by IF.

Single cell suspensions of splenic lymphocytes from immunized mice were fused with P3X63Ag8U.1 nonsecreting mouse myeloma cells (ATCC, CRL 1597) in a 2:1 ratio using 50% PEG (Roche Diagnostics, CRL 738641). Cells were plated at approximately $3 \times 10^4$/well in flat bottom microtiter plates, followed by about two week incubation in selective medium containing 10% fetal bovine serum, 2% hybridoma fusion and cloning supplement (HFCS, Roche Diagnostics, CRL 1 363 735) plus 10 mM HEPES, 0.055 mM 2-mercaptoethanol, 50 µg/ml gentamycin and 1×HAT (Sigma, CRL H0262). After 10 to 14 days individual wells were screened by peptide-specific ELISA for anti-GT468 monoclonal antibodies. The antibody secreting hybridomas were replated, screened again and, if still positive for anti-GT468 monoclonal antibodies, were subcloned by limiting dilution. The stable subclones were then cultured in vitro to generate small amounts of antibody in tissue culture medium for characterization. At least one clone from each hybridoma, which retained the reactivity of parent cells (by ELISA and IF), was chosen.

Isotyping

For isotyping of hybridoma supernatants, IsoStrip Mouse Monoclonal Antibody Isotyping Kit (Roche, Cat. No. 1493027) was used as described by the manufacturer.

CrELISA Procedure Using Crude Lysates of GT468 Expressing Bacterial Lysates

Preparation of the Antigen

E. coli XLOLR bacteria were transformed either with GT468 pQE plasmid or insertless pQE (will be referred to as "reference") and grown in LB medium to A600 nm~0.35 E. Protein expression was induced with 2 mM IPTG, and cells were allowed to grow for an additional 4 h at 37° C. Proper induction of protein expression and its kinetics were monitored by Coomassie gel analysis. Bacteria were spun down and resuspended in a small volume of PBS pH 7.2 containing 0.2 mM protease inhibitor AEBSF-hydrochloride (AppliChem). Cells were placed on ice and disrupted by sonication (Branson Sonic Power A Smithkline). GT468 and reference lysates were diluted to a total protein concentration of 2 mg/ml in PBS containing 0.2 mM AEBSF and 20% (v/v) glycerol. Aliquots were shock-frozen in nitrogen and stored at −70° C. until use.

Conduction of the Enzyme-Linked Immunosorbent Assay

Before use, GT468, as well as the reference lysates, was diluted in coating buffer (100 mM HEPES, pH 7.2), then transferred to flat-bottom F96 Maxisorp microwell plates (50 µl/well, Nunc) and adsorbed for 2 h at 37° C.

After antigen immobilization, plates were washed twice with washing buffer (50 mM Tris, 150 mM sodium chloride, pH 7.2) containing 0.1% Tween 20, and subsequently twice without detergent. Fifty microliters human sera diluted 1:100 was added per well and incubated for 1 h on an orbital shaker at ambient temperature. In some experiments, human sera were pretreated before subjecting them to the assay.

Each individual serum sample was tested in duplicate in parallel on wells coated with GT468 or reference lysate. Plates were washed again as described above and incubated for 1 h at room temperature with 50 µl/well of secondary antibody (goat anti-human IgG-AP, Dianova) diluted 1:5000 in 50 mM HEPES (pH 7.4) containing 3% (w/v) milk powder. Plates were developed with 100 µl/well of substrate solution[2 mg 4-nitrophenyl phosphate disodium salt hexahydrate (Merck) per ml ALP-buffer (Roche Diagnostics, Mannheim, Germany)] for 30 min at room temperature, and absorbance values immediately read at 405 nm on a microplate reader (Victor2 Wallac, Perkin-Elmer, Turku, Finland).

Flowcytometric Analysis

HEK293 cells transfected with GT468 pcDNA3.1 plasmid or insertless plasmid (mock) were harvested, fixed with ice-cold methanol, and blocked with PBS/10% FCS for 30 min. Cells were incubated with hybridoma supernatant for 1 h, washed twice with PBS/1 FCS for 10 min, and incubated with a goat anti-mouse Cy3 secondary antibody (Jackson ImmunoResearch Laboratories).

Western Blots

Whole cell lysates of HEK293 cells transfected with GT468 pcDNA3.1 plasmid or insertless plasmid (mock) were prepared using Triton-X based lysis buffer (50 mM HEPES (pH 7.4), 10%(v/v) Glycerol, 1% (v/v) Triton X-100, 150 mM NaCl, 1.5 mM $MgCl_2$, 5 mM EDTA, 100 mM NaF). Extracts were diluted in reducing sample buffer (Roth), subjected to SDS-PAGE and subsequently electrotransferred onto PVDF membrane (Pall). Immunostaining was performed with a polyclonal antibody reactive to GT468 (Koslowski et al. 2007) followed by detection of primary antibody with horseradish-peroxidase conjugated goat anti-rabbit secondary antibodies (Jackson ImmunoResearch Laboratories).

Example 2

GT468 is Aberrantly Activated and Highly Expressed in Various Tumors

To identify placenta-specific trophoblastic genes, a genome-wide data mining strategy was adapted, which we had originally developed for in silico identification of germ cell-specific molecules (Koslowski, M., Bell, C., Seitz, G., Lehr, H. A., Roemer, K., Muntefering, H., Huber, C., Sahin, U. & Tureci, O. (2004) *Cancer Res.* 64, 5988-5993; Koslowski, M., Tureci, O., Bell, C., Krause, P., Lehr, H. A., Brunner, J., Seitz, G., Nestle, F. O., Huber, C. & Sahin, U. (2002) *Cancer Res.* 62, 6750-6755; Koslowski, M., Sahin, U., Huber, C. & Tureci, O. (2006) *Hum. Mol. Genet.* 15, 2392-2399). In principle, hierarchical keyword search of GenBank was combined with digital cDNA-library subtraction for prediction of authentically placenta-specific genes. GT468 was identified by this approach.

Figure 1:
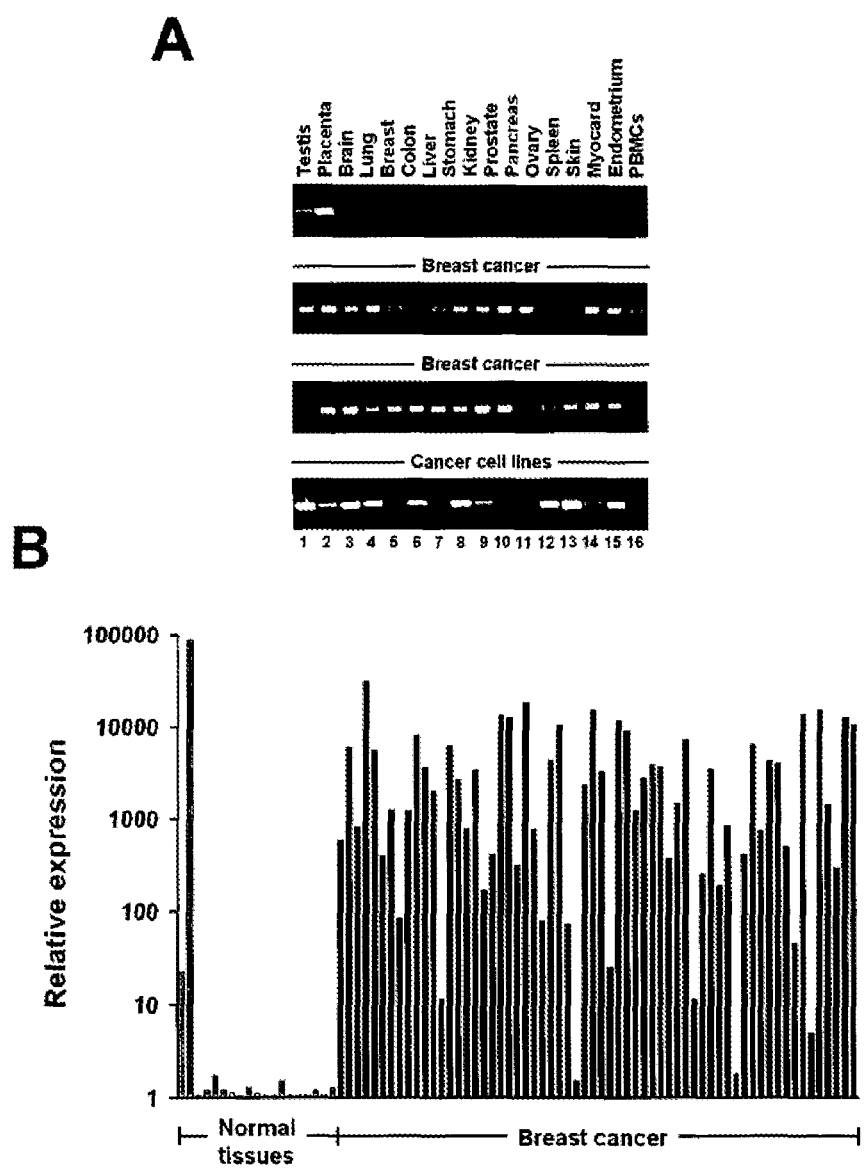
FIG. 1. GT468 is a trophoblastic lineage marker aberrantly activated in cancer cells. (A) End-point 35 cycle RT-PCR in normal tissues, primary breast cancer samples and cancer cell lines (1, MCF-7; 2, MDA-MB-435S; 3, BT-549; 4, MDA-MB-231; 5, SNU-16; 6, LCLC-103H; 7, KYSE-510; 8, KYSE-30; 9, EFO-27; 10, TOV-21G; 11, TOV-112D; 12, CAOV-3; 13, EFO-21; 14, FU-OV-1; 15, LNCAP; 16, CAPAN-2). (B) Quantitative 40 cycle real-time RT-PCR in normal tissues (1, Testis; 2, Placenta; 3, Brain; 4, Lung; 5, Breast; 6, Colon; 7, Liver; 8; Stomach; 9, Kidney; 10, Prostate; 11, Pancreas; 12, Ovary; 13, Spleen; 14, Skin; 15, Myocard; 16, Endometrium; 17, rest. PBMCs; 18, prolif. PBMCs; 19, Adrenal gland), primary breast cancer specimens and (C) cancer cell lines. (D) Quantitative real-time RT-PCR analysis of siRNA-mediated GT468 silencing in MCF-7 and BT-549 breast cancer cells. (E) Western blot analysis of siRNA-mediated decrease of GT468 protein expression. Control cells were either not treated or transfected with a scrambled non-silencing duplex (ns-siRNA). (F) Western blot analysis of GT468 protein levels in normal and neoplastic human tissues. (G) Immunohistochemistry of sections derived from normal human breast tissue (left) and breast cancer (right) using a GT468 specific antibody.
Figure 1:
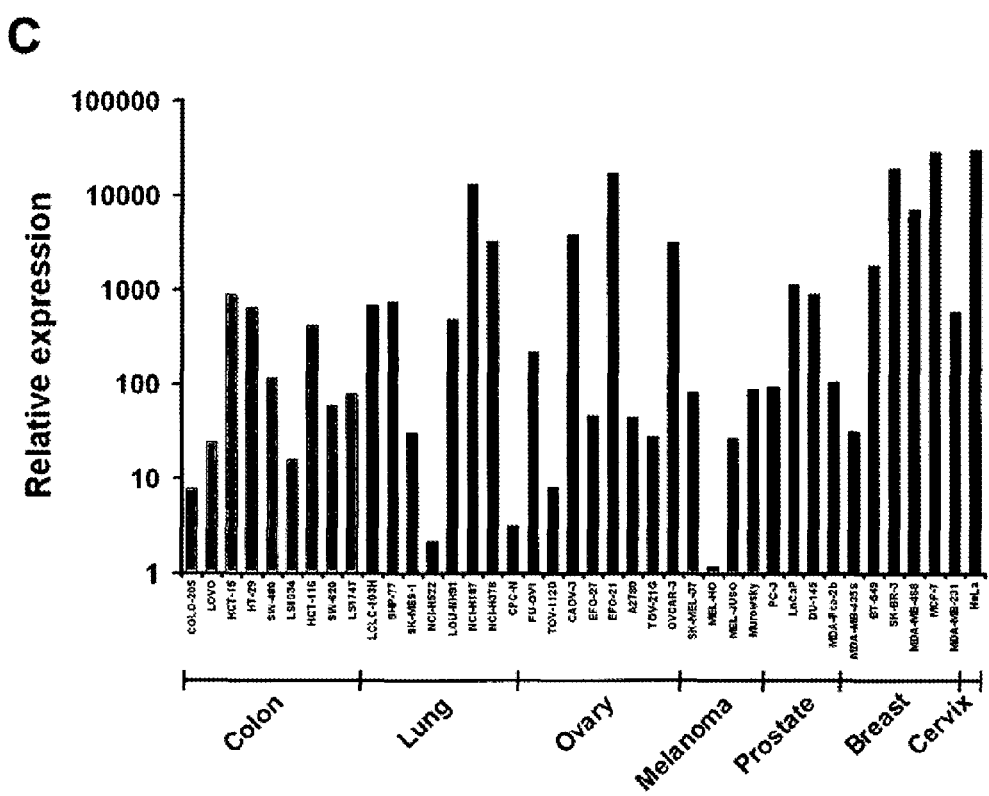

GT468 mRNA was investigated in a comprehensive set of normal and neoplastic tissue specimens by end-point RT-PCR and quantitative real-time RT-PCR. It was confirmed that GT468 expression is confined to placenta. In all other normal tissue specimens transcript amounts are below or just at the detection limit of highly sensitive RT-PCR (FIG. 1A, B, C, Tab. 1). The only exception is testis, albeit with transcript levels 3 to 4 logs lower than those observed in placenta.

TABLE 1

Expression of GT468 in tissues and cell lines typed by end-point RT-PCR

|  | GT468 expression |
|---|---|
| Normal tissues | |
| Testis | 2/3 |
| Placenta | 3/3 |
| Brain | 0/3 |
| Lung | 0/3 |
| Breast | 0/3 |
| Colon | 0/3 |
| Liver | 0/3 |
| Stomach | 0/3 |
| Kidney | 0/3 |
| Prostate | 0/3 |
| Pancreas | 0/3 |
| Ovary | 0/3 |
| Spleen | 0/3 |
| Skin | 0/2 |
| Myocard | 0/2 |
| Endometrium | 0/3 |
| rest. PBMCs | 0/3 |
| prolif. PBMCs | 1/6 |
| Small intestine | 0/3 |
| Thymus | 0/2 |
| Adrenal gland | 0/2 |
| Cancerous tissues | |
| Breast cancer | 44/62 |
| Lung cancer | 21/50 |
| Gastric cancer | 18/31 |
| Ovarian cancer | 2/9 |
| Hepatocellular carcinoma | 1/5 |
| Cancer cell lines | 22/40 |

In 38% (86/225) of primary tumor specimens across different cancer types and 55% (22/40) of tumor cell lines, however, aberrant activation of this gene with otherwise tightly controlled transcription was found. Prevalence and transcript levels of GT468 were highest in breast cancer and breast cancer cell lines (FIG. 1A, B, C). 44 of 62 (82%) primary breast cancer samples scored positive for GT468 expression (defined as at least 100-fold above background in non-trophoblastic normal tissues), with 24% (15/62) showing low (100-1000 fold), 40% (25/62) showing moderate (1000-10.000 fold), and 17% (11/62) showing high (>10.000 fold) expression (FIG. 1B). Moreover, we found GT468 transcription in 21 of 50 (42%) lung cancer samples as well as in gastric and ovarian cancer (Tab. 1). Induction of GT468 did not correlate with histological subtype, tumor stage or tumor grade.

Example 3

GT468 is Located on the Surface of Cancer Cells and is Accessible for Antibodies A polyclonal rabbit antibody (rabbit anti-GT468/C-term) against a GT468-specific peptide epitope (aa 117-127 of SEQ ID NO: 2) was raised. Specificity of the antibody was verified by gene silencing of GT468 using small interfering RNA (siRNA). To exclude siRNA off target activity experiments were conducted with two sets of GT468 specific siRNA duplexes, a scrambled non-silencing oligonucleotide and non-transfected cells. By transfecting breast cancer cell lines MCF-7 and BT-549 with these siRNA duplexes a stable and reproducible reduction of constitutive GT468 mRNA expression by 80-90% compared to controls was achieved (FIG. 1D). Consistent with this observation, the 26 kDa band, detected in accordance with the predicted size of GT468 in Western blot, nearly completely disappeared in both cell lines (FIG. 1E), proving both robust knockdown of GT468 protein expression and specificity of the antibody.

Western Blot staining of GT468 protein in primary human tissue samples with rabbit anti-GT468/C-term confirmed that this gene is detectable in breast cancer specimens in levels comparable to placenta as the only normal tissue it is expressed in (FIG. 1F). Immunohistochemistry with rabbit anti-GT468/C-term on human breast tumor sections showed specific immunoreactivity in specimens typed positive for GT468 mRNA expression by RT-PCR. Staining was confined to the neoplastic cell population, whereas adjacent stromal and non-neoplastic epithelial cells as well as patient matched normal tissues were not reactive (FIG. 1G). Immunostaining of tumor cells was accentuated at the plasma membrane, providing evidence that GT468 is a cell surface protein.

In silico analysis of the topology of the GT468 protein sequence predicted a hydrophobic domain spanning aa 5 to 22 followed by a large extracellular domain constituted by aa 23 to 212. Amino acids 29 to 119 of the extracellular part of GT468 represent a truncated zona pellucida (ZP) domain. The ZP domain is found in a variety of extracellularly exposed receptor-like proteins, including TGF-beta receptor type III, uromodulin, glycoprotein GP2 as well as the sperm receptors ZP2 and ZP3 (Bork, P. & Sander, C. (1992) *FEBS Lett* 300, 237-240) and is involved in polymerization (Jovine, L., Janssen, W. G., Litscher, E. S. & Wassarman, P. M. (2006) *BMC. Biochem.* 7, 11). The subcellular localization of constitutively expressed GT468 was assessed by immunofluorescence microscopy of MCF-7 and BT-549 breast cancer cells stained with rabbit anti-GT468/C-term, which has its epitope (aa 117 to 127) in the presumably extracellular part of the protein. Both cell lines displayed distinct staining at the cell membrane (FIG. 2A). Loss of signal upon siRNA-induced knock down of GT468 expression confirmed the specificity of the staining. Most importantly, specific membrane staining was observed not only on methanol-fixed but also non-fixed, native cells (FIG. 2B) implying that the epitope of the antibody is accessible without permeabilization of the cell membrane and thus supporting the predicted topology with extracellular localization of the carboxy-terminus.

Example 4 siRNA Induced Gene Silencing of GT468 Inhibits Motility, Migration and Invasion and Blocks Proliferation of Cancer Cells To determine the biological significance of GT468 in tumor cells the effects of its siRNA induced gene silencing on essential cell functions were studied.

Figure 3:
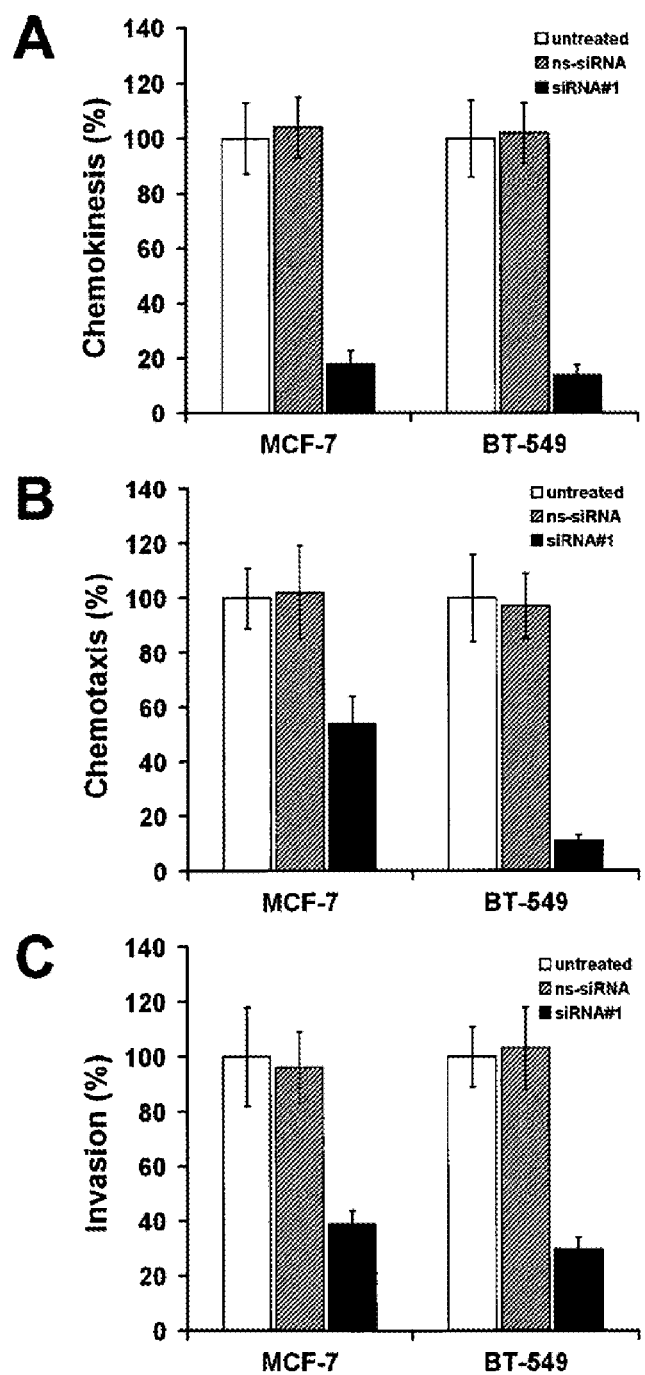
FIG. 3. GT468 expression promotes motility, migration and invasion of breast cancer cells. (A) Chemokinesis (motility) analysis in Transwell migration assays with 5% FCS added to the upper as well as the lower chamber was analyzed after 12 h. (B) Chemotaxis analysis of MCF-7 and BT-549 cells in Transwell migration assays 12 h after 5% FCS has been added to the lower chamber only to obtain a gradient. (C) Analysis of chemotactic invasion into Matrigel 24 h after 5% FCS as chemoattractant has been added to the lower chamber.

First, performance of breast cancer cell lines MCF-7 and BT-549 in transwell migration assays was investigated. Baseline motility (chemokinesis) of both cell lines assessed by adding 5% FCS as chemoattractant to both the upper and lower chamber of the system was substantially inhibited by GT468 specific siRNA duplexes (FIG. 3A). Consequently, we also observed a marked reduction of the directional chemotactic migratory capacity of the cells (FIG. 3B). Moreover, chemoinvasion activity of cells was profoundly affected by GT468 siRNA treatment, as cells were not able to migrate along chemoattractant gradients by breaking through a barrier of Matrigel (FIG. 3C).

Figure 4:
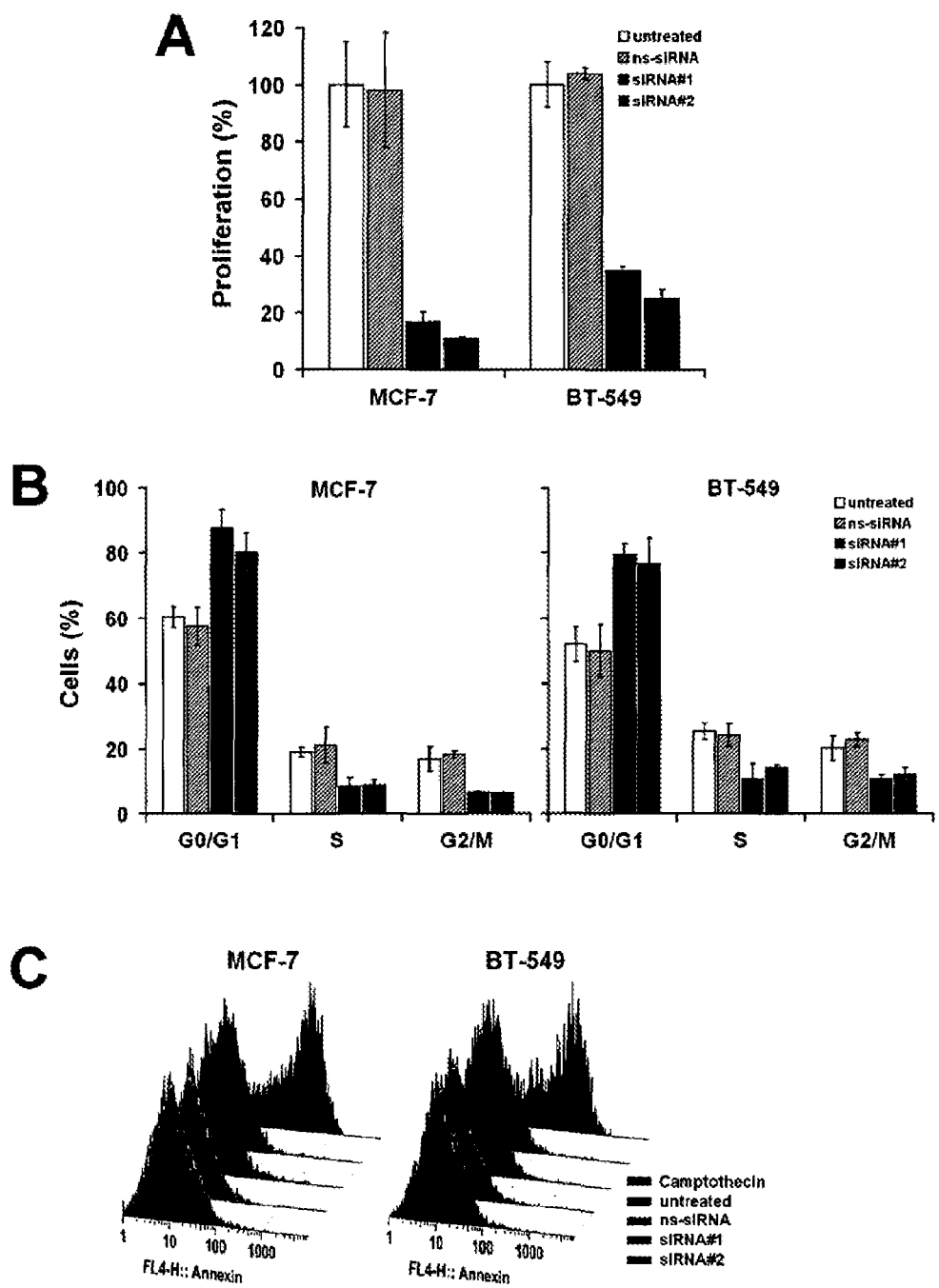
FIG. 4. GT468 expression promotes proliferation of breast cancer cells. (A) Analysis of proliferation in MCF-7 and BT-549 cells 72 h after knock down has been initiated by GT468 specific siRNA duplexes. (B) Cell cycle analysis of cells 72 h after initiation of GT468 silencing shown as bar chart of cell fractions in different cell cycle states. (C) Apoptosis of cells as determined by Annexin V staining 72 h after transfection with siRNA. As positive control for Annexin V staining cells were treated with 6 μM Camptothecin for 12 h.

Next, it was observed that tumor cell proliferation as measured by BrdU incorporation into DNA was reduced by 80-90% in both cell lines by GT468 specific siRNA duplexes (FIG. 4A). Cell cycle analysis revealed a distinct G1/S arrest in the cells transfected with GT468 siRNA as the underlying cause for the proliferation block (FIG. 4B). Vitality of the cells was not affected and staining for Annexin V gave no indications for apoptotic cell death (FIG. 4C).

Example 5

Treatment of Cancer Cells with Anti-GT468 Antibodies Inhibits Cell Growth

Figure 5:
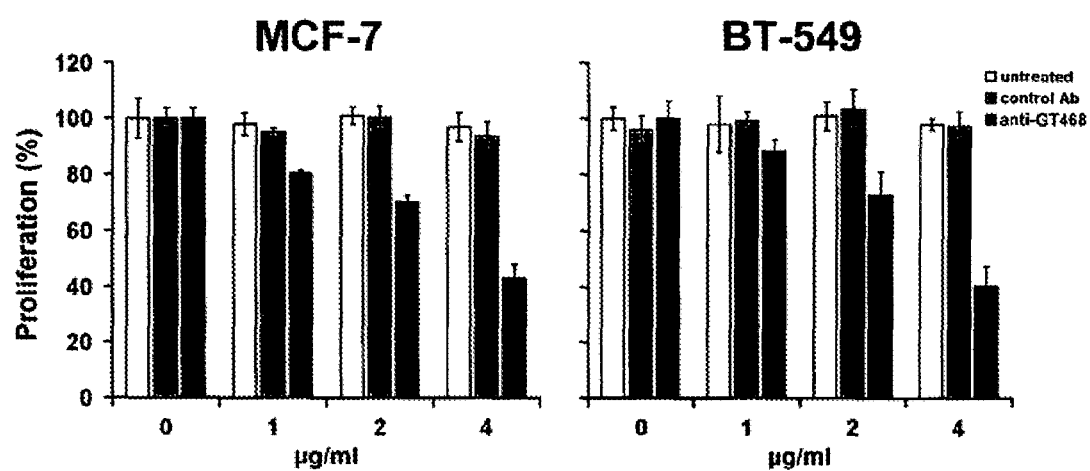
FIG. 5. GT468 is drugable by function-antagonizing antibodies. Proliferation analysis of MCF-7 and BT-549 cells after incubation with different amounts of anti-GT468 antibody and control antibody (isotype control) for 48 h.

We measured proliferation of MCF-7 and BT-549 cells incubated with rabbit anti-GT468/C-term and a non-reactive control antibody. Targeting of GT468 resulted in efficient inhibition of proliferation of both cell lines in a concentration-dependent manner (FIG. 5).

Example 6

Downstream Effects of siRNA-Induced Silencing and Antibody-Induced Functional Antagonization of GT468

Proliferation and cell cycle progression in eukaryotic cells is governed by cyclins and cyclin dependent kinases (CDKs). Individual cyclins act at different phases of the cell cycle by stimulating the activities of a series of CDKs. Restriction point control is mediated by cyclin D- and E-dependent kinase families (Morgan, D. O. (1997) Annu. Rev. Cell Dev. Biol. 13, 261-291; Sherr, C. J. (2000) Cancer Res. 60, 3689-3695). To investigate whether GT468 silencing induces the observed cell cycle dysregulation via alteration of cyclin expression, expression of cyclins D1, D2, D3 and cyclin E in MCF-7 and BT-549 breast cancer cells treated with GT468 siRNA was determined.

Interestingly, a significant reduction of cyclin D1 transcripts as measured by real-time PCR (FIG. 6A) as well as cyclin D1 protein levels in Western blot (FIG. 6B) occurred as a consequence of GT468 knockdown. No change in transcription levels was observed for the other cyclins analyzed.

Cyclin D1 is known to be a major regulator of the G1 to S progression of the cell cycle. Interestingly, in the tumorigenesis of sporadic breast cancer, overexpression of cyclin D1 is regarded as an early event (Caldon, C. E., Daly, R. J., Sutherland, R. L. & Musgrove, E. A. (2006) J. Cell Biochem. 97, 261-274; Sutherland, R. L. & Musgrove, E. A. (2004) J. Mammary. Gland. Biol. Neoplasia. 9, 95-104). D-type cyclins are unstable, and their induction, synthesis, and assembly with their catalytic partners all depend on persistent mitogenic signaling. Thus, D-type cyclins act as growth factor sensors, forming active kinases in response to extracellular factors (Sutherland, R. L. & Musgrove, E. A. (2004) J. Mammary. Gland Biol. Neoplasia. 9, 95-104; Sherr, C. J. (1993) Cell 73, 1059-1065). In breast cancer it has been shown, that cyclin D1 expression is controlled via a phosphatidylinositol 3-kinase (PI3K)/AKT-dependent pathway (Sutherland, R. L. & Musgrove, E. A. (2004)J. Mammary. Gland. Biol. Neoplasia. 9, 95-104; D'Amico, M., Hulit, J., Amanatullah, D. F., Zafonte, B. T., Albanese, C., Bouzahzah, B., Fu, M., Augenlicht, L. H., Donehower, L. A., Takemaru, K. et al. (2000) J. Biol. Chem. 275, 32649-32657; Muise-Helmericks, R. C., Grimes, H. L., Bellacosa, A., Malstrom, S. E., Tsichlis, P. N. & Rosen, N. (1998) J. Biol. Chem. 273, 29864-29872). AKT inactivates glycogen synthase kinase-3 beta (GSK-3β), thereby increasing cyclin D1 transcription as well as its proteolytic turnover and its protein levels in the nucleus (Sutherland, R. L. & Musgrove, E. A. (2004)J. Mammary. Gland. Biol. Neoplasia. 9, 95-104, Diehl, J. A., Cheng, M., Roussel, M. F. & Sherr, C. J. (1998) Genes Dev. 12, 3499-3511; Radu, A., Neubauer, V., Akagi, T., Hanafusa, H. & Georgescu, M. M. (2003) Mol. Cell Biol. 23, 6139-6149). In addition, the AKT pathway is an important regulator of cancer cell motility and migration (Sutherland, R. L. & Musgrove, E. A. (2004) J. Mammary. Gland. Biol. Neoplasia. 9, 95-104, Cantley, L. C. (2002) Science 296, 1655-1657; Luo, J., Manning, B. D. & Cantley, L. C. (2003) Cancer Cell 4, 257-262), two other cell functions in which GT468 is apparently involved. This prompted us to analyze whether GT468 has an impact on the regulation of AKT kinase in MCF-7 and BT-549 cells.

Constitutive phosphorylation and hyperactivation of AKT consecutive to PI3K overactivation is frequently observed in tumor cells. Quantification of levels of Ser473 phosphorylation of AKT (pAKT) subsequent to silencing of GT468 by siRNA technology and its functional antagonizing with antibody anti-GT468/C-term both resulted in a marked reduction of pAKT levels in particular in MCF-7 cells (FIG. 6C), suggesting that AKT kinase activation is involved in execution of down-stream effects of GT468. Interestingly, downregulation of pAKT was less prominent in BT-549 cells, which lack PTEN and therefore have a higher level of PI3K overactivation.

Example 7

GT468-Specific Monoclonal Antibodies

Peptides having sequences according to SEQ ID NOs: 3-10 were used for generation of hybridomas producing monoclonal antibodies. For example, immunization using the peptide of SEQ ID NO: 3 gave hybridomas 4E9-1H9 and 9B6-2A9, immunization using the peptide of SEQ ID NO: 4 gave hybridoma 59D6-2F2, and immunization using the peptide of SEQ ID NO: 6 gave hybridomas 61C11-2B5 and 78H11-1H6.

A peptide-specific ELISA was performed to ensure specific binding of the monoclonal antibodies. Hybridoma supernatants were tested in 1:5 or 1:10 dilution against the respective peptide used für immunization of mice. As control all hybridoma supernatants were tested against two irrelevant peptides. All monoclonal antibodies reacted specifically only with the respective peptide used for immunization of mice (FIG. 7).

Specific binding of the monoclonal antibodies to full-length GT468 protein was analyzed by immunofluorescence (IF) microscopy. 24 h after transfection of a GT468-eGFP fusion construct CHO cells were stained with hybridoma supernatants (1:5 dilution). Merging of the eGFP signal and the signal of secondary anti-mouse antibody (Alexa555) showed staining only of the GT468-eGFP transfected cells whereas non-transfected cells were negative (FIG. 8).

To analyze the impact of the monoclonal antibodies binding to GT468 on proliferation of cancer cells, endogenously GT468-expressing cancer cell lines BT-549, Caov-3, EFO-21, MCF-7, and MDA-MB-231 were incubated with hybridoma supernatants (1:2 dilution) for 72 h. Proliferation of cells was measured by BrdU incorporation into DNA. Whereas monoclonal antibody 4E9 1 H9 did not alter the proliferation of the cells at the concentration used, antibodies 9B6 2A9 and 59D6 2F2 clearly reduced the proliferation of all cancer cell lines analyzed (FIG. 9).

Thus, it was shown that monoclonal antibodies can be produced which selectively target GT468 expressed by cells. Furthermore, it was shown that monoclonal antibodies to GT468 can be produced which inhibit proliferation of cancer cells expressing GT468.

Example 8

GT468-Specific Monoclonal Antibodies Obtained from Immunization with GT468 pcDNA3.1 Plasmid Followed by Peptide/Protein Injection Twofold intramuscular immunization using GT468 DNA followed by twofold subcutaneous administration of recombinant GT468 protein resulted in hybridomas 22-1A-1, 22-2A-1, 22-9B-1, 23-33A-1 and 23-19A-1. Twofold intramuscular immunization using GT468 DNA followed by twofold intraperitoneal administration of the peptide according to SEQ ID NO: 10 resulted in hybridoma F11#33F7D12. Twofold intramuscular immunization using GT468 DNA followed by twofold intraperitoneal administration of the peptide according to SEQ ID NO: 3 resulted in hybridomas 4A12 2D4 1A10 and 4E9 1D12 2D4.

The following table lists the antibodies obtained and their isotypes.

TABLE 2

Monoclonal antibodies obtained by immunization with GT468 DNA followed by injection of peptide/protein

| Hybridoma | Isotype |
| --- | --- |
| 22-1A-1 | IgG2b |
| 22-2A-1 | IgG2b |
| 22-9B-1 | IgG2a |
| 23-33A-1 | IgG1 |
| 23-19A-1 | IgG1 |
| F11#33F7D12 | IgG1 |
| 4A12 2D4 1A10 | IgG1 |
| 4E9 1D12 2D4 | IgG3 |

A crude-lysate (CrELISA) was performed to ensure specific binding of the monoclonal antibodies from hybridomas 22-1A-1, 22-2A-1, 22-9B-1, 23-33A-1, and 23-19A-1. Hybridoma supernatants were tested against the lysate of *E. coli* transformed with GT468 pQE expression vector. As control, hybridoma supernatants were tested on lysate of *E. coli* transformed with insertless (mock) pQE plasmid. All monoclonal antibodies reacted specifically only with the specific GT468 lysate (FIG. 10A).

A peptide-specific ELISA was performed to ensure specific binding of the monoclonal antibodies from hybridomas F11#33F7D12, 4A12 2D4 1A10, and 4E9 1D12 2D4. Hybridoma supernatants were tested against the respective peptide used for immunization of mice. As control, hybridoma supernatants were tested against an irrelevant peptide. The monoclonal antibodies reacted specifically only with the respective peptide used for immunization of mice (FIG. 10 B).

Specific binding of the monoclonal antibodies to full-length GT468 protein was analyzed by flowcytometric analysis as described herein. For flowcytometric analysis of monoclonal antibody 4E9 1D12 2D4 transiently transfeted HEK cells with a transfetion rate of approx. 40% were used. All hybridoma supernatants showed specific staining of GT468 transfected cells, whereas no staining was observed on mock transfeted cells (FIG. 11).

Specific binding of the monoclonal antibodies to full-length GT468 protein was analyzed by Western blot. All hybridoma supernatants showed specific reactivity with lysates of HEK293 cells transfected with GT468 pcDNA3.1 expression plasmid, whereas lysates of mock transfeted cells showed no signal (FIG. 12; The faint signal of hybridoma supernatant 23-33A-1 in the mock lysate is believed to result from spillover of the HEK GT468 lysate).

A peptide ELISA was performed to identify epitopes in the GT468 protein to which the monoclonal antibodies bind to. The complete GT468 protein sequence was synthesized as set of 51 overlapping peptides (15mers) with an overlap of 11 aa. All hybridoma supernatants were tested in ELISA for specific binding to these peptides. As control, an irrelevant peptide was used. All supernatants showed specific binding to GT468 peptides. Hybridoma supernatants 22-1A-1, 23-33A-1, and 23-19A-1 each showed binding to two overlapping peptides implying reactivity to a linear epitope of GT468. The binding patterns of 22-2A-1 and 22-9B-1 were more complex, implying reactivity to conformational epitopes of the GT468 protein.

To analyze the impact of the monoclonal antibodies binding to GT468 on proliferation of cancer cells, endogenously GT468-expressing cancer cell lines SK-BR-3 (4A12 2D4 1A10) or MCF-7 (4E9 1D12 2D4) were incubated with purified hybridoma supernatants for 72 h or 120 h at the concentrations indicated in FIG. 14. Proliferation of cells was measured by BrdU incorporation into DNA. Whereas the irrelevant control monoclonal antibody did not alter the proliferation of the cells, monoclonal antibodies 4A12 2D4 1A10 and 4E9 1D12 2D4 clearly reduced the proliferation of cells in a concentration dependent manner (FIG. 14).

The invention claimed is:

1. An isolated antibody having the ability of binding to a peptide consisting of an amino acid sequence selected from the group consisting of SEQ ID NO: 3-10 and 35-79 and mediating inhibition of proliferation of cells expressing a protein comprising the amino acid sequence of SEQ ID NO: 2 and/or are characterized by association of a protein comprising the amino acid sequence of SEQ ID NO: 2 with the cell surface.

2. The isolated antibody of claim 1, wherein said inhibition of proliferation of said cells is induced by binding of said antibody to a protein comprising the amino acid sequence of SEQ ID NO: 2 expressed by said cells and/or associated with the surface of said cells.

3. The isolated antibody of claim 2, wherein said antibody binds to the extracellular domain of a protein comprising the amino acid sequence of SEQ ID NO: 2 expressed by said cells and/or associated with the surface of said cells.

4. The isolated antibody of claim 1, wherein said cells are cancer cells.

5. The isolated antibody of claim 4, wherein said cancer cells are selected from the group consisting of tumorigenic breast, lung, gastric, ovarian, liver, colon, pancreatic, esophageal, head-neck, renal, prostate and hepatocellular cancer cells.

6. The isolated antibody of claim 1 which is a monoclonal, chimeric, human or humanized antibody, or an antigen-binding fragment of an antibody.

7. The isolated antibody of claim 1 selected from the group consisting of an IgG1, an IgG2, an IgG3, an IgG4, an IgM, an IgA1, an IgA2, a secretory IgA, an IgD, and an IgE antibody.

8. The isolated antibody of claim 7 selected from the group consisting of an IgG2a and IgG2b antibody.

9. The isolated antibody of claim 1, wherein the antibody binds specifically to a protein comprising the amino acid sequence of SEQ ID NO: 2.

10. The isolated antibody of claim 1 which binds to native epitopes of a protein comprising the amino acid sequence of SEQ ID NO: 2 present on the surface of living cells.

11. The isolated antibody of claim 1, wherein said protein comprising the amino acid sequence of SEQ ID NO: 2 is expressed on the surface of said cells.

12. A hybridoma or recombinant cell producing the antibody of claim 1.

13. An antibody produced by the hybridoma or recombinant cell of claim 12.

14. A conjugate comprising the antibody of claim 1 coupled to a therapeutic agent.

15. The conjugate of claim 14, wherein the therapeutic agent is a toxin, a radioisotope, a drug or a cytotoxic agent.

16. A pharmaceutical composition comprising the antibody of claim 1 and a pharmaceutically acceptable carrier.

17. A pharmaceutical composition comprising the antibody of claim 13 and a pharmaceutically acceptable carrier.

18. A pharmaceutical composition comprising the conjugate of claim 14 and a pharmaceutically acceptable carrier.

* * * * *